(12) United States Patent
Tischfield et al.

(10) Patent No.: US 6,352,849 B1
(45) Date of Patent: Mar. 5, 2002

(54) MAMMALIAN PHOSPHOLIPASE $A_2$ NUCLEOTIDE SEQUENCES, LOW MOLECULAR WEIGHT AMINO ACID SEQUENCES ENCODED THEREBY, ANTISENSE SEQUENCES AND NUCLEOTIDE SEQUENCES HAVING INTERNAL RIBOSOME BINDING SITES

(75) Inventors: Jay A. Tischfield, 9982 Mill Run, Carmel, IN (US) 46032; Jeffrey J. Seilhamer, Los Altos Hills, CA (US)

(73) Assignees: Jay A. Tischfield, Piscataway, NJ (US); Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/362,230

(22) Filed: Jul. 28, 1999

Related U.S. Application Data

(62) Division of application No. 08/888,497, filed on Jul. 7, 1997, now Pat. No. 5,972,677, which is a continuation of application No. 08/651,405, filed on May 22, 1996, now abandoned, which is a continuation of application No. 08/097,354, filed on Jul. 26, 1993, now abandoned.

(51) Int. Cl.$^7$ .............................. C12N 15/55; C12N 9/20
(52) U.S. Cl. .................. 435/198; 536/23.2; 435/320.1; 435/252.3; 435/325
(58) Field of Search ........................ 536/23.2; 435/198, 435/320.1, 252.3, 325

(56) References Cited

U.S. PATENT DOCUMENTS 5,019,508 A 5/1991 Johnson et al. ............. 435/198

OTHER PUBLICATIONS

Westermann, et al., "Inhibition of expression of SV40 virus large T-antigen by antisense oligodeoxyribonucleotides," *Biomed. Biochim. Acta*, 48(1), pp. 85–93, 1989.

Seilhamer et al., "Novel Gene Exon Homologous to Pancreatic Phospholipase $A_2$: Sequence and Chromosomal Mapping of Both Human Genes," *J. of Cellular Bio.*, 39, pp. 327–337, 1989.

Macejak et al., "Internal initiation of translation mediated by the 5' leader of a cellular mRNA," *Nature*, 353, pp. 90–94, 1991.

Young et al., "Utilization of an Epstein–Barr virus replicon as a eukaryotic expression vector," *Gene*, 62, pp. 171–185, 1988.

Bekkers et al., "The use of genetic engineering to obtain efficient production of porcine pancreatic phospholipase A2 by *Saccharomyces cerevisiae*,"*Biochim. et Biophisica Acta*, 1089, pp. 345–351, 1991.

Deng et al., "A novel expression vector for high–level synthesis and secretion of foreign proteins in *Escherichia coli*: overproduction of bovine pancreatic phospholipase $A_2$," *Gene*, 93, pp. 229–234, 1990.

R.L. Heinrikson, "Dissection and Sequence Analysis . . . ," *Meth. in Enzymology*, 197, pp. 201–214, 1991.

Davidson et al., "Evolutionary Relationships and Implications for the Regulation of Phospholipase $A_2$ from Snake Venom to Human Secreted Forms," *J. Mol. Evol.*, 31, pp. 228–238. 1990.

Murakami et al., "The Functions of Five Distinct Mammalian Phospholipase $A_2$s in Regulating Arachidonic Acid Release," *J. of Bio. Chem.*, 273(23), pp. 14411–14423, 1998.

J.A. Tischfield, "A Reassessment of the Low Molecular Weight Phospholipase $A_2$ Gene Family in Mammals," *J. of Bio. Chem.*, 27(28), pp. 17247–17250, 1997.

Reddy et al., "Analysis of the Secretory Phospholipase $A_2$ That Mediates Prostaglandin Production in Mast Cells," *J. of Bio. Chem.*, 272(21), pp. 13591–13596, 1997.

Chen et al., "Localization of Group IIc Low Molecular Weight Phospholipase $A_2$ mRNA to Meiotic Cells in the Mouse," *J. of Cell. Biochem.*, 64, pp. 369–375, 1997.

Balboa et al., "Novel Group V Phospholipase $A_2$ Involved in Arachidonic Acid Mobilization in Murine $P388D_1$ Macrophages," *J. of Bio. Chem.*, 271(50), pp. 32381–32384, 1996.

(List continued on next page.)

Primary Examiner—Rebecca E. Prouty
(74) Attorney, Agent, or Firm—Jenkens & Gilchrist A Professional Corporation

(57) ABSTRACT

Novel mammalian phospholipase ($PLA_2$) nucleotide sequences and low molecular weight (about 14 KD) amino acid sequences encoded thereby are disclosed. More particularly, a cloned human $HPLA_2$ cDNA expressing $HPLA_2$-10 and its cloned rat $RPLA_2$ cDNA counterpart, expressing $RPLA_2$-10, which are characterized as $PLA_2$ Type IV, are disclosed. A second type of $PLA_2$ cDNA, characterized as $PLA_2$ Type III and exemplified by a rat $PLA_2$ cDNA encoding $RPLA_2$-8 and a partial human $PLA_2$ nucleotide sequence encoding $HPLA_2$-8, is disclosed. Expression of the cDNAs encode the two new types of $PLA_2$ enzymes which have phospholipase activity. The novel $PLA_2$s do not include disulfide bridges between cysteine amino acids 11 and 77 or elapid loops. However, the novel $PLA_2$s may include amino acid COOH-terminal extensions which can vary in length. Seventeen of the eighteen absolutely conserved amino acids in all active 14 KD $PLA_2$s are believed to be conserved in $RPLA_2$-8 and $HPLA_2$-8, whereas all eighteen are believed to be conserved in $RPLA_2$-10 and $HPLA_2$-10. Because the encoded sequences of $RPLA_2$-8 and $HPLA_2$-8 include only 16 cysteine amino acids, they have been designated as Type III. $RPLA_2$-10 and $HPLA_2$-10 are designated as Type IV since their encoded sequences include only 12 cysteine amino acids.

14 Claims, 46 Drawing Sheets

OTHER PUBLICATIONS

Tischfield et al., "Low–Molecular–Weight, Calcium–Dependent Phospholipase $A_2$ Genes are Linked and Map to Homologous Chromosome Regions in Mouse and Human," *Genomics*, 32, pp. 328–333, (1996).

Chen et al., "Cloning and Recombinant Expression of a Novel Human Low Molecular Weight $Ca^{2+}$–dependent Phospholipase $A_2$," *J. of Bio. Chem.*, 269(4), pp. 2365–2368, 1994.

Chen et al., "Cloning and Characterization of Novel Rat and Mouse Low Molecular Weight $Ca^{2+}$–dependent Phospholicpase $A_2$s Containing 16 Cysteines," *J. of Bio. Chem.*, 269(37), pp. 23018–23024, 1994.

Chen et al., "Cloning, expression and partial characterizatin of a novel rat phospholipase $A_2$," *Biochim. et Biophysica, Acta*, 1215, pp. 115–120, 1994.

Spirio et al., "Three Secretory Phospholipase $A_2$ Genes That Map to Human Chromosome 1P35–36 Are Not Mutated in Individuals with Attenuated Adenomatous Polyposis Coli," *Cancer Res.*, 56, pp. 955–958, 1996.

RPLA2-8 cDNA Structure

RPLA2-8 cDNA Secondary Structure

Fig. 3A

```
           10         20         30         40         50         60
GAATTCCGCCTCCACCTCTCAAATGCTGGGATTGCAGGATGTCCCCCCACCCCTGCTCCC
clone linker
           70         80         90        100        110        120
TTGTGTCCTTGCTTCCTGCTGCCGGAATGTATCACTTAATTGCCAGGTACCCATGGTCTG
             Pla8-8 (primer)
          130        140        150        160        170        180
ATTCCAGGATAGAAGGGCGGGCGAGGGGGTTGGAGGAGAGGCCTCTATTATTTCCGCGGT 190        200        210        220        230        240
CTGGCAGGCCTGGAAGCAAAGCTTCAAGTGCAGAAGGAGGAGTGTCGGGGAATGGCAGAA
            Pla8-7 (primer)
          250        260        270        280        290        300
AAGGCTGGAACAGCAATGCAGACCTAGGTAAAGGGCACAGAGCTGAGGGAAGCTCCTGGG 310        320        330        340        350        360
AGGCTCCCTGCAGCTCCTGCCTCTGCACATGACCCGGACTCCTTTTCTCTCTTTGGATCT 370        380        390        400        410        420
GCGTCCAGGGACTGGCTTGTACACACCCCTCCCAGGAGACCCCTTGGCAGCTGCACACTC 430        440        450        460        470        480
AGGCTCCATCCAAGTTGGCTCTGCCCCTGGGGAAGGCTGCTCAAAAGGCCTGGCTCCCAG 490        500        510        520        530        540
TTTCTGGGGACCCACAGAGAGCCTCTCACCTCGCAGCTCAGCTCCATCCGCCTCCTGTGC 550        560        570        580        590        600
CTGGCTGCGACCAGCTGGGTCTAACTATAGACAGTCAGCAACTTCAGCCACTTCACCGAG 610        620        630        640        650        660
TTTCCCAACAGCTTTGAGATTTGGAAGCCGGAAGCCTGACTGCCTTCTCAGAAGCTACGG 670        680        690        700        710        720
TCCACTACCTCAGCCATTCTGTTGGAGCTGAACTGGCAGATGAAGGTGAGACCCAGGCAC 730        740        750        760        770        780
CATGGACCTCCTGGTCTCCTCAGGAATGAAGGGCATCGCTGTCTTCCTTGTCTTTATCTT
 MetAspLeuLeuValSerSerGlyMetLysGlyIleAlaValPheLeuValPheIlePh
 Rclo8-5' (primer)
          790        800        810        820        830        840
CTGCTGGACAACCTCCACCCTCAGCAGCTTCTGGCAGTTCCAGAGGATGGTCAAACACAT
 eCysTrpThrThrSerThrLeuSerSerPheTrpGlnPheGlnArgMetValLysHisIl
                                Pla8-1 (primer)
          850        860        870        880        890        900
CACGGGGCGCAGCGCCTTCTTCTCCTATTACGGATATGGCTGCTACTGTGGCTTGGGG
 eThrGlyArgSerAlaPhePheSerTyrTyrGlyTyrGlyCysTyrCysGlyLeuGlyGl 910        920        930        940        950        960
CCGAGGGATCCCTGTGGACGCCACAGACAGGTGCTGCTGGGCTCATGACTGTTGCTACCA
 yArgGlyIleProValAspAlaThrAspArgCysCysTrpAlaHisAspCysCysTyrHi
```

---

RPLA2-8 cDNA sequence corresponds to SEQ ID NO. 21:
and Derived Amino Acid Sequence corresponds to SEQ ID NO. 22:

Fig. 3B

Pla8-2 (primer)

```
             970       980       990      1000      1010      1020
        CAAGCTTAAGGAATATGGCTGCCAGCCCATCTTGAATGCCTATCAGTTTGCCATTGTCAA
        sLysLeuLysGluTyrGlyCysGlnProIleLeuAsnAlaTyrGlnPheAlaIleValAs 1030      1040      1050      1060      1070      1080
        CGGGACCGTGACCTGTGGATGCACCATGGGTGGCGGCTGCTTGTGCGGGCAGAAAGCCTG
        nGlyThrValThrCysGlyCysThrMetGlyGlyGlyCysLeuCysGlyGlnLysAlaCy 1090      1100      1110      1120      1130      1140
        TGAGTGTGACAAACTGTCTGTGTACTGCTTCAAGGAGAACCTGGCCACCTACGAGAAAAC
        sGluCysAspLysLeuSerValTyrCysPheLysGluAsnLeuAlaThrTyrGluLysTh 1150      1160      1170      1180      1190      1200
        TTTCAAGCAGCTCTTCCCCACCAGGCCCCAGTGTGGCAGGGACAAACTCCATTGCTAGGC
        rPheLysGlnLeuPheProThrArgProGlnCysGlyArgAspLysLeuHisCysEnd
                                                    Rclo8-3' (primer)
            1210      1220      1230      1240      1250      1260

1270      1280      1290      1300      1310      1320
        CTTCCCCTCCAAGAGTCCCCAGGCTCCTGCAGCTCAGCCTTGCTGTCTAGGGAGTGTCTT 1330      1340      1350      1360      1370      1380
        CTCAGGCATTAGGGGACCGGAGGTGGAGAATTCCTGCCCTGGAATCAGACCATGGGTACC 1390      1400      1410      1420      1430      1440
        TGGCAATTAAGTGATACATTCCGGCAGCAGGAAGCAAGGACACAAGGGAGCAGGGGTGGG 1450      1460      1470      1480      1490      1500
        GGGACATCCTGCAATCCCAGCATTTGAGAGGTGGAGGCAAGAGGTGGGGGGTAGCCTCCA 1510      1520      1530      1540      1550      1560
        CTATACGGTAAGTTCAAGGCTAACCTGAGCTACCTGAGACCTTGCCTTGAAAAAACTTTT 1570      1580      1590      1600      1610      1620
        TTAAAAAACGTTTAAAGGAAAAGAAAACAGAAAGACACGGGGACTGGGCTGAAAGGTACT 1630      1640      1650      1660      1670      1680
        CTCAAACCGATTTCCCAGGAAGAGCGGAGAGCCCCAGGTTCAGCTCCAGCCTGAACTCCC 1690      1700      1710      1720      1730      1740
        CCATACCCTCAGTCCTGGTCAGGATGTGTGTCTGACTGGGGAACCAAGTCCTCCACCCGG 1750      1760      1770      1780      1790      1800
        GTGGAGCTTAGCTGGGAACTACGCAGGTGTCCTAGAAAATACAGTCCTAAGAGCCTCACC 1810      1820      1830      1840      1850      1860
        CGGAGTCTCATCCCCATTTGCTCCAGGACTGACCTCTGTAAATCTTCCAGCAGGAAGCAG 1870      1880      1890      1900      1910      1920
        GCTGTACCCATCTCAGGAGGTGGGGTGCTGTTAGAACAATGGTGTGCACCAGTGACACAA 1930      1940      1950      1960      1970      1980
```

Fig. 3C

```
AGATGTCATGGTTAAGATGGCATCAAGAAGTGGAAAGGACATTCGGAACAGTGGGTCCAA
     1990      2000      2010      2020      2030      2040
GGCACCCAAAGTCCTCACCCCAATTTAGAAGCCGTTGGTCCTGTAAGACTTAAATCTACT
     2050      2060      2070      2080      2090      2100
AAACAAGGAAGGTCTAACTGGGCTGGAATCTGAAGTTCATGGTGCCAGGCTGGGCGGTG
     2110      2120      2130      2140      2150      2160
GGTGGGGACGTGGCCGTGGCCATGACCATGATTGCCTCTCTGCATGGTGACACTTGCCTT
     2170      2180      2190      2200      2210      2220
TTGCACCCTAGCTCTCAGCACATCTGAAAAGGACAGACTCTCCTGTTCATTCCTTGAATC
     2230      2240      2250      2260      2270      2280
TGAGACTCTCCTCACTAATGTAGCAAAAATGGAGGTCTAAAGTGCAGGCTTCAGCCTCTG
     2290      2300      2310      2320      2330      2340
AGGTCCAGGGCAGGAGGAAGCTGGGGCTCAGCCTCCTGGAGGATGAGAGCTTGCCGGGTG
     2350      2360      2370      2380      2390      2400
AGCATCAGCGACAGCAGACCCTTGGGCTCAGAGAGTCCGCAAGCCTGGGAGAGCCTGGCC
     2410      2420      2430      2440      2450      2460
GAGCCCTGACTGCAGCACACAGAGCCGTGAGCCTCATACAAGAAGCCACATTTTGGGGAA
     2470      2480      2490      2500      2510      2520
GCTTCAGGGTGGCTGATTCCACAGCTGTTGGGTTCAGAACGGAAGCCGGGAGCACTCACT
     2530      2540      2550      2560      2570      2580
TCAGATATGGAAGCTTTGTTTTACGAGCGCTTAGCACCAGTTCAGGATCTGAACTTCGTC
     2590      2600      2610      2620      2630      2640
CTGACCGGAGAGTCCGTACCACATTTTTATAGGATGGGAACACAGAGCGAGGGGCGTGGA
     2650      2660      2670      2680      2690      2700
GTAAGCTGTTGAACGACCGATCATATTTTGACCTAAGAGGTTAAGTAAGGACGTTAACAT
     2710      2720      2730      2740      2750      2760
GGGTGACTGGGCATTAGTCAGGTCACCTGGTTTTGGGGTCTTTGAATCAGCTTTCGTGGC
     2770      2780      2790      2800      2810      2820
CAGGTCCCTTCCTGGACTTTGGCTCGGAATTTAGAACGATAAGGGAACGAAGAGGTGGGC
     2830      2840      2850      2860      2870      2880
AAGCTTCGGGCAGTCAGTAAGAGGCAGCACATTCATGACCTGTGTGCCTTGTTTAGATAA
     2890      2900      2910      2920      2930      2940
TGGGATAAGAGTATCTCCTCTCTTACACCCCTTACTGGTTAACAGACAAACACGAGACAT
     2950      2960      2970      2980      2990      3000
CTGAAGAAGCAGGACAGGAGTTAGGTTCTGGGGCACAGGAACATGAACTCGGTTTTGATC
     3010      3020      3030      3040      3050      3060
```

Fig. 3D

```
CTGCCGGCAAGGTGGATCTTGTTCCTGAGAAGGCTGGACTCAGGAAACTTCCTCTTAACA
     3070      3080      3090      3100      3110      3120
AGTTAGTTGATGGCGCTGGTCCTTAGTCACCGATACTGTCAGGCTCTCAGCTCTTGGGCC
     3130      3140      3150      3160      3170      3180
AGACTTGGCGGCCATGGGAGTGTGGTCACTTGCCCCGTCCCCTTCTTCCAGGAGGTACTG
     3190      3200      3210      3220      3230      3240
GGGAAAATGGTTGGATTTGTGGAGTTGTAGGGAACACTCATGGCTCCCTTCACTTAGTAG
     3250      3260      3270      3280      3290      3300
GTCAGCTAACATATGTGTATCGAGCCCATACCGTGTGCCATGTGCAGTGCTGAGCAGCAG
     3310      3320      3330      3340      3350      3360
GGAGTCAGAGATTTAAAGACACACACAGACTTCAAGTCTGAGAATTTTCAATCCCAGG
     3370      3380      3390      3400      3410      3420
GAGAACCGCTGAGAGCCATGGCGCTTCTACCAATGCCAGAGGCTAACACCCGGACTGAGA
     3430      3440      3450      3460      3470      3480
AAACTAAGCACGAGGAGACAGCAGGGTCAGCAGAGGGCCTGGGAGCTAGGGCCCTGAGCA
     3490      3500      3510      3520      3530      3540
GTACCTAGTTCAAATCACAGAGTCGTCTTTCTTCCTCCACCCTACCCAGGTACAGCAAGT
     3550      3560      3570      3580      3590      3600
AGACACGGGTGGGGGCAGGGCAGGGATGCAGGAACATTAGGGCACACCGATGTGGCTAGG
     3610      3620      3630      3640      3650      3660
CTAAGCTAGAGCATGTTACCTTCTCAGGGGTCCTGTCATGTCAGAGACTGGTTCCAACCT
     3670      3680      3690      3700      3710      3720
GGAAAGATGTCTGAGTGACAGCTGTGGTAGAAGAAGAGAGGCCAGGGTGATATCAGCATG
     3730      3740      3750      3760      3770      3780
AAGGGCTGGATTGCTATGTGAGATCCAGATCTCTTCTGCCACTGGGGTCAGCTTCTACAC
     3790      3800      3810      3820      3830      3840
TGGAAATAGATGGGCTGCGTTATGGAGGGTGGTGTGAGTCCCTGTCTGCGTTGTGCCGGG
     3850      3860      3870      3880      3890      3900
AATCAGAGCAGAGTGTTAGCGCTGTAAAAGGACATGCTGGTGCTTGCAGGAAATCATCGA
     3910      3920      3930      3940      3950      3960
TTTCTTGGAAGGGCAGCCATTCATCTACACCAGGGATTGACTTTATGCCAGGCTTGTGAT
     3970      3980      3990      4000      4010      4020
GAGGGTAGAAAAGTAGAAATTCTGTCCGCTGCAAGGAGCAGTCAGAGGACACAAGGACCA
     4030      4040      4050      4060      4070      4080
AATAGCTTGGGAGTTGCGGAAGTAGGTGTCTGCTGAGGGAGCAGTGACCACTGGGGGAAA
     4090      4100      4110      4120      4130      4140
```

Fig. 3E

```
GGCTCCTTCAAGGAATTCAGGGACAGGGGTGAGGGCTGACATCTTGCCTGAGACCCTAAA 4150      4160      4170      4180      4190      4200
GAAGAGAAGGAGTTGAGAGGGCTGAGTATGCTGTGTGGAGCCCCACCCCCACCCCCACCC 4210      4220      4230      4240      4250      4260
CCACCCCCACCCCAGGTATATGGATGGAGGATAATGCGGGGGTCGGGTTCCTCTCAAATC 4270      4280      4290      4300      4310      4320
CATCATCCCACCTTCGAGCTGCTGGCACGGCCTTGCCAGCACAGCCCGATTCTGTGTTGA 4330      4340      4350      4360      4370      4380
CAAAATACTCGAACGAAATGATTACATGCAAATAAAATGCAAGAGGAAAAATCTAAACGG
                               Polyadenylation site
```

AATTC
clone linker

FIGURE 5

```
400  ACCTCAGACCCCCTGGTCTCCTCAGGAATGAAGGTCATTGCCATCCTCACCCTCCTC
         |||   ||| |||||||||||||||||||||||||  ||   ||
719  ACCATGGACCTCCTGGTCTCCTCAGGAATGAAGGGCATGCGCTGTCTTCCTTGTCTTTATC

460  TTCTGCT
     |||||||
     TTCTGCT
```

Matches = 51          Mismatches = 16       Unmatched = 0
Length = 67           Matches/Length = 76.1 Percent Top strand is HPLA2-8 exon I sequence; bottom is RPLA2-8 exon I sequence.
The underlined ATG is the putative RPLA2-8 translation start codon.

———————————————————————————————

Top strand is SEQ ID NO: 23:;
Bottom is SEQ ID NO: 24:.

FIGURE 6

```
2633  tgg TGGCAGCCCCCACCCACAGCAGTTTCTGGCAGTTTCAGAGGAGGGTCAAACACATCACGG
          |||||||||  ||||||  ||||||||||||||||  ||||||||||||  |||||||||||
786   cag GGACAACCTCCACCCTCAGCAGCTTCTGGCAGTTCCAGAGGATGGTCAAACACATCACGG 2693      GGCGAAGTGCCTTCTTCTCATATTACGGATATGGCTGCTACTGTGGGCTTGGGGATAAAG
          |||| ||||||||||||||||  ||||||||||||||||||||||||||||||||||  |
846       GGCGCAGCGCCTTCTTCTCCTATTACGGATATGGCTGCTACTGTGTGGGCTTGGGGCCGAG 2753      GGATCCCCGTGGATGACACTGACAG gtg
          ||||||| ||||| |||| |||||||
906       GGATCCCTGTGGACGCCACAGACAG Matches = 126    Mismatches = 19    Unmatched = 0
Length = 145     Matches/Length = 86.9 Percent Top strand is HPLA2-8 coding exon II sequence; bottom is RPLA2-8
exon II sequence.
```

---

Top strand is SEQ ID NO: 25;
Bottom strand is SEQ ID NO: 26:.

FIGURE 7

```
13862  tag  GTGGATGCACCCCTTGGTCCTGGTGCCAGTCTGCCACTGCAGGCTGAAGGCCTGTGAGTGT
            |||||||||||  ||||   |||||||||| |||||||||||||||||||||||||||||
1034   cag  GTGGATGCA   CCATG   GGTGGCGGCTGCTTGTGCGGGCAGAAAGCCTGTGAGTGT 13921       GACAAGCAATCCGTGTGCACTGCTTCAAAGAGAGCCTGCCCACCTATGAGAAAACTTCAAG
            |||| |||||| |||||||| |||||||| ||||||||||||||||||| ||| ||||||
1088        GACAAACTGTCTGTGTACTGCTTCAAGGAGGAACCTGGCCACCTACGAGAGAAACTTTCAAG 13981  CAG  TTCTCCAGCCGGCCCAGGTGTGGCAGAGACATAAGCCCTGTGGTGCTAG
       |||  |||||||| ||||||||||||||| ||||   || ||||| |||||
1148   CAG  CAGCTCTTCCCCACCAGGCCCCAGTGTGGCAGGACAAACTCCATTGCTAG
```

Matches = 128     Mismatches = 33     Unmatched = 9
Length = 170      Matches/Length = 75.3 Percent Top strand is SEQ ID NO: 27:;
Bottom strand is SEQ ID NO: 28:..

FIGURE 8

```
1    MetAspLeuLeuValSerSerGlyMetLysGlyIleAlaValPheLeuValPheIlePhe
     |   |   |   :       :       :           :   :               |
1    MetLysLeuLeuLeuLeuAlaAlaLeu    LeuThrAla    GlyVal    Thr

21   CysTrpThrThrSerThrLeuSerSerPheTrpGlnPheGlnArgMetValLys    His
         :   |   |   :           |   |   |       |   :   |
16   AlaHisSerIleSerThrArgAlaVal    TrpGlnPheArgAsnMetIleLysCysThr

40   IleThrGlyArgSerAlaPhePheSerTyrTyrGlyTyrGlyCysTyrCysGlyLeuGly
     |   |   |           |           |   |   |   |   |   |   |   |
35   IleProGlySerAspProLeuArgGluTyrAsnAsnTyrGlyCysTyrCysGlyLeuGly

60   GlyArgGlyIleProValAspAlaThrAspArgCysCysTrpAlaHisAspCysCysTyr
     |   |   |   |   |       |   |   |   :   |   |       |   |   |
55   GlySerGlyThrProValAspAspLeuAspArgCysCysGlnThrHisAspHisCysTyr

80   HisLysLeuLysGluTyrGly    CysGlnProIleLeu    AsnAlaTyr    Gln
     |       |   |                   |       :       |   |        :
75   AsnGlnAlaLysLysLeuGluSerCysLysPheLeuIleAspAsnProTyrThrAsnThr

96   PheAla    IleValAsnGlyThrValThrCysGlyCysThrMetGlyGlyGlyCysLeu
     :   :               |   |               |   |       |   :
95   TyrSerTyrLysCysSerGlyAsnValIleThr    CysSerAspLysAsnAsnAsp

115  CysGlyGlnLysAlaCysGluCysAspLysLeuSerValTyrCysPheLysGluAsnLeu
     |           |       |   |   |   :       :           |   |                :
113  CysGluSerPheIleCysAsnCysAspArgGlnAlaAlaIleCysPhe    SerLysVal

135  AlaThrTyrGluLysThrPheLysGlnLeuPheProThrArgProGlnCysGlyArgAsp
         |       |       :   |   |           |       |   :
132  Pro    TyrAsnLysGluTyrLysAspLeu    AspThrLys

155  LysLeuHisCys
     |       |   |
144  Lys    HisCys
```

Matches = 56         Mismatches = 84        Unmatched = 24
Length = 164         Matches/Length = 34.1 Percent Top line is RPLA2-8 deduced amino acid sequence; bottom line is rat type I PLA2 amino acid sequence. A vertical line indicates a match, : a conservative substitution, and no symbols a mismatch.

---

Top line is SEQ ID NO: 22:;

Bottom line is SEQ ID NO: 34:.

FIGURE 9

```
1    MetAspLeuLeuValSerSerGlyMetLysGlyIleAlaValPheLeuValPheIlePhe
     |  :  |  :        :        :  |  |  :  :        |
1    MetLysValLeuLeu      Leu     LeuAlaVal    ValIleMetAlaPhe

21   CysTrpThrThrSerThrLeuSerSerPheTrpGlnPheGlnArgMetValLysHisIle
              :              |           |        |  |  :
15   Gly    SerIleGlnValGlnGlySerLeuLeuGluPheGlyGlnMetIleLeuPheLys

41   ThrGly   ArgSerAlaPhePheSerTyr   TyrGlyTyrGlyCysTyrCysGlyLeu
     |  |     |  :        |  |     :     |  |  |     |  |  :
34   ThrGlyLysArgAlaAspVal    SerTyrGlyPhe   TyrGlyCysHisCysGlyVal

59   GlyGlyArgGlyIleProValAspAlaThrAspArgCysCysTrpAlaHisAspCysCys
     |  |  |  |  :  |  |  |  |  |  |  |  |  :  |  |  |  |
52   GlyGlyArgGlySerProLysAspAlaThrAspTrpCysCysValThrHisAspCysCys

79   TyrHisLysLeuLysGluTyrGlyCysGlnProIleLeuAsnAlaTyrGlnPheAlaIle
     |  :  |        |  |              :  |     |  :
72   TyrAsnArgLeuGluLysArgGlyCysGlyThrLysPheValThrTyrLysPheSerTyr

99   ValAsnGlyThrValThrCysGlyCysThrMetGlyGlyGlyCysLeuCysGlyGlnLys
     |     :  :  |                          |           |     |
92   ArgGlyGlyGlnIleSerCysSerThrAsn   GlnAspSerCysArg    LysGlnLeu

119  AlaCysGluCysAspLysLeuSerValTyrCysPheLysGluAsnLeuAlaThrTyrGlu
     |  |  |  :     |  |  |     |  |  |     |  :  |
110     CysGlnCysAspLysAlaAlaAlaGluCysPheAlaArgAsnLysLysSerTyrSer

139  LysThrPheLysGlnLeuPheProThrArgProGlnCys   GlyArgAspLysLeuHis
     :     |     :  |  :        :        |    |  :
129  LeuLysTyr   GlnPheTyrProAsnLys     PheCysLysGlyLysThrPro   Ser

158  Cys
     |
146  Cys
```

Matches = 56        Mismatches = 87        Unmatched = 18
Length = 161        Matches/Length = 34.8 Percent Top line is RPLA2-8 deduced amino acid sequence; bottom line is rat type II amino acid sequence. | indicates a match, : a conservative substitution, and no symbol, a mismatch.

---

Top line is SEQ ID NO: 22:;

Bottom line is SEQ ID NO: 35:.

FIGURE 11A

```
         10         20         30         40         50         60
GAATTCCGGTGGATGGAGGGGGCTGAGCAGGATGTTGACTGGCTATCGTTCATTGAGCAC
Clone linker
         70         80         90        100        110        120
TCTCACGATCAGCATCACGCACGGAATCCATCCTTCCTGTGTTGCAGCTTGTAGACCCTG
        130        140        150        160        170        180
ATGCTTGGGCTGCCAGCATAAACGTGGGGATCCAGACTCTGTCTACCGAGGCTGCCCATA
         gaattccggtccaggcctgtcctatgggcagcagcctcggtagacagagt....
         Clone linker
        190        200        210        220        230        240
GGGACAGGCCCTGGGAAGAGGAGCTGAGACCAGGCTAAAAAGAACCCAAGAAATGAAGCG
                                                     MetLysAr
        250        260        270        280        290        300
CCTCCTCACGCTGGCTTGGTTCCTGGCTTGCAGTGTGCCTGCAGTCCCAGGGGGCTTGCT
gLeuLeuThrLeuAlaTrpPheLeuAlaCysSerValProAlaValProGlyGlyLeuLe
Rclo10-5' (primer)
        310        320        330        340        350        360
AGAACTGAAGTCCATGATTGAGAAGGTGACTGGGAAGAATGCCGTAAAGAACTATGGCTT
uGluLeuLysSerMetIleGluLysValThrGlyLysAsnAlaValLysAsnTyrGlyPh
Rclo10-1 (primer)
        370        380        390        400        410        420
CTACGGCTGCTACTGTGGCTGGGGCGGCCACGGGACCCCTAAGGATGGCACTGATTGGTG
eTyrGlyCysTyrCysGlyTrpGlyGlyHisGlyThrProLysAspGlyThrAspTrpCy
                                     Rclo10-2 (primer)
        430        440        450        460        470        480
CTGTCGGATGCACGACCGTTGTTATGGGCTACTGGAGGAGAAACACTGTGCCATCCGGAC
sCysArgMetHisAspArgCysTyrGlyLeuLeuGluGluLysHisCysAlaIleArgTh
        490        500        510        520        530        540
CCAGTCCTATGACTACAGATTCACACAGGACTTAGTCATCTGCGAACACGACTCCTTCTG
rGlnSerTyrAspTyrArgPheThrGlnAspLeuValIleCysGluHisAspSerPheCy
        550        560        570        580        590        600
TCCAGTGAGGCTTTGTGCTTGTGACCGGAAGCTGGTCTACTGCCTGAGGAGAAACCTCTG
sProValArgLeuCysAlaCysAspArgLysLeuValTyrCysLeuArgArgAsnLeuTr
        610        610        630        640        650        660
GAGTTACAACCGTCTTTACCAGTATTACCCCAACTTCCTCTGCTAATGTCCTCTGTGGGC
pSerTyrAsnArgLeuTyrGlnTyrTyrProAsnPheLeuCysEnd
                                    Rclo10-3' (primer)
        670        680        690        700        710        720
TCTCGCCGGGAGTGCCTCCCACAGTGGCGGCCCCCTCGGCTGTATTCCTGATCCGTCCA
        730        740        750        760        770        780
CCCAAGGTCTTGGATCTGCCTTCCTCTGTGTACCACTGGGCTGGACAGAGCCCAGGGTTA
        790        800        810        820        830        840
CACCCTACCCTCCAGAATCCTAGAGAGGGACTCTGATGTAGAGTCTGCGGACTCTGGATA
```

RPLA-10 cDNA sequence corresponds to SEQ ID NO: 29: and Derived Amino Acid Sequence corresponds to SEQ ID NO: 30:.

FIGURE 11B

```
       850        860        870        880        890        900
GCTGAGCCTGCACTTGCAGAATTTGGCGCTGGGCCCCGGAGCTCCCTCAGCTCCAGGCCA
   910        920        930        940        950        960
GTGTCGTGTTGACTTTCCTTTCAATTTCTGGAACCCAACTGCCATTACCACCCTCCAGAG
       970        980        990       1000       1010       1020
ACCTCTTACTAGAGGAGAAGCCAAATTAACTCTATAAATCTGCCATGTAGCTATTAAATA
      1030       1040       1050       1060       1070       1080
AAACCCATTCACGAGGCGAGAAGAACACCACCCCAGCACTCCCTCTGACAGGGCTGGGGT
      1090       1100       1110       1120       1130       1140
AGGAGTGCCAATGCTTCTCTAACCCCTGAGGCATCTGTGCACCCTCTAGGATGGAGGTCA
      1150       1160       1170       1180       1190       1200
GGAAACAGGTGGGGGCCTTACATGCCTTTCATGGTTTGTCTTGAGTTTATTTTCTTAAAC
      1210       1220       1230       1240       1250       1260
CTTAGGGTCTTTCAAGCCAGACCTGGAGCTCAAGATTCTTCTGGAGGAAGGTGAGACACA
      1270       1280       1290       1300       1310       1320
GCCCTATGCCACCTTGAGCTCCAGGCTAGAAAGGGACAGCCCCTAGCCCTGGCTTCTGCA
      1330       1340       1350       1360       1370       1380
ACTGTGTGGTCTTGAACCTCCGTATAGTCCGAATCCCTCTGGCTCTCCTCAAAATATAAA
      1390       1400       1410       1420       1430       1440
ACAAGCCTCCTTCCAATAGCATATTGGTGCACACCCCTAATCCCATCACCTGGGAGGAGG
      1450       1460       1470       1480       1490       1500
AGGCGGCAGGAGCATCAGGAGTTCAAGGCCAGCTCCTGCCCCCTAGCAGGGATGGTAGGC
      1510       1520       1530       1540       1550       1560
TGCATGAGAGTGTGTCTCAGAAAGAACCACCTGGTGCGGGTACAGGGATGCTGGGATTCT
      1570       1580       1590       1600       1610       1620
GAGATGTCACTCAGTGCGGGAAAAGATTCAAGGAGGGGAACAGATCAATGGCAGAATGAC
      1630       1648       1650       1660       1670       1680
TGTCTGTGCCGAGTTAAGGGCACTGAAAATCTCAGCTCATCTATCGCTTTATAGAAGATA
      1690       1700       1710       1720       1730       1740
GAGCTTTGGGAGGAAGCAAGGCACTCTACAGTAAAGGAGTGGCCTTTCCAAGGAAGGGTC
                              Polyadenylation site
      1750       1760       1770       1780       1790       1800
TAGGCTCCTTCTTCTCCAGAACATGCACAGGACATAGGAGATCCATTATTTAGAGACCTT
      1810
TCGTGTTCGAACGTTTTCTCCGGAATTC----RPLA2-10-1
                     Clone linker
      ......aaataaagttaattatattgagccggaatcc----RPLA2-10-2
Additional Polyadenylation site.   Clone linker
```

FIGURE 11C

The top sequence comes from RPLA2-10-1.  The bottom sequence is from
RPLA-10-2.  Both the sequences are identical except for the 5' and 3'
sequences indicated by the lower case letters.

FIGURE 12

```
            10         20         30         40         50         60
     GGATACCAATGTTCCGACTGGAGACGGGGAGCCCGCGAGACCCGGGTCTCCAGGGTCTGC
            70         80         90        100        110        120
     CCAAGGAAGTTGCTCATGGGAGCAGACCCCTAGAGCAGGATTTGAGGCCAGGCCAAAGAG
           130        140        150        160        170        180
     AACCCCAGAGATGAAAGGCCTCCTCCCACTGGCTTGGTTCCTGGCTTGTAGTGTGCCTGC
               MetLysGlyLeuLeuProLeuAlaTrpPheLeuAlaCysSerValProAl
      Hclo10-5' (primer)             Hclo10-A (primer)
      Clone HPLA2-10-5-----CCTCC....
           190        200        210        220        230        240
     TGTGCAAGGAGGCTTGCTGGACCTAAAATCAATGATCGAGAAGGTGACAGGGAAGAACGC
     aValGlnGlyGlyLeuLeuAspLeuLysSerMetIleGluLysValThrGlyLysAsnAl
           Clo10-1 (primer)              Clone HPLA2-10-7----AACGC....
           250        260        270        280        290        300
     CCTGACAAACTACGGCTTCTACGGCTGTTACTGCGGCTGGGGCGGCCGAGGAACCCCCAA
     aLeuThrAsnTyrGlyPheTyrlyCysTyrCysGlyTrpGlyGlyArgGlyThrProLy
           310        320        330        340        350        360
     GGATGGCACCGATTGGTGCTGTTGGGCGCATGACCACTGCTATGGGCGGCTGGAGGAGAA
     sAspGlyThrAspTrpCysCysTrpAlaHisAspHisCysTyrGlyArgLeuGluGlyLy
      Clo10-1a (primer)
           370        380        390        400        410        420
     GGGCTGCAACATTCGCACACAGTCCTACAAATACAGATTCGCGTGGGGCGTGGTCACCTG
     sGlyCysAsnIleArgThrGlnSerTyrLysTyrArgPheAlaTrpGlyValValThrCy
           430        440        450        460        470        480
     CGAGCCCGGGCCCTTCTGCCATGTGAACCTCTGTGCCTGTGACCGGAAGCTCGTCTACTG
     sGluProGlyProPheCysHisValAsnLeuCysAlaCysAspArgLysLeuValTyrCy
           490        500        510        520        530        540
     CCTCAAGAGAAACCTACGGAGCTACAACCCACAGTACCAATACTTTCCCAACATCCTCTG
     sLeuLysArgAsnLeuArgSerTyrAsnProGlnTyrGlnTyrPheProAsnIleLeuCy
                                                      Hclo10-C (primer)
           550        560        570        580        590        600
     CTCCTAGGCCTCCCCAGCGAGCTCCTCCCAGACCAAGACTTTTGTTCTGTTTTTCTACAA
     sSerEnd
     Hclo10-3' (primer)
           610        620        630        640        650        660
     CACAGAGTACTGACTCTGCCTGGTTCCTGAGAGAGGCTCCTAAGTCACAGACCTCAGTCT
           670        680        690        700        710        720
     TTCTCGAAGCTTGGCGGACCCCCAGGGCCACACTGTACCCTCCAGCGAGTCCCAGGGGAG
           730        740        750        760        770        780
     TGACTCTGGTCATAGGACTTGGTAGGGTCCCAGGGTCCCTAGGCCTCCACTTCTGAGGGC
           790        800        810        820        830        840
     AGCCCCTCTGGTGCCAAGAGCTCTCCTCCAACTCAGGGTTGGCTGTGTCTCTTTTCTTCT
           850        860        870        880        890        900
     CTGAAGACAGCGTCCTGGCTCCAGTTGGAACACTTTCCTGAGATGCACTTACTTCTCAGC
           910        920        930        940        950        960
     TTCTGCGATCAGATTATCATCACCACCACCCTCCAGAGAATTTTACGCAAGAAGAGCCAA
           970        980        990       1000       1010
     ATTGACTCTCTAAATCTGGTGTATGGGTATTAAATAAAATTCATTCTCAAGGCT
                            Polyadenylation site
                                                 .....AATAAA
                                                      Additional
     AACCACATTGGCATTTTC----HPLA2-10-3
     Polyadenylation site
```

HPLA2-10 cDNA sequence corresponds to SEQ ID NO: 31: and Derived Amino Acid sequence corresponds to SEQ ID NO: 32:.

FIGURE 13

```
1    MetLysGlyLeuLeuProLeuAlaTrpPheLeuAlaCysSerValProAlaValGlnGly
     |  |  |  |  |  |  |  |  |  |  |  |  |  |  |  |  |  |  |  |
1    MetLysArgLeuLeuThrLeuAlaTrpPheLeuAlaCysSerValProAlaValProGly

21   GlyLeuLeuAspLeuLysSerMetIleGluLysValThrGlyLysAsnAlaLeuThrAsn
     |  |  |  :  |  |  |  |  |  |  |  |  |  |  |  |  |  :     |
21   GlyLeuLeuGluLeuLysSerMetIleGluLysValThrGlyLysAsnAlaValLysAsn

41   TyrGlyPheTyrGlyCysTyrCysGlyTrpGlyGlyArgGlyThrProLysAspGlyThr
     |  |  |  |  |  |  |  |  |  |  |  |  :  |  |  |  |  |  |  |
41   TyrGlyPheTyrGlyCysTyrCysGlyTrpGlyGlyHisGlyThrProLysAspGlyThr

61   AspTrpCysCysTrpAlaHisAspHisCysTyrGlyArgLeuGluGluLysGlyCysAsn
     |  |  |  |     |  |  :  |  |  |  |     |  |  |  |     |
61   AspTrpCysCysArgMetHisAspArgCysTyrGlyLeuLeuGluGluLysHisCysAla

81   IleArgThrGlnSerTyrLysTyrArgPheAlaTrpGlyValValThrCysGluProGly
     |  |  |  |  |  |     |  |  |  :        :  |     |  |  |
81   IleArgThrGlnSerTyrAspTyrArgPheThrGlnAspLeuValIleCysGluHisAsp

101  ProPheCysHisValAsnLeuCysAlaCysAspArgLysLeuValTyrCysLeuLysArg
     |  |  |     |     |  |  |  |  |  |  |  |  |  |  |  |  :  |
101  SerPheCysProValArgLeuCysAlaCysAspArgLysLeuValTyrCysLeuArgArg

121  AsnLeuArgSerTyrAsnProGlnTyrGlnTyrPheProAsnIleLeuCysSer
     |  |     |  |  |  |     |  |  |  :  |  |     |  |
121  AsnLeuTrpSerTyrAsnArgLeuTyrGlnTyrTyrProAsnPheLeuCys
```

Matches = 107    Mismatches = 30           Unmatched = 1
Length = 138     Matches/Length = 77.5 Percent Top and bottom lines are deduced amino acid sequences of HPLA2-10 and RPLA2-10, respectively.

Top line is SEQ ID NO: 32:;

Bottom is SEQ ID NO: 30:.

FIGURE 14

```
1    MetLysGlyLeuLeuProLeuAlaTrpPheLeuAlaCysSerValProAlaValGln
     | |       | |       | |       |       :       :
1    MetLys   LeuLeuValLeuAlaValLeuLeuThrValAlaAlaAlaAspSerGlyIle

20   GlyGly   LeuLeu   AspLeuLysSerMetIleGlu   LysValThrGlyLysAsn
     :                         | |             :           |
20   SerProArgAlaValTrpGlnPheArgLysMetIleLysCysValIleProGlySerAsp

37   AlaLeuThrAsnTyrGlyPheTyrGlyCysTyrCysGlyTrpGlyGlyArgGlyThrPro
              |       |       | | | | | |       | |       | | |
40   ProPheLeuGluTyrAsnAsnTyrGlyCysTyrCysGlyLeuGlyGlySerGlyThrPro

57   LysAspGlyThrAspTrpCysCysTrpAlaHisAspHisCysTyrGlyArgLeuGluGlu
        |  |        |  |  |  :  |  |     |  |
60   ValAspGluLeuAspLysCysCysGlnThrHisAspAsnCysTyrAspGlnAlaLysLys

77       LysGlyCysAsn    IleArgThrGlnSerTyrLysTyrArgPheAlaTrp
            |     :      :       |          :  :  :
80   LeuAspSerCysLysPheLeuLeuAspAsnProTyrThrHisThrTyrSerTyrSerCys

93       GlyVal    ValThrCysGluProGlyProPhe    CysHisValAsnLeuCysAla
             |     :  | |                      |              :  |
100  SerGlySerAlaIleThrCysSerSerLysAsnLysGluCysGluAlaPheIleCysAsn

110  CysAspArgLysLeuValTyrCysLeuLysArgAsnLeuArgSerTyrAsnProGlnTyr
     | | |              |            :                   | |
120  CysAspArgAsnAlaAlaIleCysPheSerLysAla       ProTyrAsnLysAlaHis

130  GlnTyrPheProAsnIleLeu    Cys    Ser
                               |      |
138  LysAsnLeuAspThrLysLysTyrCysGlnSer
```

Matches = 45        Mismatches = 90        Unmatched = 16
Length = 151        Matches/Length = 29.8 Percent Top line is deduced amino acid sequence; bottom line is human type I amino acid sequence.

---

Top line is SEQ ID NO: 32:;

Bottom is SEQ ID NO: 36:.

FIGURE 15

```
  1   MetLysGlyLeuLeuProLeuAlaTrpPheLeuAlaCysSerValProAlaValGlnGly
      |  |     |  |     |  |        :              :           |
  1   MetLysThrLeuLeuLeuAlaValIleMetIlePheGlyLeuLeuGlnAlaHisGly

21   GlyLeuLeuAspLeuLysSerMetIleGluLysValThrGlyLysAsnAlaLeuThrAsn
      |  :     :        |  |        |  |  |  |        |
 21   AsnLeuValAsnPheHisArgMetIleLysLeuThrThrGlyLysGluAlaAlaLeuSer

41   TyrGlyPheTyrGlyCysTyrCysGlyTrpGlyGlyArgGlyThrProLysAspGlyThr
      |  |  |  |  |  |     |  |  |  |  |  |  |     :  |  |  |  |
 41   TyrGlyPheTyrGlyCysHisCysGlyValGlyGlyArgGlySerProLysAspAlaThr

61   AspTrpCysCysTrpAlaHisAspHisCysTyrGlyArgLeuGluGluLysGlyCysAsn
      |     |  |  :     |  |     |  |  |     |  |  |     :  |  |
 61   AspArgCysCysValThrHisAspCysCysTyrLysArgLeuGluLysArgGlyCysGly

81   IleArgThrGlnSerTyrLysTyrArgPheAlaTrpGlyVal   ValThrCysGluPro
      :        |  |  |     :        :        |    :     |  |
 81   ThrLysPheLeuSerTyrLysPheSerAsnSer   GlySerArgIleThrCysAlaLys

100   GlyProPheCysHisValAsnLeuCysAlaCysAspArgLysLeuValTyrCysLeuLys
      |     :     :     |  |     |  |     :              |     |
100   GlnAspSerCysArgSerGlnLeuCysGluCysAspLysAlaAlaAlaThrCysPheAla

120   ArgAsnLeuArgSerTyrAsnProGlnTyrGlnTyrPheProAsnIleLeuCys   Ser
      |  |     :     |  |     |  |  |     :        |           |
120   ArgAsnLysThrThrTyrAsnLysLysTyrGlnTyrTyrSerAsnLysHisCysArgGly

140   SerThrProArgCys
```

Matches = 63        Mismatches = 74        Unmatched = 8
Length = 145        Matches/Length = 43.4 Percent Top line is HPLA2-10 deduced amino acid sequence; bottom line is human PLA2 type II amino acid sequence.

---

Top line is SEQ ID NO: 32:;

Bottom is SEQ ID NO: 37:.

FIGURE 16

```
  1    MetLysArgLeuLeuThrLeuAlaTrpPheLeuAlaCys    SerValProAlaValPro
        |   |       |   |       |   |         :                   |
  1    MetLysValLeuLeuLeuAlaValValIleMetAlaPheGlySerIleGlnValGln

20    GlyGlyLeuLeuGluLeuLysSerMetIleGluLysValThrGlyLysAsnAlaValLys
        |   |   |   |           |   |           |   |   |   |   |
 21    GlySerLeuLeuGluPheGlyGlnMetIleLeuPheLysThrGlyLysArgAlaAspVal

40    AsnTyrGlyPheTyrGlyCysTyrCysGlyTrpGlyGlyHisGlyThrProLysAspGly
        |   |   |   |   |   |   |   |   |   |   :   |   :   |   |   |
 41    SerTyrGlyPheTyrGlyCysHisCysGlyValGlyGlyArgGlySerProLysAspAla

60    ThrAspTrpCysCysArgMetHisAspArgCysTyrGlyLeuLeuGluGluLysHisCys
        |   |   |   |   |       |   |       |   |           |   |   :   |
 61    ThrAspTrpCysCysValThrHisAspCysCysTyrAsnArgLeuGluLysArgGlyCys

80    AlaIleArgThrGlnSerTyrAspTyrArgPheThrGlnAspLeuValIleCysGlu
        :       :       |   :               :           :       |
 81    GlyThrLysPheValThrTyrLysPheSerTyrArgGlyGlyGlnIleSerCysSerThr

99    HisAspSerPheCysProValArgLeuCysAlaCysAspArgLysLeuValTyrCysLeu
        |           |               |   |   |   :               |
101    AsnGlnAspSerCysArgLysGlnLeuCysGlnCysAspLysAlaAlaAlaGluCysPhe

119    ArgArgAsnLeuTrpSerTyrAsnArgLeuTyrGlnTyrTyrProAsn    Phe
        |   |       |   |           |   |   :   |   |   |           |
121    AlaArgAsnLysLysSerTyrSerLeuLysTyrGlnPheTyrProAsnLysPheCysLys

136        Leu        Cys
                       |
141    GlyLysThrProSerCys
```

Matches = 62         Mismatches = 75         Unmatched = 9
Length = 146         Matches/Length = 42.5 Percent Top line is RPLA2-10 deduced amino acid sequence; bottom line is rat PLA2 type II amino acid sequence.

---

Top line is SEQ ID NO: 30:;

Bottom line is SEQ ID NO: 35:.

FIGURE 17

```
  1    MetLysArgLeuLeuThr     Leu    Ala         Trp      PheLeuAla
       |  |  |   :  :          :      :           :       |  |  |
  1    MetAspLeuLeuValSerSerGlyMetLysGlyIleAlaValPheLeuValPheIlePhe

13    Cys    SerValProAlaValProGlyGlyLeuLeuGluLeuLysSerMetIleGluLys
       |       :        :   :                                |  :   :
 21    CysTrpThrThrSerThrLeu   SerSerPheTrpGlnPheGlnArgMetValLysHis

32    ValThrGlyLysAsnAlaValLysAsnTyrGlyPhe   TyrGlyCysTyrCysGlyTrp
       :  |  |  :   |           |  :          |  |  |  |  |  |  |
 40    IleThrGlyArgSerAlaPhePheSerTyr   TyrGlyTyrGlyCysTyrCysGlyLeu

51    GlyGlyHisGlyThrProLysAspGlyThrAspTrpCysCysArgMetHisAspArgCys
       |  |   :   |  |  |  |  |  |  |  |  |  |  |      |  |   |  |
 59    GlyGlyArgGlyIleProValAspAlaThrAspArgCysCysTrpAlaHisAspCysCys

71    TyrGlyLeuLeuGluGluLysHisCysAlaIleArgThrGlnSerTyrAspTyrArgPhe
       |      |   |  |   |                :   :   |           :
 79    TyrHisLysLeuLysGluTyrGlyCysGlnProIleLeuAsnAlaTyrGlnPheAlaIle

91    ThrGlnAspLeuValIleCysClu    His    AspSer     PheCysProValArg
        :                |  |                                |     :
 99    ValAsnGlyThrValThrCysGlyCysThrMetGlyGlyGlyCysLeuCysGlyGlnLys

107    LeuCysAlaCysAspArgLysLeuValTyrCysLeuArgArgAsnLeuTrpSerTyrAsn
       |  |   |  |   :      |  |  |   :       |  |       :   |
119    AlaCysGluCysAspLysLeuSerValTyrCysPheLysGluAsnLeuAlaThrTyrGlu

127    ArgLeuTyr   GlnTyrTyrProAsnPhe                       Leu  Cys
        :    :      |   :   |                                |    |
139    LysThrPheLysGlnLeuPheProThrArgProGlnCysGlyArgAspLysLeuHisCys
```

Matches = 48          Mismatches = 87         Unmatched = 25
Length = 160          Matches/Length = 30.0 Percent Top line is RPLA2-10 deduced amino acid sequence; bottom line is PLA2-8 deduced amino acid sequence.

---

Top line is SEQ ID NO: 30:;

Bottom line is SEQ ID NO: 22:.

FIGURE 18

```
1    MetLysArgLeuLeuThrLeuAlaTrpPheLeuAlaCysSerVal    Pro    AlaVal
     | |         |         | |         | :          |            : :
1    MetLys    LeuLeuLeuLeuAlaAlaLeuLeuThrAlaGlyValThrAlaHisSerIle

19   ProGly    GlyLeuLeuGluLeuLysSerMetIleGlu    LysValThrGlyLysAsn
             :           | |     :        |
20   SerThrArgAlaValTrpGlnPheArgAsnMetIleLysCysThrIleProGlySerAsp

37   AlaValLysAsnTyrGlyPheTyrGlyCysTyrCysGlyTrpGlyGlyHisGlyThrPro
     : :         |     | | | | | | |     | |    | | |
40   ProLeuArgGluTyrAsnAsnTyrGlyCysTyrCysGlyLeuGlyGlySerGlyThrPro

57   LysAspGlyThrAspTrpCysCysArgMetHisAspArgCysTyrGlyLeuLeuGluGlu
     |  |        |  |        | |         | | :   | |
60   ValAspAspLeuAspArgCysCysGlnThrHisAspHisCysTyrAsnGlnAlaLysLys

77      LysHisCysAla    IleArgThrGlnSerTyr    Asp    TyrArgPhe
         |          :                   |                  :
80   LeuGluSerCysLysPheLeuIleAspAsnProTyrThrAsnThrTyrSerTyrLysCys

91   ThrGlnAspLeuValIleCys    GluHisAspSerPheCysProValArgLeuCysAla
     :        :       | : :                    |              : |
100  SerGlyAsnValIleThrCysSerAspLysAsnAsnAspCysGluSerPheIleCysAsn

110  CysAspArgLysLeuValTyrCysLeuArgArgAsnLeuTrpSerTyrAsnArgLeuTyr
     | | |              |     :         :           | | :      |
120  CysAspArgGlnAlaAlaIleCysPheSerLys    Val    ProTyrAsnLysGluTyr

130       GlnTyrTyrProAsnPheLeuCys
                                 |
138  LysAspLeuAspThrLysLysHisCys
```

Matches = 45        Mismatches = 89        Unmatched = 15
Length = 149        Matches/Length = 30.2 Percent Top line is RPLA2-10 deduced amino acid sequence; bottom line is rat PLA2 type I amino acid sequence.

---

Top line is SEQ ID NO: 30:;

Bottom line is SEQ ID NO: 34:.

FIGURE 19A

SEQ ID NO: 33:

```
          10         20         30         40         50         60
  AAGCTTTGTG GGATTTCTAT TATGAACAAC ATAGGTGCCT TTCCAACTGG GGAACAGAGG 70         80         90        100        110        120
  AAATATGGAC TCCTCAAAAG AAAAAAAGAA GAGATGAAGG GATGATGTTG CCAAAGAAAG 130        140        150        160        170        180
  AAATTTGGAA AAAAAAAAAC CAAACCAACA TTTGCACTTT CAAAACCATG GAACCCTTCT 190        200        210        220        230        240
  TATTTTTATA TGTTCAGATC TAAATGCCAG AAAGGTTACC ACATTCAAAG GAATGAGAT 250        260        270        280        290        300
  TTGAAAATGA TTTCTTTGAG TCCTCTGCTG AGGTCTTTCC AAGGCACTAC AATTAGGGCT 310        320        330        340        350        360
  TTGCACCCAA ATACCCTTGC CTCATTTTGG TCATTTTTGT CCTGGAACAG AGGTTCAGCT 370        380        390        400        410        420
  GGGAGACCCC TCACACACAG GTGAAGGCGT GGCTGTAGAA CCTCAGACCC CCTGGTCTCC
                                                Exon 1 ?

430        440        450        460        470        480
  TCAGGAATGA AGGTCATTGC CATCCTCACC CTCCTCCTCT TCTGCTGTAA GTAGAGAGCG 490        500        510        520        530        540
  TTGGTGGGTC AGCACCAAGC TTCTGTCTTC CTGTTTATGT CAGTGGGAGG GGGGACTCTC 550        560        570        580        590        600
  CAGGTGGCAC CAGGTGAGGG AAGTCACAAG TCCCGCAGAA AAGAATCAGG AAAGGAACGG 610        620        630        640        650        660
  GCTCCCACCA ACGTCCTCTT GCTTCTGTTT CTGCTATAAA ATGGGCTGAT CCCAGTGTTG 670        680        690        700        710        720
  GGATCTTATA AAGTGTCTAG GAAATCAGAG GTTGCCAACC ATTTGCTAGA AAGGGAGTTT 730        740        750        760        770        780
  GAGTAGTATT TTACCCCCCC TCACCCTCAA GAGTCTTTTT ACTTTGGATG CTAGTAGCCT 790        800        810        820        830        840
  TTTATTTAGG CATTGGATCA GAACAAAAAT GCAGGACATA TATCCAGCCT AATTTAACCA 850        860        870        880        890        900
  ATGGATTAAA TGGCCTTATC AGGAAAAGAC CATTTTATGG TGACTTATGG GATAATTGGT 910        920        930        940        950        960
  AGTTATAAGT CATTGCTGCC GGGAGATCCG ATTGCTTACC TCTGCAAAGT GAAGAAAGAC 970        980        990       1000       1010       1020
  CTACTGGGAA ACAGTTTGGG GTCTACTGGA GACTGATAGA CTCTTTTGCT GGATTCGTTG
```

FIGURE 19B

```
           1030       1040       1050       1060       1070       1080
     AGTGGAGGTT TCTCCAGATC CATTTTCCTG TCTCTTTCAA TTGAGTCACA ATAACTTTTG 1090       1100       1110       1120       1130       1140
     AGTCCCTAAG TCAAAGATGT CAAAAACAGA CTTCCTTTCC CCACAGTGAG TGGTGGAATT 1150       1160       1170       1180       1190       1200
     TACACTTTGC AAGGTGATAG TGCAGGAGGA TACCTGTACG CAGGGATGAC CGCCTCTGCA 1210       1220       1230       1240       1250       1260
     GCCCTCAGTG CGGCTCCAGG ACTGCTTGGG CACCAGTGAC CGCCCCATGG GTTTCTTCCG 1270       1280       1290       1300       1310       1320
     CCACACCCCC GTTTAGACTG AACACGATAG GTAGATCGAA GGCCACCTGA GAAAACTCCC 1330       1340       1350       1360       1370       1380
     CCAAAACTCT ATTTCTGTTT CTCTTCTTCA AAGTTCATGT CTTTGTTGTA TTTTTATTGC 1390       1400       1410       1420       1430       1440
     AAATTTACTA CATGCTTATA GTTAAAAAGT AAAATAAATG AGTATATAGC AACAAGGTAA 1450       1460       1470       1480       1490       1500
     AGCTCCTCCT CATCCTCCCC AGACCCCAGT TTTTTCCCTA CATCCAGATG TGACCACTCT 1510       1520       1530       1540       1550       1560
     TAAGAGTTTG ATATACATCC TCTATACAGC GTTTACCACA CACACATTCA AAACACCATA 1570       1580       1590       1600       1610       1620
     ATAGGAAGGG AACACATGCT GGGCCGGGCG CGGTTGTTCA TGACTATAAT CCCAGCACTT 1630       1640       1650       1660       1670       1680
     TGGGAGGCCG AGGCGGGCGG ATCACCTGAG GTCAGGAGTT CGAGACCAGC CTGGCCAGCT 1690       1700       1710       1720       1730       1740
     GGCAACATGG TGAAACCCGT CTCTATTAAA AATACAAAAA ATTAGTCAAG CATGGCAGTT 1750       1760       1770       1780       1790       1800
     GGGCACCTGT AATCCCAGCT ACTCAGGAGG CTGAGGCAGG AGAATTGCCT GAACCCGGGA 1810       1820       1830       1840       1850       1860
     GGCGGAGGTT GCAGTGAGCC GAGATCACAC CATTGCACTC CAGCCTGGGT AACAACAGCG 1870       1880       1890       1900       1910       1920
     AAACTCCGTC TCAAAAAAAA AAAAAAAAGA AGGAAAGGGA CACACGCTTA TTATGAAAGA 1930       1940       1950       1960       1970       1980
     CATGAGACAG CGGAGACGTG TATAAATGAT GTTGCCTGTT TCTTTCTCT CTCTTCATCC 1990      12000       2010       2020       2030       2040
     ATGCTAGAGA TAGTGCTATC AAATGTAGTT ATTTTGAGA CACATATTTC GTATTATCCC
```

FIGURE 19C

```
         2050        2060        2070        2080        2090        2100
   TGTCGTGACA  TGTGGGTGGT  TTCCAATTTT  TTGATATCAC  AGATAATGCT  TCAGGAAACC 2110        2120        2130        2140        2150        2160
   ATTTTGTGTA  TCGATTTGTG  CCCACTCTCA  TAAGCATCTT  GTAGAAGCAA  AAACAGCTGA 2170        2180        2190        2200        2210        2220
   GTTCATGTGT  ACTTGTCATT  TAAAAAAATA  ATAATTGAGG  ATACCTTTCC  TGCCTCTTAA 2230        2240        2250        2260        2270        2280
   GTATTTTGTT  TCTCCTGTGA  GATAGTAAAG  GCCTGATGAC  ATCTGGAGGG  ACTGGCGTTT 2290        2300        2310        2320        2330        2340
   CTGGCTTTGA  ACTTTTGCCA  TTCATGTTGC  ATCAGACCCG  AGGGTGTTCT  GCCTAGAACT 2350        2360        2370        2380        2390        2400
   GTGGTTTCTT  GCTTTGAGGG  GGAAGACTAT  GGTTGATGGG  AAAGCCTTGT  TCTGAACCTC 2410        2420        2430        2440        2450        2460
   ATGGAAACTG  GGTATTCATC  TGGGTTAGCA  AAAAACTAGC  TGTGTTACAG  GGGCAAATCT 2470        2480        2490        2500        2510        2520
   GAACCTATTT  TATTCCCCAG  GAAAGAGGCT  GGTGATTCCA  GCCATGCCCC  TTGCACTTCG 2530        2540        2550        2560        2570        2580
   CTTTGGGGAT  CTGGTGATAT  TTCGAATGCT  CAGCACTCTA  GTAAGGGGAG  GGGACATCAA 2590        2600        2610        2620        2630        2640
   GGCAGCATCA  TGCTCATTGC  AACTTCCTTC  TTCCTTTTTT  TCTCATCGGT  GGTGGCAGCC
                                                                     ‾‾‾‾‾‾‾

2650        2660        2670        2680        2690        2700
   CCCACCCACA  GCAGTTTCTG  GCAGTTTCAG  AGGAGGGTCA  AACACATCAC  GGGGCGAAGT
   ‾‾‾‾‾‾‾‾‾‾  ‾‾‾‾‾‾‾‾‾‾  ‾‾‾‾‾‾‾‾‾‾  ‾‾‾‾‾‾‾‾‾‾  ‾‾‾‾‾‾‾‾‾‾  ‾‾‾‾‾‾‾‾‾‾

2710        2720        2730        2740        2750        2760
   GCCTTCTTCT  CATATTACGG  ATATGGCTGC  TACTGTGGGC  TTGGGGATAA  AGGGATCCCC
   ‾‾‾‾‾‾‾‾‾‾  ‾‾‾‾‾‾‾‾‾‾  ‾‾‾‾‾‾‾‾‾‾  ‾‾‾‾‾‾‾‾‾‾  ‾‾‾‾‾‾‾‾‾‾  ‾‾‾‾‾‾‾‾‾‾
   Exon 2

2770        2780        2790        2800        2810        2820
   GTGGATGACA  CTGACAGGTG  GGTGCAGAGG  CTCTAAGGCC  ACTTATCATT  TGTTTTGCAT
   ‾‾‾‾‾‾‾‾‾‾  ‾‾‾‾‾‾‾‾‾

2830        2840        2850        2860        2870        2880
   TAAAGTTCAT  GCTCAAAGCC  AGAGAGAGGG  TCTTAGGATT  CTTGCCTGGC  AAATAACAGA 2890        2900        2910        2920        2930        2940
   AAACAACTCA  GGCTAATGGA  AGGAAGAACT  GAACGGGATT  TGGAGGATGG  GTCTTGAGAA 2950        2960        2970        2980        2990        3000
   ACCCAGGGTC  GGGGCCAGCT  TCTTGAGTGT  GTGACCTGTG  AAGTTTCACA  GGGCCCAACA 3010        3020        3030        3040        3050        3060
   CTCATAAGGG  TCAGGGCCAG  CTTCTTGAGC  GTGTGATCTG  TAAAGTTCA   CAGGGCCTGG
```

FIGURE 19D

```
           3070       3080       3090       3100       3110       3120
      CACTCATAAC CCCCTAAACA TGGTTTACTG CTCTGCTGCC ACATCTTGAA ATTCTTAATA 3130       3140       3150       3160       3170       3180
      AAGGGCCTCA TGTTTTCATT TTGCTTTACT CTCTGCAATT ATGCCGTTGG TCCTGCCCAG 3190       3200       3210       3220       3230       3240
      AGCTCTAGAA GCTGTTTCAT CCTCATAGTA AAAGTGCTCT GCTTTCAGCT CTCCAGCTTT 3250       3260       3270       3280       3290       3300
      TAGCACTATA CCCACAGCAC AACTGACTCA CTAGTCCTAA TTCCATATTC TGGAGAGGGC 3310       3320       3330       3340       3350       3360
      TCCAAAGTGG CCCACTTTGG AGAAGTTGTC CATCTGGGTG AGGTTGCATG GCACAAACCT 3370       3380       3390       3400       3410       3420
      GGCTTCAGGC CTACTCCAAA GGATGGGGGT GGGGGAGTGT GAGTTCCTAG AAAAAGTAGA 3430       3440       3450       3460       3470       3480
      GGTGGGTGTC ATCTGGTGAA TGTACGTGTG GGGAGGTAAG AAACGGGACA GTTTGCGTCT 3490       3500       3510       3520       3530       3540
      CAATTCATTT GAAGACATAA GAAAGCAAAA TGTTCCTTGC CACATTTAAG GTAGTATGGA 3550       3560       3570       3580       3590       3600
      GAAACATGTC CCACAGTGGC CTTAAATATC ACTCTGAGCT CGAGTCTTGT GGTGGCTCAT 3610       3620       3630       3640       3650       3660
      GAACCATGGA GGACCTAGAG GTTCGAAGGG CAATTGACGC TTATCAAATG CCCTTATGTG 3670       3680       3690       3700       3710       3720
      CCAAGCACTG GGACTGGCCG ATTGGCATAC AAACCTAATT TAATTCTCGC AGGGAATGCA 3730       3740       3750       3760       3770       3780
      CGACACAGTT GATACCAGCC CATTTGACAG CCTGAGGACA TGTGAGTTGC TAAACCACCT 3790       3800       3810       3820       3830       3840
      CCTAAAGGCA ATGCAGCTTC TAAGTGGCAG AGTTTAGGAT TGAACGAGAA TTTGCCTATT 3850       3860       3870       3880       3890       3900
      TCAAAGTTTG TCCCCTCTCC TTGATGGTCT GTGCCTCCCC TGTCAAAGTC CAAAGGCTGA 3910       3920       3930       3940       3950       3960
      TTAGAAATTG AACATCATTA GCCAAAGCTG ATCAACAGCA GAGCCCCCAC TTGCAGATGG 3970       3980       3990       4000       4010       4020
      GAATGGTGAG AGAGGGAGAC TGAAACACTT TTTTCTTGGC CTTTCAGGGT TTAGAATCCA 4030       4040       4050       4060       4070       4080
      AGCTTAAGTT TCTGCCTTCC TGTCCCTTGT GTAGTGGTTG AGGACATGGA CTGAGCCCAT
```

FIGURE 19E

```
          4090       4100       4110       4120       4130       4140
     GCTCCAGATG GTATTTCTCC TCCAGTGCTC TCCCATCCAG CCCCCAGCCA ACTCTGGGTG 4150       4160       4170       4180       4190       4200
     CCATGAATGG GACTACGTCG GCTTTTACAG ACAGTTGTCT CCTCAGAGAC CGTTACAGTG 4210       4220       4230       4240       4250       4260
     CCTGACTCAC AGTAGGTGCT CAGTAAAAAG TGTTAAATGA ATGAATGGGC CTAGGTTTGT 4270       4280       4290       4300       4310       4320
     GTCCTGGGTC TATCATTCTC CAGCTGCCTA AGTTTGGGAA ATTGGCCTCT TGGAATCTCA 4330       4340       4350       4360       4370       4360
     GTCCCTCCCC TACAAAGGG CAGCAATGAT TGTACTTTAT AGTTTCTAGT AGCTAATGAG 4390       4400       4410       4420       4430       4440
     ATAGCAACAG ATACTACAGA GGGCTCAGGA AATGCTACTG GTTATTATTA TTATTTTTA 4450       4460       4470       4480       4490       4500
     TTTTATTTAT TTTTTGGGAG ACGGGGTCTT GCTCTATTAT CCAGGCCTGG GGTGGAGAGG 4510       4520       4530       4540       4550       4560
     CTCAATCAGA GCTCACTGCA GGTCCTCAAG CAATCCACCC ACTTCACCTC CTGAGTAGCC 4570       4580       4590       4600       4610       4620
     GGGACCACAG GCTGGTGCCA CCATGCCTGG CTTTTTTTTT TTTTTTAAAC TTAAAAAACA 4630       4640       4650       4660       4670       4680
     TAGGCGGCTC CCTATGTTGC CCAGGCTGGT CTCAAACTCC TGGACTGAAG CGATCCTCCT 4690       4700       4710       4720       4730       4740
     GCCTTATCCT CACAAAGTGC TGGGATTGCA GGCATGAGCC ACCACACCTG GCCTATGTTT 4750       4760       4770       4780       4790       4800
     AATATTATTG ATAATTCACC TCCTCACCTT CAATGCCTTC TTGCCTAGAG GAGGAGGCAG 4810       4820       4830       4840       4850       4860
     GTGAGCCCTT TCTAGTCCCC AGATAAGGTC CTCCAGCAGA TTCCTGAGGG ACCCACTTCC 4870       4880       4890       4900       4910       4920
     AGGCACAGCC CCTCATCTCC CTCTCCCTAC GAGAAGCTGA AGGAGTTCAG CTGCCAGCCT 4930       4940       4950       4960       4970       4980
     GTGTTGAACA GCTACCAGTT CCACATCGTC AATGGCGCAG TGGTTTGTGA GTAGCCTTTT 4990       5000       5010       5020       5030       5040
     CTGTATGGAA ATGTCTTTTA ACCTGGGCCT TTCCTTAACG TTCACCTCCT CTTTGACCCA 5050       5060       5070       5080       5090       5100
     GAGATCTTTT AGAAAATGAA ATGCTTCCAA GTGCTTGGAA GGAGATATTC CTGAGCTTTC
```

FIGURE 19F

```
       5110       5120       5130       5140       5150       5160
   TCCTGATGCT CCAGAGCTTC TCAGAGTGTC CGTGCTCATC CTGCCCTGGT CTCTCCCACC 5170       5180       5190       5200       5210       5220
   CATGAGTGTA CCTCCTGAAC TCTCTGGGGG CCCAGAGCCT GGCAGATAGT ACATGCTCAG 5230       5240       5250       5260       5270       5280
   TAAATACTTG TTCACTTGAG CTAATCTTGA AGCTTCCCTT GACAACTGCT GCTGTTGAGA 5290       5300       5310       5320       5330       5340
   ACATGTTTCC TTGTTTCTGT GATTTTGTTA ACAAAACGGC TCAGCTGTCT TCCAGTTGGA 5350       5360       5370       5380       5390       5400
   CAAATATTTA TTAAGGGCGA CTGCATGCCA AGCACTAAGA TAGGTGCTGC CAGGGCCACA 5410       5420       5430       5440       5450       5460
   AAAGCAAATA GGTGGGAAGG GAAGGGGGAC TCACATGTTA CTGAGACCAT TCAAGGAGCC 5470       5480       5490       5500       5510       5520
   ATGTGGGCAA GTGGATCAGT GCCCTTCACA TGGGGCGTGG CCTGGCATCC GGAGCGTGTT 5530       5540       5550       5560       5570       5580
   CTGCGGCTGG TAGGGTATGG GTATGTGCAG GGCAATCCTG GCCTAGACAG CAGGCACATT 5590       5600       5610       5620       5630       5640
   TGGAGGCACG GGACAGTAGT CTTTCGTGAG CACCATCCTT TCCAGCATAG CCAGGGTGGA 5650       5660       5670       5680       5690       5700
   TCCTGGGGTC CTGGGCTGGG AGGGTGAAGA GCAACAAATA AAGAAGTGGC TTCTTGGCCG 5710       5720       5730       5740       5750       5760
   GGCGCGGTGG CTCACGCTTG TAATCCCAGC ACTTTGGGAG GCCGAGGCGG GCGGATCACG 5770       5780       5790       5800       5810       5820
   AGGTCAGGAG ATCGAGACCA TCCTGGCTAA CACGGTGAAA CCCCGTCTCT ACTAAAAATA 5830       5840       5850       5860       5870       5880
   CAAAAAAAAT TAGCCGGGCG TGATGGTGGG CGCCTGTAGT CCCAGCTACT CGGGAGGCTG 5890       5900       5910       5920       5930       5940
   AGGCAGGAGA ATGGCGTGAA CCCGGGAGGC GGAGCTTGCA GTGAGCCGAG ATTGCGCCAC 5950       5960       5970       5980       5990       6000
   TGCACTCCCG CCTGGGCCAC AGAGCGAGAC TCCGTCTCAA AAAAAAAAAA AAAAAAAAAG 6010       6020       6030       6040       6050       6060
   AAGAAGTGGC TTCTTATAGT GTGTGGCTCA CTTCCTGCCT GGCCTCGTGG GGTTGCATGA 6070       6080       6090       6100       6110       6120
   ATCACTTTCC TTCCCAGGTG TATTTATTCA GAGCTGTGAG TGCACCTTGG AGTTCCTCTG
```

FIGURE 19G

```
          6130       6140       6150       6160       6170       6180
     TTTCCTCCTG AGGTCAGGGA ACTACCACCT CTCTGCCACT CATCCCCTAT GGCGGGAGAT 6190       6200       6210       6220       6230       6240
     ACATCCTCCA TCCCGTAGTG GGTTCCAGGG CTCAGAACCC TGGTACTCCT GAGCTCCCCA 6250       6260       6270       6280       6290       6300
     ACCCACCACT TCAGCTCAGC ACACACCAAT ACCCAGAGTT AGGACTGTGA GGTCTCCCTG 6310       6320       6330       6340       6350       6360
     GCACCAGCTG TGTGGGTTGG GGGCTCGGAC CCCTGCACCG GGAGGACCTG CCTCAGCTCT 6370       6380       6390       6400       6410       6420
     TGGCCTGCCC TGCCCACTGC CACCAGCACG TGGTTGACAG GGAAAGAACC CCCTTTTGTT 6430       6440       6450       6460       6470       6480
     CCCCACGTGA GCTCAAGCAA TCCACCCACT TCAGCCTCCT GAGTAGCTGG GATTACAGGT 6490       6500       6510       6520       6530       6540
     GCCCACTGCC ATGCTTGACT AATTTTTTGT ATTTTTAATA GAGACGGGGT TTCACCATCT 6550       6560       6570       6580       6590       6600
     TGGCCAGCTC AGCACACACC AATACCCAGA GTTAGGACTG TGAGGTCTCC CTGGCACCAG 6610       6620       6630       6640       6650       6660
     CTGTGTGGGT TGGGGGCTCG GACCCTGCAC CGGGAGACCT GCCTCAGCTC TTGGACTGCC 6670       6680       6690       6700       6710       6720
     TGCCACTGCC ACCAGCACGT GTTGACAGGG AAAGAACCCC TTTTGTTCCC ACGTGAGCTC 6730       6740       6750       6760       6770       6780
     AAGGAGACTT CCCTGAGTTG GAGCTCTCTG GTGTGGTCCT TCTCAGGCCT AAAGCAAAGT 6790       6800       6810       6820       6830       6840
     GTCTTTTCTG TGACACCTCC AAGGCCATGT TCAGGAGAGG GGAAGGGATC AGGGCCTGGT 6850       6860       6870       6880       6890       6900
     GGGAGGGATG GGGAGAGGGG ACTGGAGAAG GTGGCCTCCA GGGATCGAGT TTCCCATGGC 6910       6920       6930       6940       6950       6960
     CTCTTCCCAC CTGTCTTTGC CACAGGGGTG GGGACACCTG GCTGGCCCAG CCCAAGCCTC 6970       6980       6990       7000       7010       7020
     CACCCTGGGC TCCTGTGGGC TGGCTGCACT CGCCAGGGCT GGCCTAGGCT CTCTGCACCC 7030       7040       7050       7060       7070       7080
     AGGGAAGCTT CTCTATTCAA TGCTCTTCAC CCTCCCAGCC CAGGACCCCA GGAGATGAGG 7090       7100       7110       7120       7130       7140
     GAGAGTGGAG CAAAGGTTGA GGAGCAGAGG CTGGAGCCCC AGGCAGTGGC ACTGCTGGGC
```

FIGURE 19H

```
           7150       7160       7170       7180       7190       7200
      AGTGGTGGGA GGTGCCAGCC AGGGCTGGGA GTTGGACCCG AAAGTACGTG GCCTGGGCTG 7210       7220       7230       7240       7250       7260
      TACTTTCTTC CCACGTTGCC CCTTCAGAGC AGAAGCAGCC AGTTGCTCCT GAAGCCTTGA 7270       7280       7290       7300       7310       7320
      CCAGGGCTCC TGAGTCCAGA GCCTTGCTCA GGGCACTAGC GTGGGAGGAG GCTTCCGCAT 7330       7340       7350       7360       7370       7380
      CAGTACAGGG CATCAGCACC CGCCTCCTCA GCTGACCCAG CCCCGTGAGG ACCCAGGCCC 7390       7400       7410       7420       7430       7440
      AGCCCCCTGT CATCCCCACC CCCACCTTGC CAAGCCCCTG CCCCAGGAG CAGGGCTGAG 7450       7460       7470       7480       7490       7500
      AGCGAGGTGA TCTGGGTTCT AATCCAGAGT CTGCTGCTGA CATGTGCTGA GCCCCAGGCC 7510       7520       7530       7540       7550       7560
      CATTGGTTTA CTTGCCCCAG TATTGAGCGA GCATCCACTG GGTACCCGCC CAGTGCCGGT 7570       7580       7590       7600       7610       7620
      GCTGTGCCAG GGGCCGGGGC ACAGAATAAA GCAGACCCGT CCCTGCTCTT CTGGCATTCA 7630       7640       7650       7660       7670       7680
      CAGTCTTGTG GAAACTCCAG ACTGAAAGTG CCCTTAGAGA TTATCCAGAT CAGCCCCTCC 7690       7700       7710       7720       7730       7740
      TTGTAGCAAT GAAGAGACTG AGACCCACAG AGGGGATGAG TTTGATCCAA GAAACAGACA 7750       7760       7770       7780       7790       7800
      AGATTAAGAT GCATGTGTCT TGAACCTTTT CAGTGCTCTG GAACATACCG TCTGGCCGGA 7810       7820       7830       7840       7850       7860
      GTTGTCTGGG CTTTGGTTTT CCCATCCATG AAATGGGTAC AATAACAACA GCTATAGTGT 7870       7880       7890       7900       7910       7920
      ATGAGCCTCT GTGATAGATG CTGTACGCAC AGCACCTGAA CTCACATGAT AAACCACTGA 7930       7940       7950       7960       7970       7980
      GGTGAGCATT ATCTCCCATT ATCAAGGAGG ACCCTGGGGC TCAGAGAGGT TAAGCACGAT 7990       8000       8010       8020       8030       8040
      GCCAAGGCCA CACAGCCAGG GAAAGAAGAG TTGGAATTCA AACCCCGGGT GCCCTGTCTC 8050       8060       8070       8080       8090       8100
      ACACTAGCTT CCCCTGTGGA GGGTGCTGGT CTGTGCATGA TTGGAGGCCC TCACACAGTG 8110       8120       8130       8140       8150       8160
      TAAGTCTCAG GATCTGCAGC AAACTGGTCA GAATGCTCTG CCCTGGCCCA GGGAAGGAAA
```

FIGURE 19I

```
          8170       8180       8190       8200       8210       8220
     GAGGGGCAGA TGGAGTTTGC TTCGCTGTAA GGCCCCGGAG CTTTGTGTTC CTGCTGAGAA 8230       8240       8250       8260       8270       8280
     GCCTCAGAGT CGGGCAACAC TGGGTCTAAT TCCAGCTCCA CCCCTTGTAT TAATAGCTGG 8290       8300       8310       8320       8330       8340
     GCCTTAATCT CCTCATCTGT AAAATGGAGA GAATCGTCGC CTGTACTTCA TAAGGCTGCT 8350       8360       8370       8380       8390       8400
     GGAAGGATTA GCTAAAGCAA CCCAGCTACA GTGGCTGGCC TACAGTAGGT GCTTCATTAA 8410       8420       8430       8440       8450       8460
     TGCCCTTCCT TTTAGATGTG GAAATTCCTC TTTTTGTCCA AGTTTTCTTT TCCTCTTTGC 8470       8480       8490       8500       8510       8520
     TTACGGCACT GGGATTTTCT TTATTACTGT TTCTTTGAAG AGTCCGCTCT GTACTTGTGC 8530       8540       8550       8560       8570       8580
     CCACGGCTAT GGTCAGTAAC CCCTTATGGA ATAAACCCC TTTCCTGGCC AGGTGTGGTG 8590       8600       8610       8620       8630       8640
     GCTCATACCT GTAATCCCAG CACTCTGGGA GGCTGAGGCG GGAGGATCAC TTGAGCCCAG 8650       8660       8670       8680       8690       8700
     GAGTTCGAGA CCAGCCTGGG CAACACAGTG AGACCCCTGT CTCTACTAAA CATACAAACA 8710       8720       8730       8740       8750       8760
     ATTAGCCAGA TGTGGTGGTG CATACCTGTA GTCCCAGCTA CTCAGAAGGC TGAGATAGGA 8770       8780       8790       8800       8810       8820
     GGATCACCTG AGCCCAGGAG ATGAGGCCAC AGTGAGCTGT GATTGCACCA CTGCACTCCA 8830       8840       8850       8860       8870       8880
     GCCTGGGCAA CAGAGTGAGA CCCTACCTCA AAAAGAAAGC AACAACAGAA AACCTATTTC 8890       8900       8910       8920       8930       8940
     CCTATCCTAA TTGCACCTCC ATTCAAAGAG CTGCCCCTGC AAGAGTTAAC CAACTCCCTA 8950       8960       8970       8980       8990       9000
     GCCTCCCATG AGTTCTGAAA TCCTGCACCC AGGCCTGGTC CCAGTTGCCT AGCAACCGGG 9010       9020       9030       9040       9050       9060
     GGCTGCTCTG GGATGCAGTA GGTAAGCAGG GGAGGGAGAG GAAGAAAACA ACTTGGTCTG 9070       9080       9090       9100       9110       9120
     TCCACGACTC TAAATGTCAC TGAGAGATCA GTGCAGAGAA AGGCCTGTCA CCAGAGCCCA 9130       9140       9150       9160       9170       9180
     GGGCCCAATT TGCCTGGTGG TAGGGACAGC TGCCCTCAGG CCACCTGGGA GGTGGTTATC
```

FIGURE 19J

```
           9190       9200       9210       9220       9230       9240
      CCTCCTTTGA GTGGGCTTAC ATAACTACTT GGCATTTTTG CAAGGGACTT TAAGCTCACT 9250       9260       9270       9280       9290       9300
      CAGCAGTGAC ACCCCCCTCC GCCCACATGC ACATACATGT GTGGTACAGG GAGGACCCGG 9310       9320       9330       9340       9350       9360
      TGTGGGAGGC AGAGATGGGG TTCCAGCCAA CTGAAACTCC ATCATCTGCA TCTCCCGGCC 9370       9380       9390       9400       9410       9420
      TCTGACTGCC TCCCTCTGCC AAAGCGGGAA GATGAAAATG GTAACTGCTG GAATTTGTAT 9430       9440       9450       9460       9470       9480
      TTTGCAAAGA CTTTTCTCAT TTACTGCTGA ATATATTCCT CATCTCAGCC TCCACTCGCT 9490       9500       9510       9520       9530       9540
      GACACGCTAC CCACTGTCTC TCCCAGCATT CATCTCTACC TGAAATGATC TTGTTTACTT 9550       9560       9570       9580       9590       9600
      CTCTGTGTCT GTGTGCCTCG ACTCTCCCCC ACCGACTAGA AAGGTCCGTG AGAGCAAGGA 9610       9620       9630       9640       9650       9660
      GCAAGCCTGT CTTGTTTGAG GGCACTGGTT CTCATAGAGC CACAGGGAAT GATGCCCCTG 9670       9680       9690       9700       9710       9720
      GACTAAGCAG TGTGGGGTCT GCTGGCTTGC ACCTGTGCCC CCAGCTCCTA GCCAAAGACC 9730       9740       9750       9760       9770       9780
      AGACACATGT TGGGAACTCA ATACTTGTTT GTTTAATGAG TAGATGAACA AAAGCACTCA 9790       9800       9810       9820       9830       9840
      TGAAATAGGC AGTGCACGTA TCTTTATCAC CATTTGAAAG CTGAGGAAAC AGGCTTGGAG 9850       9860       9870       9880       9890       9900
      AGGGAAGCAA CTTGCCTGAC ACCCCAAATC ACAGAAGCAG CATATTTGGC CCAAGAACCT 9910       9920       9930       9940       9950       9960
      GGCTTCCTGT CTCCAAGGGG TCAGGTCCAG CTGGCATTGG CCTGTAGGCA TGTGAGTGTG 9970       9980       9990      10000      10010      10020
      GCAAGGTAGT CAGCAAAGAG CCTTTACTGC ATGTTGGGGT CAGAAGATCA GCAATAAGGA 10030      10040      10050      10060      10070      10080
      GGACAAAATC CTTGCCTGGA AGGAGCTTGT GTTCCAAAAA GAACAAGAGA CCACAGCATA 10090      10100      10110      10120      10130      10140
      TTCATTAATA AAGACACATT CAAACAGGGC CAAGTGCTCT GAAGCACCTC AGACAAAGCG 10150      10160      10170      10180      10190      10200
      ACAGGCTGCA AAATGACAGC GTTTGGGGGT CAGGAGACAG AAGGGTGCCT GCTTTAGGTG
```

FIGURE 19K

```
         10210      10220      10230      10240      10250      10260
     GTCGAAGAAG GCCTCTCTGG GGAGGTGGCA TTTGGTCTGA GACCTCAGGG CCAATGTGCT 10270      10280      10290      10300      10310      10320
     AGGAGCAGAG GAGCCTTGGG GAAGAATGGA GATGAGGTTG GACAGGATGA GACACGTGCC 10330      10340      10350      10360      10370      10380
     TTCTATGTCA ATGGCAAGGG AGTCATTGGA GCATGTGAAG CAGAGGATGC TCTACTTTTG 10390      10400      10410      10420      10430      10440
     CCCCAGAAAG ATCACTCTGG CTACAGTGCA GAGAAAGAAG AGAGTCAAGG AGGAAAGAAG 10450      10460      10470      10480      10490      10500
     GGCCTCATTA GGGGACTGTT GCAAAGCACA GGGAGGCACA ACCACAGCCA AGATCAGCAT 10510      10520      10530      10540      10550      10560
     GGTGACCAAT GGATGGAAGT GTCAGATGTC GCATGCTGTC GGTAGGTCAG GGCCGACAGG 10570      10580      10590      10600      10610      10620
     ACCTGTCGAT GGGTTCAGCG TGGGGTGTGA AGGAACACAG GCTGCACCCC AGCTCCTGGC 10630      10640      10650      10660      10670      10680
     CTGAGTGGCT GTAGATAGTG GCACCAAATA CTGAGCTCGT GAAGATGGGG GAGAGCTGAT 10690      10700      10710      10720      10730      10740
     GATGAAGACA GCAAGAGTTT GGTGTGAGTC ACCTTGAGTT TGAGACACGT GTCAGACATG 10750      10760      10770      10780      10790      10800
     TAAGGGGTAG GCAGGTGGAC ACGTGCTTAT TGAAGTCTGG AGCCAAGGGA GAGGTGTGGG 10810      10820      10830      10840      10850      10860
     CTGCAGCGGA GAAGTTGGGA GTATTCAGAG TTCTGACACT GACCAAGAAC ACCCCTCAGA 10870      10880      10890      10900      10910      10920
     GAATTCAGAG ACAACCAGGG CTGAGGCGAG GGGCTTAGAC TGGGGCCTGG GACAGCCACA 10930      10940      10950      10960      10970      10980
     GGCAGGAATG CAGACTTGCT GCCTCTTCTT ATTTGTGGAG ATGTAGTTCA TGCAGCAAGA 10990      11000      11010      11020      11030      11040
     AAGTCATTCC AAAGCCCTCC TTTCCTTTCT TCATGCCTCA GTTTCTCCAT TAGCACATTA 11050      11060      11070      11080      11090      11100
     AAAGATGCAA GATCTGGAGT TAAGCTTGTT TTTAAAAGGT GGCCTCCAAA GACGGTTTTT 11110      11120      11130      11140      11150      11160
     CTTGGCCTGG GGCTGTCTCA TCATCCAGGT CATGACAGGC CCGGTCCATG GTTGAGGAAT 11170      11180      11190      11200      11210      11220
     GCCACAGAAG TGACAGTCCA CTGCAAAAGA CTGCTGCTCC AGATCAGTTC TGGAAGGCCT
```

FIGURE 19L

```
        11230      11240      11250      11260      11260      11280
    GGCAATGGGG CAGGCCACTG AAGTAGAACT GGATGTCAGA TGCACGCATT AGAAAGGACA 11290      11300      11310      11320      11330      11340
    GGAAGACCAA ATGAGAAAGG GAGAGGGGGC AGGGAGAAAG GAAGGAGAGC TAGAGACTTG 11350      11360      11370      11380      11390      11400
    AGGCAAAGGA AACAAGAGAT GGAATAGAAG AAGACAGAGG ACCAGAAGAC AGTGAGACCA 11410      11420      11430      11440      11450      11460
    ACAGAAAGAG AGAGGGACGA GAAAGAAGGT GGCTGAGGAA GGTGAGAAAA GTGTTTCCAG 11470      11480      11490      11500      11510      11520
    GGCGACAGCA ACTGGACCAG GCCCTCTAGT TGGACAGTGA GGCTGGCTGG GGGGCCTGAG 11530      11540      11550      11560      11570      11580
    CTCAAGTAGC CCTCGTCCCC TGAGAGAGTG GGGGCTACCT GGGGAGCTGG GCTTGATGCA 11590      11600      11610      11620      11630      11640
    TCTGGAAGGA TCTTCACAGA GGCAGGAGGG GGAGTGGGAG GGCAGAGGGC ACCCAGGCGC 11650      11660      11670      11680      11690      11700
    TAGAACAGTG GGAGTGGCGG GACGCAAAAC CGGAGAGCCA GAGGAGTGAA CATCCCTGGC 11710      11720      11730      11740      11750      11760
    AGATTCCCCT GCGGCCGAGC AGGAGGGCAG GAAGCTCAGT GGTGTTGGCA CAACGTGAGA 11770      11780      11790      11800      11810      11820
    AGTTCCAGGG AGGCGTGGGA GGACGGCTTC TGCAGGACGC AGACTTTGCA GAGGGAGAGT 11830      11840      11850      11860      11870      11880
    GGCAAACAGA CTGACTGCAG GCAGCTCTGC CGGCTCCACA GGGCGCTGCT TTTTCTCCAC 11890      11900      11910      11920      11930      11940
    GGTGGAGCTG GAGTGCATCA CCCTGAGAAC CAGCAGCAAG CCCCCACAGG GCACCTTCTG 11950      11960      11970      11980      11990      12000
    CGTGCCAGGC ACATCCGGAC CACTTGTCGG TAGACACCAG TGACCCTCAC CACCACCCCA 12010      12020      12030      12040      12050      12060
    GGAATGGGAC AGTGTCATGT GTTTCTGAAA TGACTAGGTT TTAGCACCAT TTCATAGATG 12070      12080      12090      12100      12110      12120
    AGGAAGCTGA AGCTAACTTG CCCAAGGTCA TAAACCGGGC GTCTGGTGGC CTCCCCTCCT 12130      12140      12150      12160      12170      12180
    CACTGCCAAC CCTGAGAGCG GACTAGGGTG GAGTTATCTG GAAAGAGGAA GCTGTACCTG 12190      12200      12210      12220      12230      12240
    AGAGCCCTAA ACACACATGC GCGCGCACGA CACACACACA CGCACAAACA CACAATGCAC
```

FIGURE 19M

```
          12250      12260      12270      12280      12290      12300
     GCACACACAT GCGCACGCAC ATACACACAC ATGCACACAT GGACACATAC CTGCACACAC 12310      12320      12330      12340      12350      12360
     AAGCATACAC ATGCACACAG GCACACGCAT GCACACACGC GCATGCACAC ACATGCACAC 12370      12380      12390      12400      12410      12420
     ACATGTGCAT GCACACAGTG CGACAGCTCT GATTAGTAGG TAAATAAAAG GTTCCCATCT 12430      12440      12450      12460      12470      12480
     AGTGGTGACT CGGCCAAAGT GCAGACACTG AACCCCAAAG GCCCATAGAG GCTTCATTCA 12490      12500      12510      12520      12530      12540
     TCCCTTCTCT TATTCTTCAT TCATGGATTC TATTGAGCAT CTGCTCTGTG CAGCATCTGT 12550      12560      12570      12580      12590      12600
     CCTGGATGCT GGGGATACTG TGATGACTTA GACAAGGTCT CAGCCGCACA CAGCTTATGC 12610      12620      12630      12640      12650      12660
     TTCTTTGAGG GGAGGCAGAC ACAAGCCAGG AAACCAATAA GAGAAGTTAA GTAAAAAGCA 12670      12680      12690      12700      12710      12720
     CAGTGAGTGA GACAAACGGG TACGGAGGAC ATGGCCAGAG AGAGCTTTAG TTCAGGTGGT 12730      12740      12750      12760      12770      12780
     CAGGGAGCAC CTCTCTGAGG AGGTGAAATT TGACCAAGCC TCAAACAGTG GCAGGGATCC 12790      12800      12810      12820      12830      12840
     CACTGCTTGC AGATCCTGGG GAGAAGCATT TTAGACAAAA AGAACAGCAA GTCCAAAGGC 12850      12860      12870      12880      12890      12900
     CCAGAGACAA GACAGAGCAA GACCTGTGAC ATGAAACAGG CTGGTGTGCC CAGAGCAGGG 12910      12920      12930      12940      12950      12960
     AGGCTGGGAG AGTGGAGGGG GAGGGCGATG AGGGTGGAGA AGCTGGTGAG GGTGGCATCC 12970      12980      12990      13000      13010      13020
     CGGCAAGTGT GCCTGGCCAC GGAGGCCACG GAAGGATTCA GCATGTCTTT CCCGAATAGG 13030      13040      13050      13060      13070      13080
     AACCACACTG GGCTGTAACA GAGAGTGACG TACTCGGTAC GTTGAGAAGG TCCTGCTTAT 13090      13100      13110      13120      13130      13140
     TTCCTTCCGT GAAGGAGGAA GAGCTGCTGA TGACAGAGAT TGGCAGTGGC CAAAGACATA 13150      13160      13170      13180      13190      13200
     GAGAGAAGAG GGCAGAACAT GGGCTATTTT AAACACAGAG AAGATTAGCG GGACCCGCTG 13210      13220      13230      13240      13250      13260
     GCAGACCGGA CGTGAAATGT GGAAGGAGCG GGGGCAGCGA GGTCGGCTCC TAGTTTCCTG
```

FIGURE 19N

```
        13270      13280      13290      13300      13310      13320
   AGAATGTGGG TGAATCACGG GCTCACAGGC AGAGGGAGCA CTAGGATATC AAGGGTTCCC 13330      13340      13350      13360      13370      13380
   TTGTGAACGC CTCAAGTTGG AGATGCCTGA GACATCCAAG TGAGATGTCA AGCAGGCAGC 13390      13400      13410      13420      13430      13440
   TGGAAATAGG AGATGAGCTC TGGGAAAATG CTCCCATCAC CCTGGCCTGT GTGCTGCCTG 13450      13460      13470      13480      13490      13500
   GGCGCACCCA TTCAGGGCCC TCCACGCAGC CCACGCCCCT GCCTCCTGAT TCCTTCTAGG 13510      13520      13530      13540      13550      13560
   CTTCTCCAGC ACTCGTGGGA TGCCCAGATG TGATCAGGGA AGGGCTTGAG GATGCAGGGA 13570      13580      13590      13600      13610      13620
   AGCTGTGGCT GAGAGCCCTA AACACACACA TGCACACGCA CACACACATA CACAGGCACA 13630      13640      13650      13660      13670      13680
   TGCACACACG ACCATACACA CACACAAATG CACGCAGATG CACACAAATG CATATGCACG 13690      13700      13710      13720      13730      13740
   CACACAAATG CATATGCACA CACACACATG CACACATATG CATACACGTA TCCCTTTCAG 13750      13760      13770      13780      13790      13800
   TGGCTTTCCT TTCTGTCCTT AACCCTTGGC CCCTTACAGT GAGCTCCCAG TTCTCCCCAG 13810      13820      13830      13840      13850      13860
   CCTTAGAACC AAACCCTGGG GCTGGGCTGG GAGCCCCCAG TGACCCTCTG TGTCTCTGTA 13870      13880      13890      13900      13910      13920
   GGTGGATGCA CCCTTGGTCC TGGTGCCAGC TGCCACTGCA GGCTGAAGGC CTGTGAGTGT 13930      13940      13950      13960      13970      13980
   GACAAGCAAT CCGTGCACTG CTTCAAAGAG AGCCTGCCCA CCTATGAGAA AAACTTCAAG
                              Exon 4

13990      1400       14010      14020      14030      14040
   CAGTTCTCCA GCCGGCCCAG GTGTGGCAGA CATAAGCCCT GGTGCTAGGG ACACCACAGG 14050      14060      14070      14080      14090      14100
   GTCCCTCTCA TCATCCAGCA TCCGCTCTAG TGTTGCTCTT CCAGGAAGCC TTCTCAGATC 14110      14120      14130      14140      14150      14160
   ATCCCCAACA GGCCCCTGTT CTTCCACTGG GAGGGAGGAC AAAATGTCTC CCGCAGGGCA 14170      14180      14190      14200      14210      14220
   GCTCACCCTT CAGCATTCTG ACCAAGGGGA CTCCCTGTCG TTCAGCATCA GAGGGCTGGA 14230      14240      14250      14260      14270      14280
   GAGCAGAAAT GGGAAAGATG AGATGCCTGC CCTGCAGGAG CTGGCATTCT GTGGAGTGGG
```

FIGURE 19O

```
          14290      14300      14310      14320      14330      14340
     GAGGACTACA AATGCATGGA TATAGAAGTA AGAGACACAT TAGACTGTAG TAAGTGCTAT 14350      14360      14370      14380      14390      14400
     GATGCAGTAA AACAAAGGGA CGGGATAGAG ATGCACCCAA CCCCACATCC CAGGGGTTTC 14410      14420      14430      14440      14450      14460
     CAGGAGGGGA GAAGCCCCAG GATCTACCCC AAACTCTCTC TTCACCCCCA CTGCAAACCG 14470      14480      14490      14500      14510      14520
     GGACACAGAG CAGACTTGAG CGCCAGGCCC ATGCCCAGCT CTAGCTGGCA ACAAAGCCAC 14530      14540      14550      14560      14570      14580
     CACTTTCCTT GCCCCTCTGC GTCCTCAGTT TTTATGATGT CATTCTTAGC TTTTCTTATC 14590      14600      14610      14620      14630      14640
     AAGAGGCAGA ATCTGTTTTC CCCATCCCAT GAATCTGAAC TGGTCTTGTG GCTTAGTTTG 14650      14660      14670      14680      14690      14700
     GTCAATAGAA TGTTGTGGGA GGGATGGTTT ACCAGTTTTG AGCTAGGCCT CAGGAGGTCT 14710      14720      14730      14740      14750      14760
     AGGGCATGTC TACTCTCTCT TAGGACAGCT GCCCCACCC TGCAAAAAG CCTGGGCTAG 14770      14780      14790      14800      14810      14820
     CCTGCTGGAG GATGAGAGCC CACCTGGATC AGTTGTCTCA GCTGATTTCA GACACGTGAG 14830      14840      14850      14860      14870      14880
     AGAGAGCTCA GCGAGACTCA GCTTGTAGCT GACTACAGAT GTGTGAGGGA ACCTGGCTGA 14890      14900      14910      14920      14930      14940
     GACCAAAACA ACTGTCCAGC TGAGCCCAGG CTAAACTGCC AACATGCAGA ATTGTGAGCT 14950      14960      14970      14980      14990      15000
     AAATAAAGGC TGCTGTTCTA AGTCACTGGG TTTTGGTATG GTTTGTTAGG CAGCCATAAC 15010      15020      15030      15040      15050      15060
     TAACAGGTGT AATTGGTCCT TATTCCCTTA TTCACTGAGA GTGATGGGTT CTCAGCCCTG 15070      15080      15090      15100      15110      15120
     AGCTGGACTT GGAGGCCATG GAAATGCAGT GGACATGGCC TTTGTTCCTT ACCTTGAAGC 15130      15140      15150      15160      15170      15180
     TGTGGAAGGA GGTCAAGTTC ATGGAATAAT GGAGAACACA CAGCTGTAAT CGTTTGCTTG 15190      15200      15210      15220      15230      15240
     TTCAGGGAAC ACACATTTAT TGAGCACTTG CTATGTGCCA GGCACAGTGC CAGGCAGTAG 15250      15260      15270      15280      15290      15300
     GGATCCAGAT ATTTAAAGAA AACAAACAAA AATCAGGTCC AAAACTCCTG GGGAGAATGC 15310      15320
     TGAGAGTGGT ATCAGCTTTT AGGAATCC
```

Fig. 22

```
            1                              Ca++
H I     AVWQFRKMIK  CVIPGSDPFL  EYNNYGCYCG  LGGSGTPVDE  LDKCCQTHDN
H II    NLVNFHRMIK  -LTTGKEAAL  SYGFYGCHCG  VGGRGSPKDA  TDRCCVTHDC
H IV    GLLDLKSMIE  -KVTGKNALT  NYGFYGCYCG  WGGRGTPKDG  TDWCCWAHDH
R IV    GLLELKSMIE  -KVTGKNAVK  NYGFYGCYCG  WGGHGTPKDG  TDWCCRMHDR
R III   SFWQFQRMVK  -HITGRSAFF  SYYGYGCYCG  LGGRGIPVDA  TDRCCWAHDC
                      **  **        *        *  **  **
              .
              9                 25    29    32          42 44    48
                                26    30                   45    49

51          ELAPID LOOP
H I     CYDQAKKLDS  CKFLLDNPYT  HTYSYSCSGS  AITCS---SK  NKECEAFICN
H II    CYKRLEKR-G  C-----GTKF  LSYKFSNSGS  RITCA----K  QDSCRSQLCE
H IV    CYGRLEEK-G  C-----NIRT  QSYKYRFAWG  VVTCE----P  GPFCHVNLCA
R IV    CYGLLEEK-H  C-----AIRT  QSYDYRFTQD  LVICE----H  DSFCPVRLCA
R III   CYHKLKEY-G  C-----QPIL  NAYQFAIVNG  TVTCGCTMGG  GCLCGQKACE
         **                         *            *             *
         51                         73           84            99
         52
            101                              CARBOXY EXTENSION
H I     CDRNAAICFS  KAP--YNKAH  KNLDTKKY-C  QS
H II    CDKAAATCFA  RNKTTYNK-K  YQYYSNKH-C  RGSTPRC
H IV    CDRKLVYCLK  RNLRSYNP-Q  YQYFPNIL-C  S
R IV    CDRKLVYCLR  RNLWSYNR-L  YQYYPNFL-C
R III   CDKLSVYCFK  ENLATYEKTF  KQLFPTRPQC  GRDKLHC
         ++ *           *
         108           116
```

Alignment of amino acid sequences of mature Human (H) Type I, II and IV and Rat (R) Type III and IV $PLA_2$. Asterisks denote residues that have been conserved among all active $PLA_2$ sequences. The dot indicates a residue conserved in all active sequences, except the Rat Type III shown here. The + indicates residues conserved in all Type I and II enzymes known to date. The position numbers are indictated under the asterisks. The Elapid loop, Ca++ binding site, and carboxy extensions are also shown.

---

Top line is SEQ ID NO: 38
Second Line is SEQ ID NO: 39
Third line is SED ID NO: 40
Fourth line is SEQ ID NO 44
Last line is SEQ ID NO 43

Fig. 27

```
              1                                              46
RPLA2-Type  I  AVWQFRNMIKCTIPGSDPLREYNNYGCYCGLGGSGTPVDDLDRCCQ
RPLA2-Type II  SLLEFGQMIL-FKTGKRADVSYGFYGCHCGVGGRGSPKDATDWCCV
RPLA2-8        SFWQFQRMVK-HITGRSAFFSYYGYGCYCGLGGRGIPVDATDRCCW
RPLA2-10       GLLELKSMIE-KVTGKNAVKNYGFYGCYCGWGGHGTPKDGTDWCCR
                        *             **  ** *        *  **

47                                             92
RPLA2-Type  I  THDHCYNQAKKLESCKFLIDNPYTNTYSYKCSGNVITCSDKNND--
RPLA2-Type II  THDCCYNRLEKR-GC-----GTKFVTYKFSYRGGQISCS-TNQDS-
RPLA2-8        AHDCCYHKLKEY-GC-----QPILNAYQFAIVNGTVTCGCTMGGGC
RPLA2-10       MHDRCYGLLEEK-HC-----AIRTQSYDYRFTQDLVICEHDSF---
                 ** **                         *        *

93                                            137
RPLA2-Type  I  -CESFICNCDRQAAICF--SKVPYNKEYKDL-DTKKHC
RPLA2-Type II  -CRKQLCQCDKAAAECFARNKKSYSLKY-QFYP-NKFC<u>KGKTPSC</u>
RPLA2-8        LCGQKACECDKLSVYCFKENLATYEKTFKQLFPTRPQC<u>GRDKLHC</u>
RPLA2-10       -CPVRLCACDRKLVYCLRRNLWSYNRLY-QYYP-NFLC
                    *       *                *
```

Alignment of amino acid sequences of rat Type I, II, RPLA$_2$-8 and RPLA$_2$-10 PLA$_2$s. Asterisks denote eighteen residues that have been conserved among all active PLA$_2$ sequences. Underscored residues denote the amino acid COOH-terminal extensions.

RPLA$_2$-Type I sequence shown corresponds to SEQ ID NO: 41:; RPLA$_2$-Type II sequence shown corresponds to SEQ ID NO:42:; RPLA$_2$-8 sequence shown corresponds to SEQ ID NO:43:; RPLA$_2$-10 sequence shown corresponds to SEQ ID NO:44:.

MAMMALIAN PHOSPHOLIPASE A₂ NUCLEOTIDE SEQUENCES, LOW MOLECULAR WEIGHT AMINO ACID SEQUENCES ENCODED THEREBY, ANTISENSE SEQUENCES AND NUCLEOTIDE SEQUENCES HAVING INTERNAL RIBOSOME BINDING SITES

This application is a divisional of prior application Ser. No. 08/888,497, filed on Jul. 7, 1997, entitled Mammalian Phospholipase A2 Nucleotide Sequences, Low Molecular Weight Amino Acid Sequences Encoded Thereby, Antisense Sequences and Nucleotide Sequences Having Internal Ribosome Binding Sites now U.S. Pat. No. 5,972,677, which was a continuation of application Ser. No. 08/651,405, filed May 22, 1996, now abandoned, which was a continuation of application Ser. No. 08/097,354, filed on Jul. 26, 1993, now abandoned.

FIELD OF THE INVENTION

The present invention relates to novel mammalian phospholipase $A_2$ nucleotide sequences, low molecular weight (Approximately 14 KD) amino acid sequences encoded thereby, clones and vectors which include the mammalian phospholipase $A_2$ nucleotide sequences, antisense nucleotide sequences complementary to the genes and mRNA transcripts encoding for the phospholipase amino acid sequences, nucleotide sequences having internal ribosome binding sites which allow for internal initiation of mRNA cap-independent translation, and cell lines.

BACKGROUND

Phospholipase $A_2$s—phosphatide 2-acyl-hydrolase, EC 3.1.1.4 (hereinafter "$PLA_2$") constitute a diverse family of enzymes that hydrolyze the sn-2 fatty acyl ester bond of phosphogylcerides, producing free fatty acid and lysophospholipids. See Dennis, E. A. Phospholiphases. In: *The Enzymes*, edited by Boyer, P. New York: Academic Press, p. 307–353 (1983). Over the past two decades, $PLA_2$ activities have been purified and characterized from different tissues, cultured cells, and exudates from different mammals. See Rordorf, G. et al.: *J. Neuroscience,* 11:1829–1826 (1991); Seilhamer, J. J. et al.: *J. Biochem.,* 106:38–42 (1989); Langlais J. et al.: *Biocham. & Biophys. Res. Comm.,* 182:208–214 (1992); Murakami, M. et al.: *J. Biochem.,* 111:175–181 (1992); and Jordan, L. M. et al.: *J. Chromat.,* 597:299–308 (1992). These enzymes have been found to vary in molecular weight, optimal pH, $Ca^{2+}$ dependence, substrate specificity, and solubility.

To date, two classes of unrelated $PLA_2$s have been reported. One is a family of low molecular mass, approximately 14 kDa $PLA_2$s which are characterized by a rigid three dimensional structure maintained by disulfide bridges and a catalytic requirement for $Ca^{2+}$. The other is a high molecular mass, 82 kDa, intracellular $PLA_2$ found in the cytosolic subcellular fraction in the absence of calcium, but associated with cellular membranes at calcium concentrations from 0.1 to 10 $\mu M$. See Clark, J. D. et al.: *Cell,* 65:1043–1051 (1991) and Sharp, J. D. et al.: *J. Biol. Chem.,* 266:14850–14853 (1991). In addition, several $Ca^{++}$-insensitive $PLA_2$ activities are believed to exist, however, it is also believed that as yet none of the genes encoding such activities have been cloned.

In terms of structure, low molecular weight, e.g., about 14 kDa, $PLA_2$s rank among the best characterized enzymes. Complete primary sequences have been determined for more than 50 $PLA_2$s from organisms such as snakes, bees and humans. See Heinrikson, R. L.: *Methods in Enzymology,* 197:201–214 (1991); Davidson, F. F. et al.: *J. Mol. Evolution,* 31:228–238 (1990); and Dennis, E. A. Phospholiphases. In: *The Enzymes,* edited by Boyer, P. New York, Academic Press, p. 307–353 (1983). In all active 14 kDa $PLA_2$s, 18 amino acids are believed to be conserved. See Heinrikson, R. L.: *Methods in Enzymology,* 197:201–214 (1991) and Davidson, F. F. *J. Mol. Evolution,* 31:228–238 (1990). Based on selected structural determinants, the low molecular weight $PLA_2$s have been classified into two types. See Heinrikson, R. L. et al.: *J. Biol. Chem.,* 252:4913–4921 (1977). Type I enzymes have a disulfide bridge connecting cysteines between amino acids 11 and 77. In addition, there is an insertion of three amino acids between residues 54 and 56, the so-called elapid loop. The only identified mammalian Type I $PLA_2$s, see Seilhamer, J. J. et al.: *DNA,* 5:519–527 (1986) and Ohara, O. et al.: *J. Biochem.,* 99:733–739 (1986), are expressed mainly in the pancreas and function extracellularly in digestion. Type II $PLA_2$s, on the other hand, lack the disulfide bridge between amino acids 11 and 77, have carboxy-terminal (COOH-terminal) amino acid extensions which can vary in length, but are commonly seven amino acids in length, which typically terminate in a half-cysteine joined to Cys-50 near the catalytic site His-48. The mammalian Type II $PLA_2$s reported to date occur in trace amounts in several tissues such as liver and spleen and are secreted from various cells in response to appropriate stimuli. See Seilhamer, J. J. et al.: *J. Biol. Chem.,* 264:5335–5338 (1989); Kramer, R. M. et al.: *J. Biol. Chem.,* 264:5768–5775 (1989); Komada, M. et al.: *J. Biochem.,* 106:545–547 (1989); Kusunoki, C. et al.: *Biochimica Et Biophysica Acta,* 1087:95–97 (1990); Aarsman, A. J. et al.: *J. Biol. Chem.,* 264:10008–10014 (1989); Ono, T. et al.: *J. Biol. Chem.,* 264:5732–5738 (1988); Horigome, K. et al.: *J. Biochem.,* 101:53–61 (1987) Nakano, T. et al.: *Febs. Letters,* 261:171–174 (1990); and Schalkwijk, C. et al.: *Biochem. & Biophys. Res. Comm.,* 174:268–272 (1991). It is believed that Type II $PLA_2$s are associated with the pathologies of several diseases involving infection, tissue damage, and inflammation, such as acute pancreatitis, septic shock, peritonitis and rheumatoid arthritis. See Vadas, P. et al.: *Lab. Invest.,* 55:391–404 (1986); Pruzanski, W. et al.: *Advances in Exper. Med. & Biol.,* 279:239–251 (1990); Uhl, W. et al.: *J. Trauma,* 30:1283–1290 (1990); and Malfertheiner, P. et al.: *Klinische Wochenscrift,* 67:183–185 (1989). Mammalian Type I and II $PLA_2$s share approximately 30–40% amino acid homology; however, eighteen amino acids are invariantly conserved in all known functional $PLA_2$s. Type I mammalian $PLA_2$ genes contain 4 coding exons; Type II mammalian genes contain five exons, the first of which is noncoding.

In 1990, a distinct 120 bp putative $PLA_2$ exon-like fragment (h10a), homologous to the amino-terminus encoding region of known $PLA_2$s, was obtained by screening a human genomic DNA library with a 45 bp human $PLA_2$ Type II oligonucleotide probe. See Johnson, L. K. et al.: *Advances in Exper. Med. & Biol.,* 275:17–34 (1990). Zoo blots indicated that the putative exon has been highly conserved during evolution. However, additional exons indicating the presence of a complete gene, a corresponding cDNA, or evidence of transcription in different human tissues was not found.

Neuronal ceroid lipfuscinoses (NCL), or Batten disease, are terminal, inheritable, lysosomal storage diseases of children. They are characterized by the accumulation of an autofluorescent pigment (ceroid or lipofuscin) in cells, especially neurons and epithelial pigment cells of the retina. NCL patients typically manifest high levels of the highly reactive compound, 4-hydroxynonenal. These levels are believed to be a consequence of a failure to resolve peroxidized, fatty acids in the normal way. It is believed that this failure could be the result of a phospholipase $A_2$ defect.

The infantile form of NCL has now been linked to chromosome 1p33–35. See Jarvela, I. et al.: *Genomics*, 9:170–173 (1991). The non-pancreatic $PLA_2$ (Type II) has also been mapped to chromosome 1. The Type II gene and two additional putative exon-like "fragments" (h8 and h10a), see Johnson, L. K. et al.: *Advances in Exper. Med. & Biol.*, 275:17–34 (1990), are located at about 1p34—in the middle of the region where gene for infantile NCL is believed to reside. See Jarvala, I. et al.: *Genomics*, 9:170–173 (1991). h8 and h10a each contain a unique sequence which is highly homologous to, but distinct from, exon two (which contains the calcium binding domain) of $PLA_2$ Type II.

Consequently, there is a continuing need to further identify and characterize additional $PLA_2$ exons if such exist. Such exons could be part of unidentified genes. To the extent there are additional unidentified $PLA_2$ exons and genes, they may encode proteins (enzymes) that function in a manner different from, similar to, or overlapping with, the known $PLA_2$s. Moreover, such unidentified exons and/or genes and the enzymes encoded thereby may be regulated by some of the same effectors as the known $PLA_2$ genes and their proteins. Investigation of these unidentified exons and/or genes and their encoded enzymes may therefore result in new approaches to therapy of $PLA_2$-related diseases, such as Batten disease and inflammatory disease. Alternatively, these unidentified enzymes may have entirely different physiologic and pathologic functions. Thus, therapeutic approaches designed to block the activity of the known Type II $PLA_2$ enzymes may also block or reduce the activity of these novel enzymes, thereby producing unexpected side effects. Still further, a better understanding of the regulation of expression of the known and unidentified Type II $PLA_2$ genes in different tissues will likely expand the overall understanding of the biology and metabolic processes involving $PLA_2$s.

SUMMARY OF THE INVENTION

In brief, the present invention overcomes certain of the above-mentioned shortcomings and drawbacks associated with the present state of the $PLA_2$ art through the discovery of a novel family of mammalian $PLA_2$ genes or nucleic acid sequences encoding low molecular weight amino acid sequences, clones, vectors, antisense nucleotide sequences, nucleotide sequences having internal binding sites, and cell lines.

More particularly, the low molecular weight, i.e., about 14 kDa, amino acid sequences encoded by the novel family of mammalian $PLA_2$ genes or sequences of the present invention may be generally characterized as enzymes having esterase activity specific for the acyl group at the sn2 position of glycero-phospholipids. Moreover, the novel amino acid sequences of the present invention do not include disulfide bridges between cysteine amino acids 11 and 77 and elapid loops. Still further, the novel amino acid sequences of the present invention may in some instances include COOH-terminal amino acid extensions which can vary in length. In addition, because of the difference in the number of cysteine residues in the encoded amino acid sequences, those novel $PLA_2$s of the present invention that include 16 cysteine amino acid residues have been designated as Type III whereas those novel Type IV $PLA_2$s of the instant invention include 12 cysteines and have been designated at Type IV. Exemplary of Type, III $PLA_2$s of the present invention are the genes identified as $RPLA_2$-8 (rat) and partial $HPLA_2$-8 (human, as well as the $RPLA_2$-8 (rat) cDNA. Examples of Type IV $PLA_2$s of the present invention are the cDNAs identified as $RPLA_2$-10 (rat) and $HPLA_2$-10 (human).

In accordance with the present invention, a human $PLA_2$-encoding cDNA, which expresses $HPLA_2$-10, see FIG. 12, has been isolated from human brain RNA by RACE-PCR technique. The $HPLA_2$-10 cDNA also has been isolated from a human stomach cDNA library. In addition, two rat $PLA_2$ encoding cDNAs, designated $RPLA_2$-8 (FIG. 3) and $RPLA_2$-10 (FIG. 11), have been isolated from rat brain and heart cDNA libraries, respectively. The $RPLA_2$-10 is believed to be the counterpart of the $HPLA_2$-10. $RPLA_2$-10 and $HPLA_2$-10 share about 79% and 78% homology at the open reading frame nucleic acid and amino acid sequence levels, respectively. The mature enzyme encoded by the $HPLA_2$-10 clone has a calculated molecular weight of about 13,592, whereas the mature enzyme encoded by the $RPLA_2$-8 clone has a calculated molecular weight of about 14,673. As indicated, a partial human genomic counterpart to $RPLA_2$-8, $HPLA_2$-8 genomic DNA, has been isolated. See FIG. 19.

Comparison of the $RPLA_2$-8 amino acid sequence deduced from the cDNA sequence to Type I and Type II $PLA_2$s is shown in FIGS. 8 and 9. The significant structural features of the $RPLA_2$-8 protein are summarized in TABLE I. Seventeen (17) of the eighteen (18) absolutely conserved amino acids in all active 14 kDa $PLA_2$s are conserved in $RPLA_2$-18. $RPLA_2$-8 protein does not contain either a disulfide bridge between Cysteines 11 and 77 or an elapid loop, which are both characteristic of Type I $PLA_2$s. $RPLA_2$-8 protein, however, does include a seven amino acid COOH-terminal extension having the sequence GRDKLHC, as shown in FIG. 27, which is a characteristic of Type II $PLA_2$s as evidenced in FIGS. 22 and 27. Furthermore, unlike mammalian type I and II $PLA_2$s which have 14 cysteine amino acid residues, $RPLA_2$-8 protein includes 16 cysteine amino acid residues. It is therefore believed that $RPLA_2$-8 encodes a novel $PLA_2$, which has been designated as $PLA_2$ Type III.

The cDNAs of $RPLA_2$-10 and $HPLA_2$-10 are 1.8 kb (FIG. 11) and 1.1 kb (FIG. 12), respectively. A comparison between the deduced amino acid sequences from $RPLA_2$-10 and $HPLA_2$-10 is shown in FIG. 13. FIGS. 14 and 15 are comparisons between the $HPLA_2$-10 deduced amino acid sequence and those of Type I and II human $PLA_2$s, respectively. FIGS. 18 and 16 are comparisons between the $RPLA_2$-10 deduced amino acid sequence and those of Type I and II rat $PLA_2$s, respectively. A comparison between the deduced amino acid sequences from $RPLA_2$-10 and $RPLA_2$-8 is shown in FIG. 17. The major structural features of human and rat $PLA_2$-10 deduced amino acid sequences are listed in TABLE I. All eighteen (18) conserved amino acids in all of the active low-molecular weight, approximately 14 kDa, $PLA_2$s are conserved in both human and rat $PLA_2$-10 amino acid sequences of the present invention. Like the predicted $RPLA_2$-8 amino acid sequence, human and rat $PLA_2$-10 amino acid sequences also lack disulfide bridges between Cys-11 and 77 and elapid loops. However, $PLA_2$-10 amino acid sequences are believed to differ from $RPLA_2$-8 protein by having twelve (12) cysteine residues instead of sixteen (16). They further differ from $RPLA_2$-8 in that RPLA$_2$-10 does not have a COOH-terminal amino acid extension as depicted in FIG. 27 and HPLA$_2$-10 has only a single serine amino acid COOH-terminal extension as illustrated in FIG. 22. The PLA$_2$-10 proteins of the present invention have therefore been designated, as mentioned hereinbefore, as PLA$_2$ Type IV.

The present invention also contemplates antisense nucleotide sequences which are complementary to the genes and mRNA transcripts which encode for the Type III and Type IV PLA$_2$s. Exemplary of antisense sequences in accordance with the present invention are those which are complementary to the entire or portions of the nucleotide sequences set forth in FIGS. 3, 11, 12 and 19. It should therefore be understood that the present invention contemplates any antisense nucleotide sequence which may be useful in connection with inhibiting or interfering with the expression of the Type III and Type IV PLA$_2$ enzyme genes and mRNA transcripts therefor.

The above features and advantages will be better understood with reference to the FIGS. Detailed Description and Examples which are set out hereinbelow. It should be understood that the biological materials of this invention are exemplary only and are not to be regarded as limitations of this invention.

BRIEF DESCRIPTION OF THE FIGS.

Reference is now made to the accompanying FIGS. in which are shown characteristics corresponding to the novel mammalian 14 KD PLA$_2$s of the present invention from which certain of their novel features and advantages will be apparent:

Figure 4:
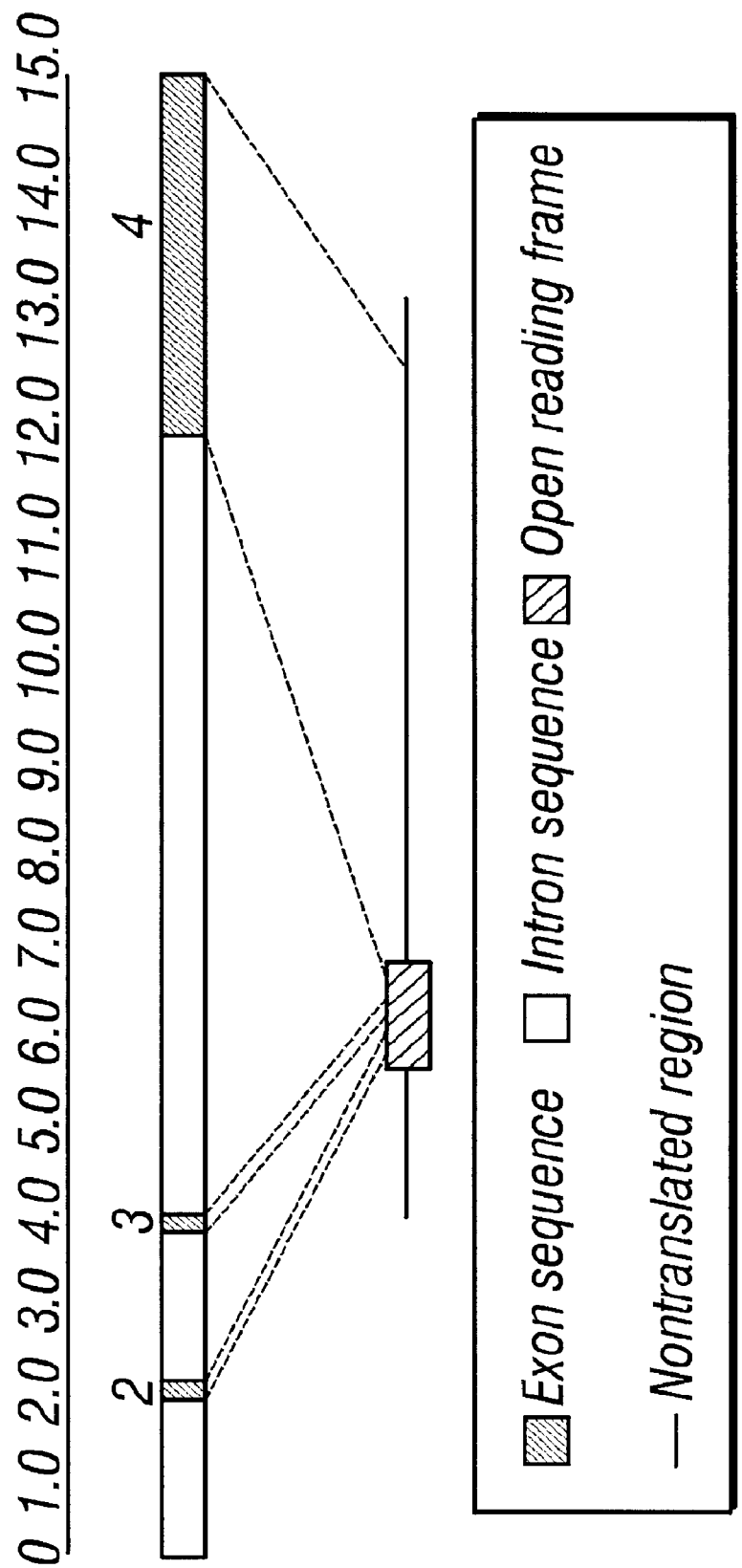
Figure 10:
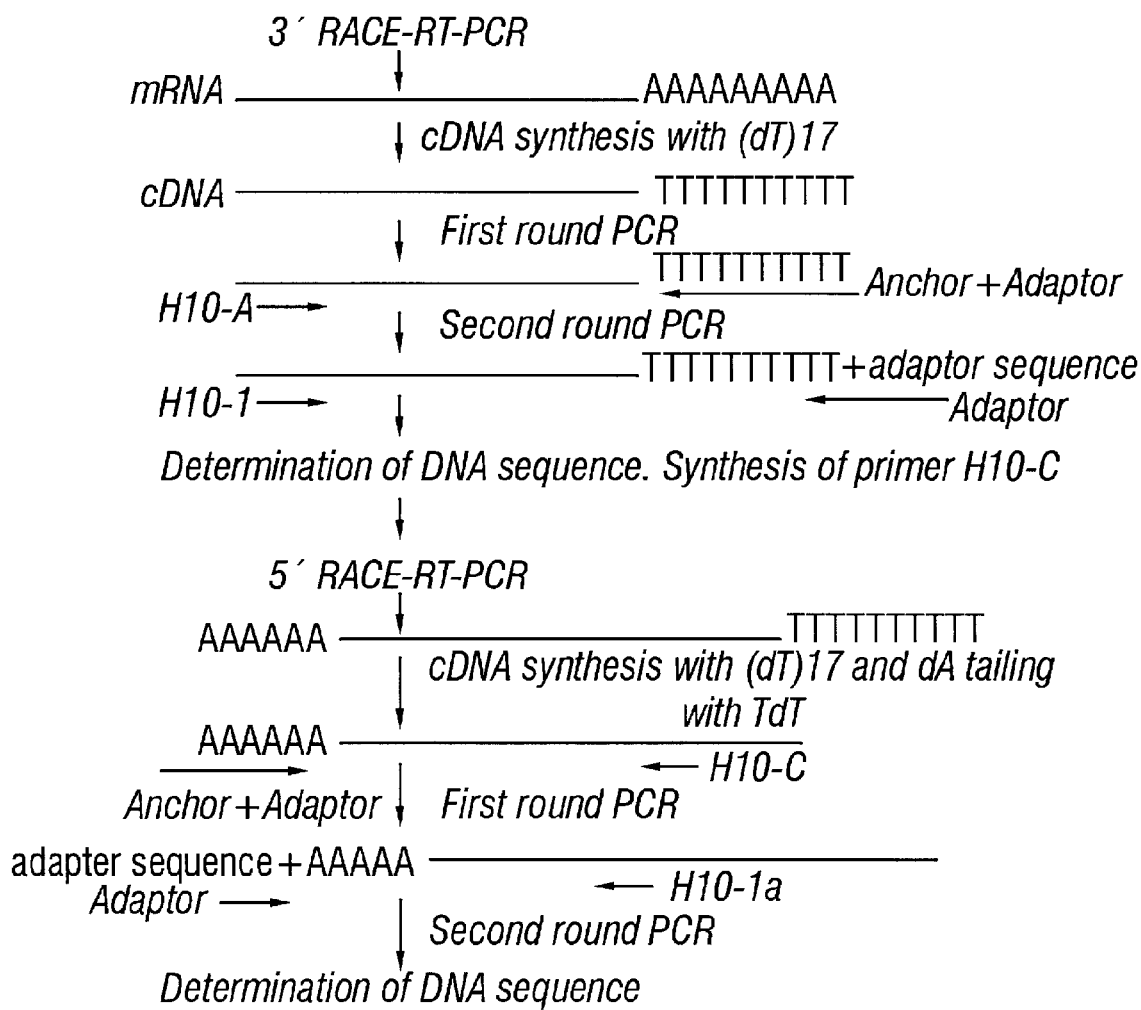

FIG. 3A–E depicts the RPLA$_2$-8 cDNA (SEQ ID NO: 21) and derived amino acid sequence (SEQ ID NO: 22) (the first and last eight (8) nucleotides are cloning linkers);

FIG. 4 depicts a diagram of the genomic DNA region containing exons 2, 3 and 4 of RPLA$_2$-8 in comparison to the corresponding cDNA;

FIG. 5 is a comparison between HPLA$_2$-8 Exon I (SEQ ID NO. 23) and RPLA$_2$-8 Exon I (SEQ ID. NO. 24) sequences;

FIG. 6 is a comparison between HPLA$_2$-8 Exon II (SEQ ID. NO. 25) and RPLA$_2$-8 Exon II (SEQ ID NO. 26) sequences;

FIG. 7 is a comparison between HPLA$_2$-8 Exon IV (SEQ ID. NO. 27) and HPLA$_2$-8 Exon IV (SEQ ID NO. 27) sequences;

FIG. 8 is a comparison of RPLA$_2$-8 deduced amino acid sequence (SEQ ID NO: 22) and rat PLA$_2$ Type I amino acid sequence (SEQ ID NO. 34);

FIG. 9 is a comparison of the RPLA$_2$-8 deduced amino acid sequence (SEQ ID NO. 22) and rat PLA$_2$ Type II amino acid sequence (SEQ ID NO. 35);

FIG. 10 depicts a flow diagram of 3' and 5' RACE-RT PCR techniques used to obtain a full length HPLA$_2$-10 sequence cDNA from brain mRNA;

FIG. 11A–C depicts the RPLA$_2$-10 cDNA sequence (SEQ ID. No. 29) and derived amino acid sequence (SEQ ID No. 30) showing primary cDNA sequence and various primer sequences, which are used in sequencing and synthesis, are underlined;

FIG. 12 depicts the HPLA$_2$-10 cDNA (Type IV) sequence (SEQ ID. No. 31) and derived amino acid sequence (SEQ ID No. 32 and a secondary (clone HPLA$_2$10-5) cDNA sequence which is slightly different at the 5' end and forshortened. Various primer sequences used in sequencing and synthesis are underlined.

FIG. 13 is a comparison between deduced amino acid sequences of HPLA$_2$-10 (SEQ ID NO. 32) and RPLA$_2$-10 (SEQ ID NO. 30);

FIG. 14 is a comparison between HPLA$_2$-10 deduced amino acid sequence (SEQ ID NO. 32) and human Type I amino acid sequence (SEQ ID NO. 36);

FIG. 15 is a comparison between HPLA$_2$-10 deduced amino acid sequence (SEQ ID NO. 32) and human PLA$_2$ Type II amino acid sequence (SEQ ID NO. 37);

FIG. 16 is a comparison between deduced amino acid sequences of RPLA$_2$-10 (SEQ ID NO. 30) and rat PLA$_2$ Type II amino acid sequence (SEQ ID NO. 35);

FIG. 17 is a comparison between deduced amino acid sequences of RPLA$_2$-10 (SEQ ID NO. 30) and RPLA$_2$-8 (SEQ ID NO. 22).

Figure 20:
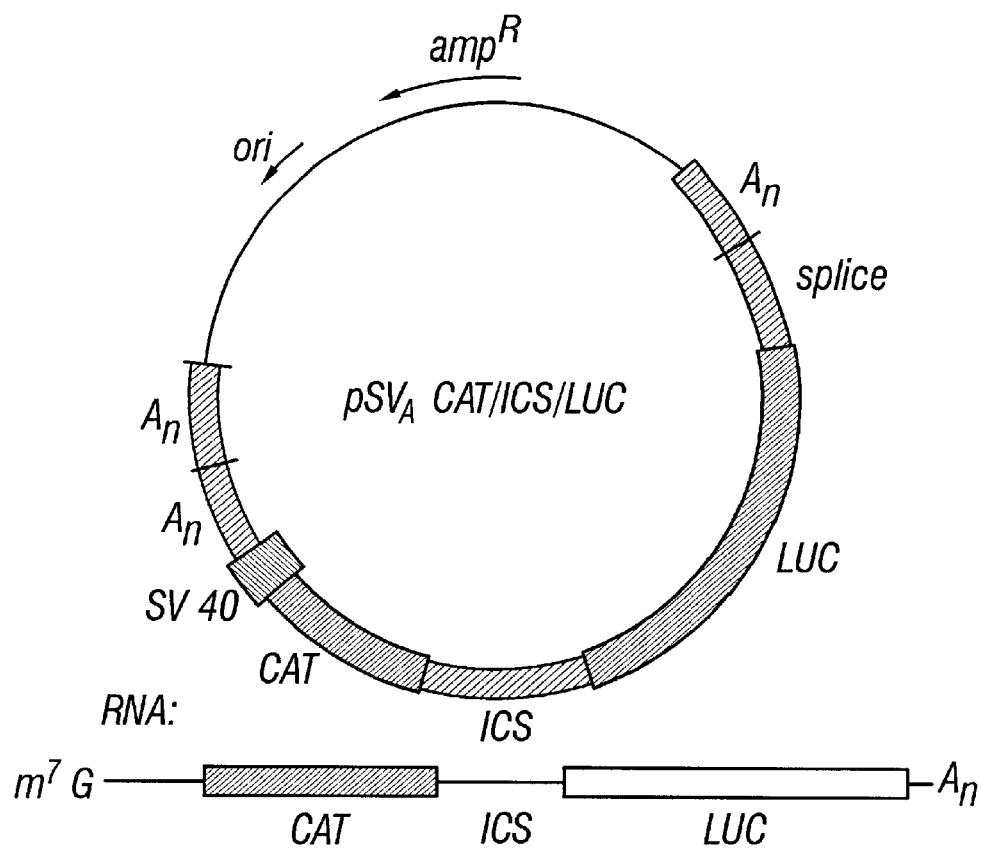
Figure 21:
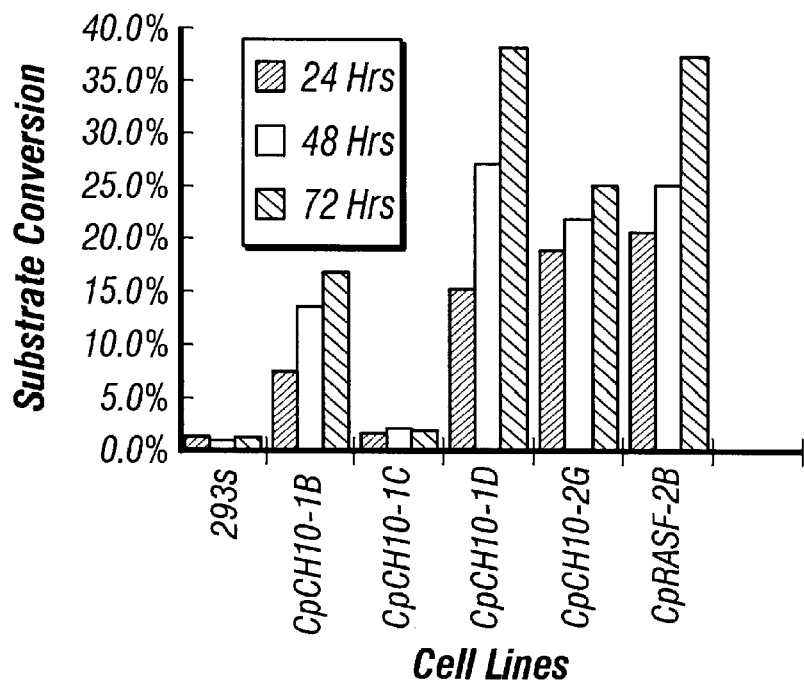

FIG. 18 is a comparison between deduced amino acid sequence of RPLA$_2$-10 (SEQ ID NO. 30) and rat PLA$_2$ Type I amino acid sequence (SEQ ID NO. 34);

FIG. 19A–O depicts the partial human genomic HPLA$_2$-8 DNA sequence (SEQ ID NO. 33). Putative exon 1 and exons 2 and 4 are underlined;

FIG. 20 depicts a diagram of the vector to express discistronic mRNA. The chloramphenicol acetyl transferase and luciferase reporter genes are indicated by boxes. The intercistronic sequence that is replaced by part of RPLA$_2$-8 is shown;

FIG. 21 illustrates PLA$_2$ activity of expressed HPLA$_2$-10 cDNA. pCH10 is HPLA$_2$-10 cDNA cloned into an Epstein Barr virus-based expression vector. CpCH10-1B, CpCH10-1C, CpCH10-1D and CpCH20-2G are independent cell lines which express plasmid pCH10. The CpRASF-2B is a cell line which expresses plasmid pRASF into which a known human PLA$_2$ Type II gene has been cloned.

Figure 23:
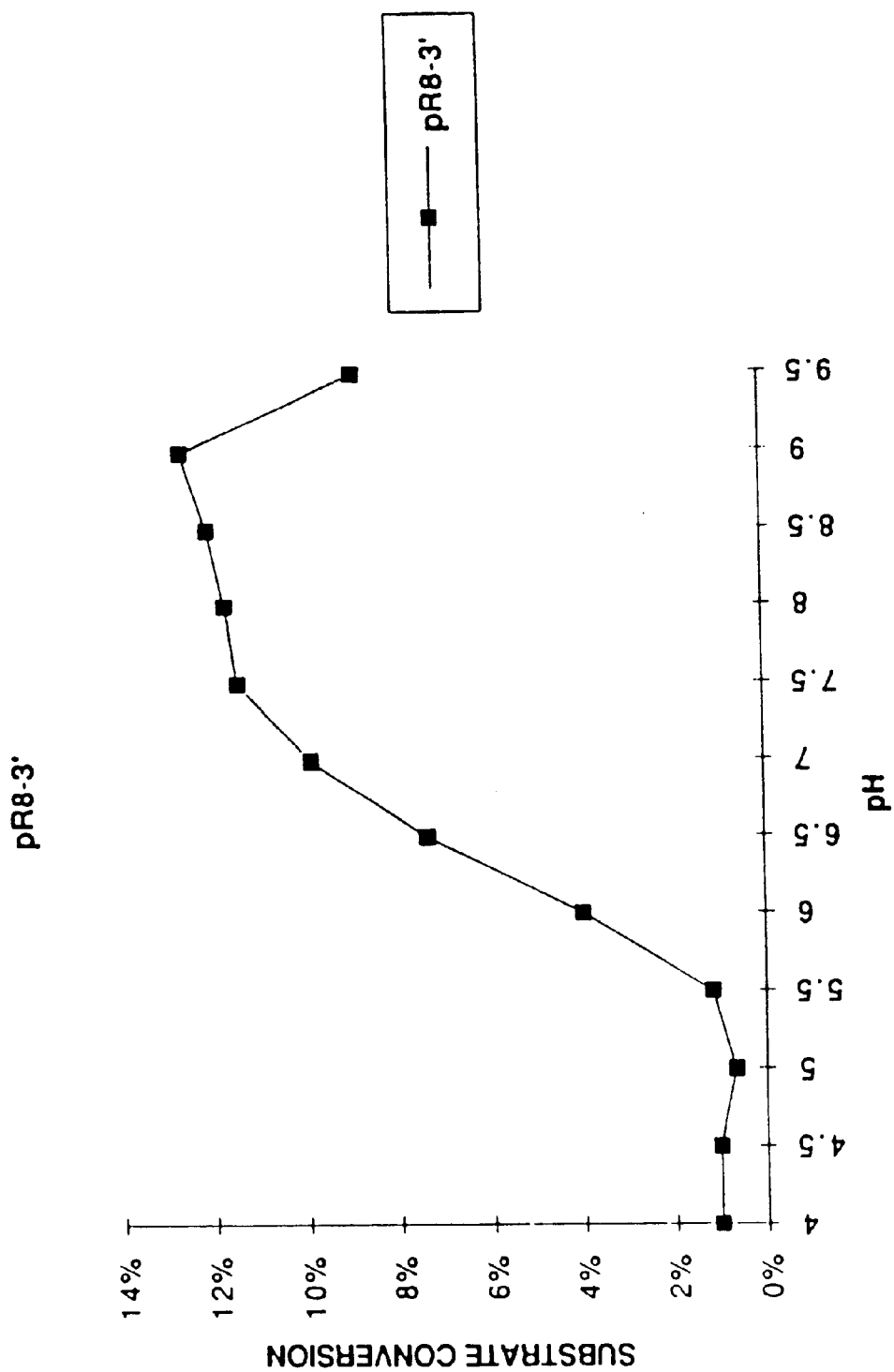
Figure 24:
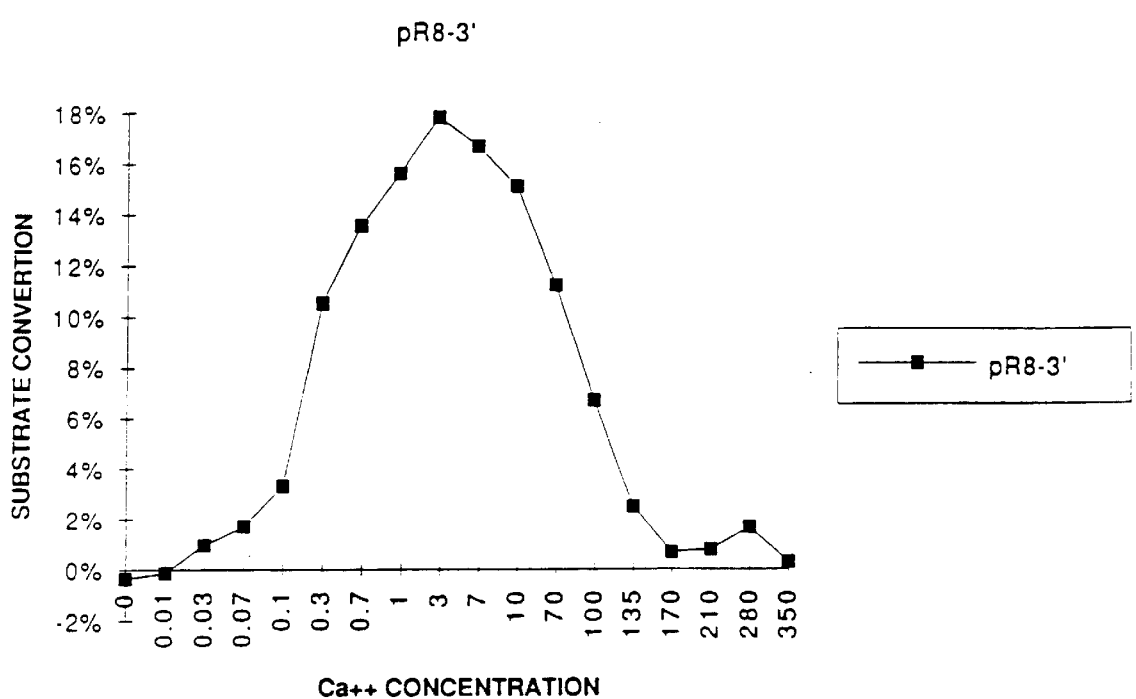
Figure 25:
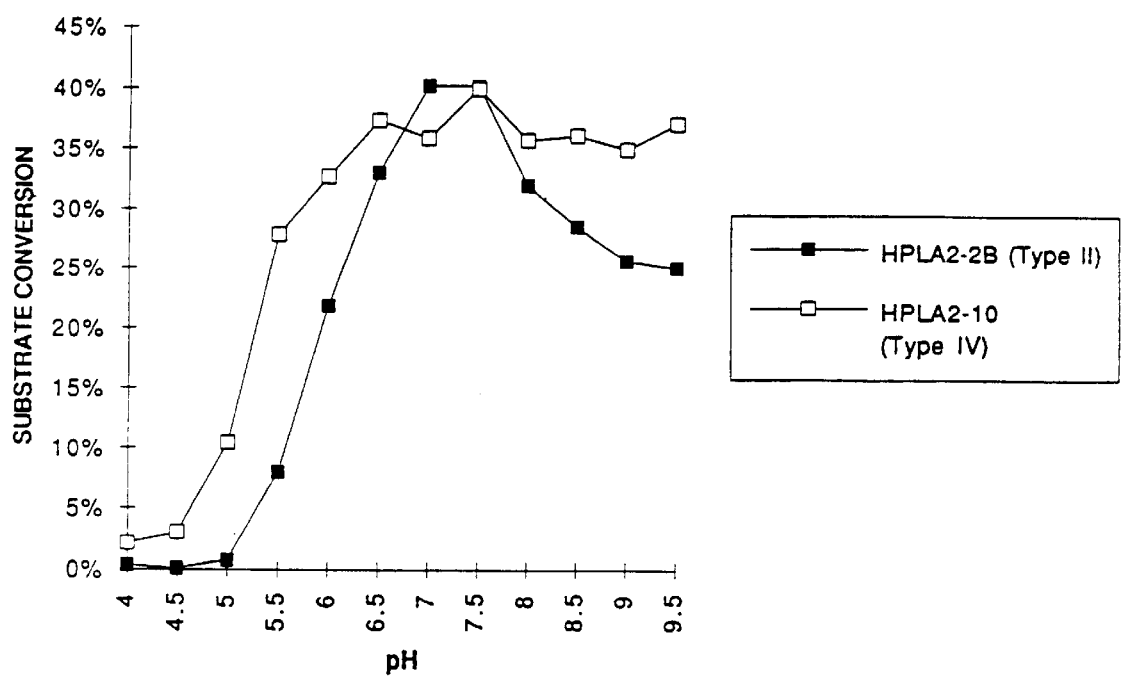
Figure 26:
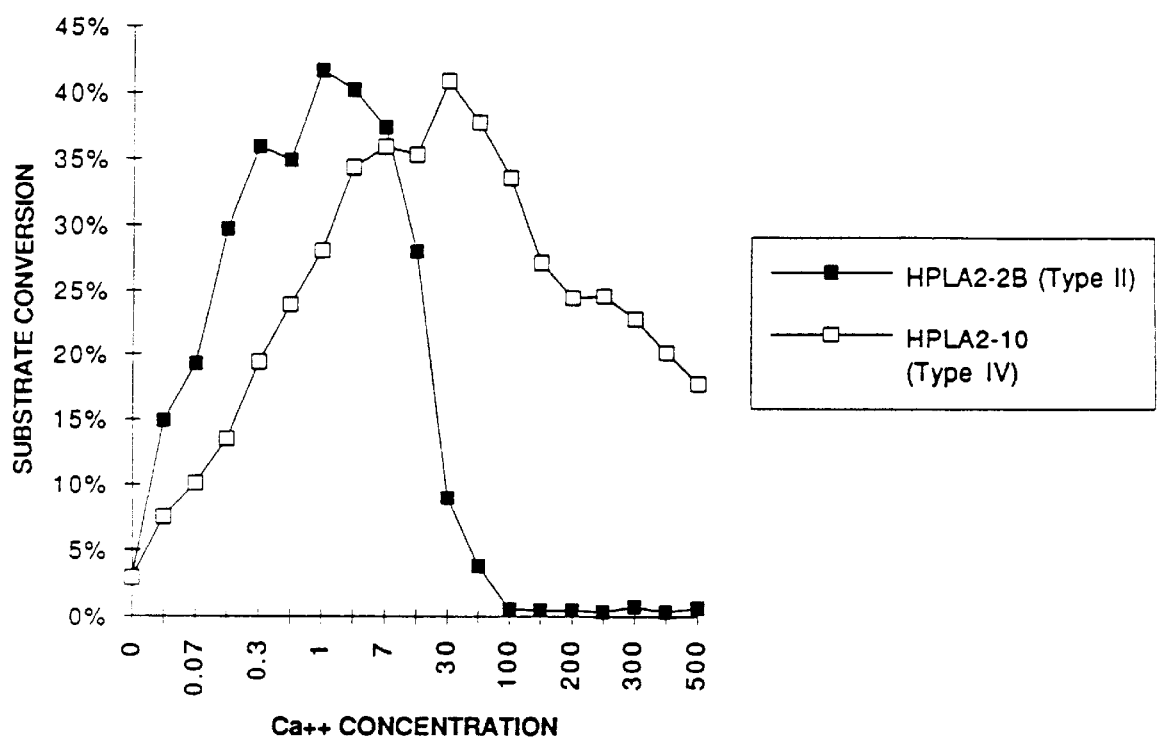

FIG. 22 depicts an alignment of amino acid sequences of human (SEQ ID Nos. 38, 19, 40, 44, and 43) PLA$_2$. Asterisks denote eighteen residues that have been conserved among all active PLA$_2$ sequences. The COOH-terminal amino acid extensions have been underscored;

FIG. 23 depicts the effects of pH on PLA$_2$ activity of RPLA$_2$-8 encoded enzyme (Type III). More particularly, FIG. 23 depicts the effects of pH on PLA$_2$ activity of RPLA$_2$-8 enzyme expressed by cell line CpR8-3'. The CpR8-3' cell line expresses plasmid pR8-3' which includes the coding region for the mature RPLA$_2$-8 protein (bases 806–1200) which is preceded by the signal peptide of pRASF (bases 131–196). Assay for PLA$_2$ activity is as indicated herein and in Elsbach, P. et al.: *Methods in Enzymology*, 197:24–31(1991);

FIG. 24 depicts the effects of calcium on PLA$_2$ activity of RPLA$_2$-8 encoded enzyme (Type III). More particularly, FIG. 24 depicts the effects of calcium on PLA$_2$ activity of RPLA$_2$-8 enzyme expressed by cell line CpR8-3'. The CpR8-3' cell line expresses plasmid pR8-3' which includes the coding region for the mature RPLA$_2$-8 protein (bases 806–1200) which is preceded by the signal peptide of pRASF (bases 131–196). Assay for PLA$_2$ activity is as indicated herein and in Elsbach, P. et al.: *Methods in Enzymology*, 197:24–31(1991);

FIG. 25 depicts the effects of pH on $PLA_2$ activity of $HPLA_2$-10 encoded enzyme (Type IV). More particularly, FIG. 25 depicts the effects of pH on $PLA_2$ activity of $PLA_2$ Type II enzyme expressed by cell line CpRASF-2B and of $PLA_2$ Type IV enzyme expressed by cell line CpCH10-1D. The CpRASF-2B cell line expresses plasmid pRASF into which a known human $PLA_2$ Type II gene has been cloned. The CpCH10-1D cell line expresses plasmid pCH10 into which the $HPLA_2$-10 cDNA has been cloned. Assay for $PLA_2$ activity is as indicated herein and in Elsbach, P. et al.: *Methods in Enzymology*, 197:24–31 (1991);

FIG. 26 depicts the effects of calcium on $PLA_2$ activity of $HPLA_2$-10 encoded enzyme (Type IV). More particularly, FIG. 26 depicts the effects of calcium on $PLA_2$ activity of $PLA_2$ Type II enzyme expressed by cell line CpRASF-2B and of $PLA_2$ Type IV enzyme expressed by cell line CpCH10-1D. The CpRASF-2B cell line expresses plasmid pRASF into which a known human $PLA_2$ Type II gene has been cloned. The CpCH10-1D cell line expresses plasmid pCH10 into which the $HPLA_2$-10 cDNA has been cloned. Assay for $PLA_2$ activity is as indicated herein and in Elsbach, P. et al.: *Methods in Enzymology*, 197:24–31 (1991); and FIG. 27 depicts an alignment of amino acid sequences of rat Types I, II, $RPLA_2$-8 and $RPLA_2$-10 $PLA_2$s (SEQ ID Nos. 41, 42, 43, 44). Asterisks denote eighteen residues that have been conserved among all active $PLA_2$ sequences. The COOH-terminal amino acid extensions have been underscored.

DETAILED DESCRIPTION

By way of illustrating and providing a more complete appreciation of the present invention and many of the attendant advantages thereof, the following detailed description is provided concerning the novel mammalian $PLA_2$ nucleotide sequences, the low molecular weight amino acid sequences encoded thereby, clones, vectors, antisense nucleotide sequences, nucleotide sequences having internal ribosome binding sites, and cell lines.

Figure 1:
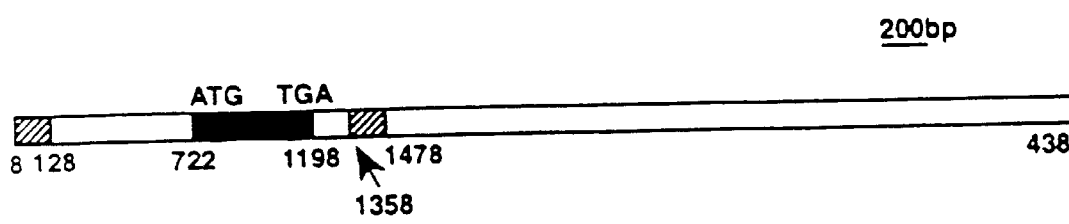
FIG. 1 depicts a diagram of RPLA$_2$-8 cDNA showing positions of open reading frame coding region, repeats, and 5' and 3' termini (the first and last eight (8) nucleotides are cloning linkers)
Figure 2:
FIG. 2 depicts a postulated secondary structure of RPLA$_2$-8 cDNA showing a stem and a loop containing the open reading frame coding region.

In accordance with the present invention, a 4.4 kb cDNA containing the r8 fragment, a rat genomic fragment containing sequences homologous to h8 fragment, is isolated from a rat fetal brain cDNA library. See FIG. 1. This cDNA is about five-times larger than any mammalian $PLA_2$ cDNA known to date. Uniquely, the entire coding region is contained on a putative 1 kb loop flanked by 121 bp inverted perfect repeats, leaving about a 3 kb 3' "tail." See FIG. 2. The sequence of the entire cDNA is shown in FIG. 3. The size of the gene is about 15 kb. See FIG. 4. A preliminary screen of some rat tissues by reverse transcription and PCR (RT-PCR), using primers Pla8-1 and Pla8-4, reveals the pattern of $RPLA_2$-8 gene expression indicated in Table I.

TABLE I

Characteristics of Type III and IV $PLA_2$s

| | Pre* | Pro* | Mature* |
|---|---|---|---|
| Hum Type I | MKLLVLAVLLTVAAA | DSGISPR | AVWQF |
| Hum Type II | MKTLLLAVIMIFGLLQAHG | | NLVNF |
| Rat Type III | MDLLVSSGMKGIAVFLVFIFC | (WTTSTLS) | SFWQF |
| Hum Type IV | MKGLLPLAWFLACSVPAVQG | | GLLDL |
| Rat Type IV | MKRLLTLAWFLACSVPAVPG | | GLLEL |

Human Type I PLA2 has a 7 residue propeptide, human Type II does not. Human and rat Type IV are like Type II; Rat Type III might encode a 7 residue propeptide.
\* depicts the $NH_2$-terminal amino acids in the amino acid sequences for the respective prepeptides, propeptides and mature peptides.

| Conserved Characteristics of Pre, Pro and Mature Peptides: | |
|---|---|
| Rat Type III | Human and Rat Type IV |
| Phe5 | Ile9 |
| Met8 | Met8 |
| YGCYCG $Ca^{2+}$ binding loop | YGCYCG $Ca^{2+}$ binding loop |
| His48, Asp49 active site | His48, Asp49 active site |
| Position of Cys residues (disregarding the two extra Cys residues) | Position of Cys residues (disregarding the two missing Cys residues) |

| Unusual Characteristics of Pre, Pro and Mature Peptides: | |
|---|---|
| Rat Type III | Human and Rat Type IV |
| Val9 | Leu5 |
| Two extra Cys residues | Two missing Cys residues |
| Ala 102, 103 missing | Ala 102, 103 missing |
| Unusually large variable peptide loop | |

| Other Characteristics of Pre, Pro and Mature Peptides: | |
|---|---|
| Rat Type III | Human and Rat Type IV |
| No elapid loop | No elapid loops |
| No disulphide bridge between Cys 11 and 77 | No disulphide bridges between Cys 11 and 77 |
| Sixteen Cys residues | Twelve Cys residues |
| Seven COOH-terminal amino acid extension-GRDKLHC | Human Type IV-one serine COOH-terminal extension Rat Type IV-no COOH-terminal amino acid extension |

\*\*The numbers designating the positions for the amino acids in Table I are for the mature peptides.

Moreover, according to Northern Blot data of several tissues, a $RPLA_2$ mRNA is detected in only the testis indicating that the $RPLA_2$-8 gene is testis specific, as reported in Table II.

TABLE II

Northern blot data

| Type IV (cl 10) human | |
|---|---|
| brain | – |
| heart | +++ |
| kidney | – |
| liver | – |
| lung | + |
| pancreas | – |
| placenta | ++ |
| skeletal muscle | – |
| spleen | – |
| testis | – |

| Type IV (cl 10) rat | | Type III (cl 8) rat |
|---|---|---|
| brain | – | – |
| heart | ++ | – |
| kidney | – | – |

TABLE II-continued

Northern blot data

| | | |
|---|---|---|
| liver | − | − |
| lung | ? | − |
| skeletal muscle | − | − |
| spleen | − | − |
| testis | − | ++ |

Using parts of RPLA$_2$-8 as probes, a partial human genomic clone which is homologous to rat genomic clone is identified. See FIG. 19. To date, all but the third of the four exons in the human genomic DNA, see FIGS. 5–7, is identified and sequenced. The 3' flanking regions of the human and rat genes show very significant homology (about 50 percent) for about 500 bp. This conservation is unusual and suggests functional importance. It is functionally demonstrated that RPLA$_2$-8 cDNA contains an internal ribosome binding site that enables internal translation initiation.

A comparison of the significant structural features of the putative protein encoded by RPLA$_2$-8 cDNA sequence and encoded amino acid sequence to those of the corresponding pancreatic and non-pancreatic PLA$_2$ enzymes are shown in FIGS. 8 and 9. Pancreatic PLA$_2$ is known as Type I and the non-pancreatic PLA$_2$ is designated as Type II. It is believed that PLA$_2$-8 encodes a novel PLA$_2$ which is designated as Type III. An enzyme encoded by a gene containing the h10a sequence is designated Type IV (see below). The proximity (within about a million base pair region in the mouse) of the genes for Types III and IV to the PLA$_2$ Type II gene suggests a common evolutionary origin as does their localization to the same band on human chromosome 1. Further, Types II, III and IV are likely to be members of a gene family and may represent isozymes. However, a homology comparison indicates that the RPLA$_2$-8 protein is relatively distant, evolutionarily, from both Type I and Type II PLA$_2$ enzymes, but is believed to be probably closer to Type II.

In accordance with the present invention, human cDNA that contains the h10a fragment and rat cDNA that contains the rat counterpart are isolated. See FIGS. 11 and 12. The predicted protein sequences of HPLA$_2$-10 and RPLA$_2$-10 and comparisons to each other and Types I and II are shown in FIGS. 13–17. Some of the significant structural features of the proteins encoded by these cDNAs are shown in TABLE I. Importantly, the 18 amino acids that are believed to be requisite for PLA$_2$ function are conserved in both predicted proteins. See FIG. 22. This fact, plus the high degree of conservation between species, suggests that these Type IV proteins play an important role in phospholipid metabolism and processes such as membrane structuring, inflammation and intracellular signaling.

The amino acid sequences of the present invention may be produced by, for example, recombinant technology, chemical synthesis or any other methods available in the art so long as the methodology selected does not interfere with their utilities. Likewise, the nucleotide sequences of the instant invention may be produced by, for instance, PCR technology, chemical synthesis or any other methods available in the art so long as the methodology selected does not interfere with their utilities. Moreover, amino acid residues may be deleted or added or alternative amino acid residues may be substituted for those recited in the amino acid sequences of the instant invention so long as such changes do not defeat the utilities of such amino acid sequences. Still further, it should be appreciated that the present invention contemplates any amino acid sequences which are equivalent to or constitute active fragments of the amino acid sequences for the Type III and Type IV PLA$_2$ enzymes of the present invention. Of course, corresponding or other changes may be made to the nucleotide sequences of the present invention to accomplish the objectives of this invention.

It should also be appreciated that the present invention contemplates a.) any antisense nucleotide sequences which are capable of inhibiting or interfering with expression of genes and mRNA transcripts encoding Type III and Type IV PLA$_2$ enzymes of the present invention, including any amino acid sequences that are equivalent thereto or active fragments thereof, and b.) any nucleotide sequences having bases 116–720 of FIG. 3 and any equivalent fragments thereto or active fragments thereof that allow for internal initiation of mRNA cap-independent translation. Like other nucleotide sequences of the present invention, substitutions, deletions and additions may be made to the antisense nucleotide sequences and the nucleotide sequences having internal ribosome binding sites of the present invention so long as the objectives of the present invention are not defeated.

HPLA$_2$-10

In order to clone an cDNA containing the putative HPLA$_2$ exon, two primers, HClo10-1 and HClo10-1a, are generated according to the 120 bp presumptive exon II sequence. See FIG. 12. PCR amplification with these primers is used to screen human child brain, adult brain, liver, heart, and various white cell cDNA libraries. PCR amplification products are not obtained.

Since zoo blots have indicated that this putative exon is evolutionarily conserved, a rat genomic cosmid library (Clontech, Inc.) is screened using a PCR-generated copy of the HClo10-1—HClo10-1a fragment as a probe. Three unique positive clones are identified. Southern blot anaysis of the three EcoRI-digested clones using the HClo10-1—HClo10-1a fragment as a probe identifies a common 5 kb band. This band is subcloned into EcoRI-digested pUC13 and sequenced. A region (rat-10 putative exon II) in the 5 kb sequence highly homologous to h10a is identified by computer analysis.

In order to search for the presence of exon I, the 5 kb human genomic DNA clone containing putative exon II is sequenced completely. Computer analysis of the sequence identified two highly homologous regions. One appears to be exon II. It contains a consensus splice acceptor site at its 5' end and a consensus splice donor site at its 3' end. The other region, located about 1.2 kb 5' of the exon II, contains a consensus splice donor site at its 3' end and a putative in-frame ATG start codon at its 5' end. It is likely to be exon I. Furthermore, when these two putative exons are joined together using the assumed splice donor and acceptor sites, the resulting sequence encodes a signal peptide and 41 amino acids which have significant homology to the amino terminus of known, mature PLA$_2$s.

After determining the putative exon I sequence, H10-A, a 5' primer located within exon I, and H10-1a, a 3' primer located within exon II, see FIG. 12, are used for RT-PCR of total human brain and lymphoblast RNA. A unique 140 bp band from both PCR reactions is sequenced. The 140 bp contains coding exons I and II, but not the putative intron I of HPLA$_2$-10. 5' and 3' RACE-RT PCR techniques, Frohman, M. A. et al.: PNAS, 85:8998–9002 (1988); O'Hara, O. et al.: PNAS, 86:6883–6887 (1989); and Loh, Y. et al.: Science, 243:217–220 (1989), are then used to generate the full length cDNA sequence from total human brain RNA. See FIG. 10. The entire cDNA sequence, designated HPLA$_2$-10, is shown in FIG. 12. Exon-intron junction sites are determined by genomic DNA analysis. Since the genomic DNA clone containing the first 120 bp of HPLA$_2$-10 is not obtained, it has not been determined if there are any introns in this region of the HPLA$_2$-10 genomic sequence. If no additional exons are found, HPLA$_2$-10 will apparently have an exon-intron structure typical of known Type II PLA$_2$s with a 5' untranslated exon followed by four protein coding exons.

Primers H10-A (bases 149–170) and H10-C (bases 520–548) are used to screen by PCR amplification a human stomach cDNA library (Clonetech, Inc.). A 399 bp and a 290 bp PCR amplification product are obtained only from the stomach cDNA library. The two PCR fragments are cloned into pUC19 and sequenced. The sequence of the 399 bp fragment is identical to the HPLA$_2$-10 RACE-RT PCR generated cDNA sequence from bases 148 to 541. The 290 bp fragment is identical to the 399 bp fragment except that it is missing bases 316 to 422 which encompass the 5' end of exon III. See FIG. 11. The same two PCR fragments are also amplified from total human brain and lymphocyte RNA using primers H10-A and H10-C. The 290 bp PCR product is much less abundant than the 399 bp product when amplified from human stomach and brain RNA and stomach cDNA library. Since the 290 bp product codes only for the signal peptide and the first 41 amino acids of the mature protein because of an in-frame stop codon immediately following the 41st amino acid, the in vivo significance of this product is unknown at this time.

Using the 399 bp PCR product as a probe, $6 \times 10^5$ individual plaques from the human stomach cDNA library are screened. Four positive clones are identified. The clones, designated HPLA$_2$-10-2, -3, -5, -7, have inserts of 1.4, 2.3 0.9, and 0,8 kb, respectively. The inserts of these clones are released by EcoRI digestion, subcloned into pUC19 and sequenced completely. HPLA$_2$-10-2 contains exon I-intron I-exon II of HPLA$_2$-10; HPLA$_2$-10-3 contains intron III-exon IV-intron IV of HPLA$_2$-10. The sequences of both HPLA$_2$-10-5 and HPLA$_2$-10-7 are identical to the corresponding regions of the RACE-RT-PCR generated HPLA$_2$-10 sequence except that the 5' end of the HPLA$_2$-10-5 starts at base 142 of the RACE-RT-PCR sequence and the 5' end of HPLA$_2$-10-7 starts at base 23.

To determine the transcription pattern of HPLA$_2$-10, a Human Multiple Northern Blot (Clontech, Inc.) is probed with a 399 bp fragment, i.e., HPLA$_2$-10 PCR probe, generated by PCR with primers H10-A (bases 149–170) and H10-C (bases 520–548). As seen in TABLE II, a 1.2 kb transcript is detected in heart and, less abundantly, in liver and lung RNA. In addition, a 2 kb transcript is detected in placental RNA. This suggests that the expression of HPLA$_2$-10 is not only tissue specific, but that alternative forms of the protein may be expressed in different tissues. The 2 kb transcript seen in placental RNA may result from the use of a different promoter, alternative splicing or the use of an alternative poly A site.

The HPLA$_2$-10 cDNA encodes a mature protein of about 118 amino acids with a calculated molecular mass of about 13,592 Daltons. The amino acid sequence has significant homology to known PLA$_2$s. All of the 18 invariantly conserved amino acids in known active low molecular weight PLA$_2$s, see Davidson, F. F.: *J. Mol. Evolution*, 31:228–238 (1990), are conserved in this novel protein. See FIG. 22. However, HPLA$_2$-10 contains neither the disulfide bridge between Cys 11 and 77 nor the elapid loop characteristic of Type I PLA$_2$s. HPLA$_2$-10 does, however, contain a single serine amino acid COOH-terminal extension, as shown in FIG. 22, which is more characteristic of a Type I than Type II PLA$_2$. As depicted in FIG. 22, Human Type I has a two amino acid COOH-terminal extension whereas Human Type II has a seven amino acid COOH-terminal extension. Furthermore, unlike mammalian Types I and II PLA$_2$s which have 14 cysteine residues, this putative HPLA$_2$ only has 12. The overall homology between HPLA$_2$-10 and a consensus Type I PLA$_2$ is about 30.5% while the overall homology between HPLA$_2$-10 and a consensus Type II PLA$_2$ is about 40.6%. The predicted isoelectric point (pI) of this protein is about 6.2 while that of other known Type II PLA$_2$s is about 10.5.

To test whether this HPLA$_2$-10 gene encodes an active, secreted PLA$_2$, an Epstein Barr virus-based expression vector (pCEP) is used to express the HPLA$_2$-10 cDNA in human 293s cells. pCEP contains two regions of the EBV genome required for episomal maintenance (EBNA-1 and OriP), a drug resistance gene for selection in human cells (hyg), bacterial sequences for maintenance in *E. coli*, a drug resistance gene for selection in *E. coli* (amp), and an expression cassette for the production of high levels of mRNA from an introduced sequence by using an Rous/Sarcoma virus long terminal repeat (RSV LTR) promoter and an Simian virus 40 (SV40) polyadenylation signal. HPLA$_2$-10-5', a 5' primer beginning at base 126 of HPLA$_2$-10 and containing a 10 nucleotide NheI linker at its 5' end, and HPLA$_2$-10-3', a 3' primer ending at base 555 and beginning with a 10 nucleotide XhoI linker, are used for reverse-transcriptase-polymerase chain reaction (RT-PCR) of total human brain RNA to generate the appropriate cDNA insert. The PCR product is blunt-end ligated to HincII-digested pUC19 and sequenced. The insert is then released by digestion with NheI and XhoI and is cloned into the NheI-XhoI sites of pCEP. The resulting plasmid is designated pCh10.

A known human Type II PLA$_2$ cDNA is cloned into pCEP for use as a positive control. PCR primers RASF-5' and RASF-3' are used to amplify bases 130 to 581 of pRASF, a plasmid containing the entire human known PLA$_2$ Type II cDNA. See Seilhamer, J. J.: *J. Biol. Chem.*, 264:5335–5338 (1989). The resulting plasmid is designated pRASF and is used as a control. The HPLA$_2$-2B (Type II) enzyme, as depicted in FIGS. 25 and 26, are expressed by pRASF and used as a control.

Purified plasmid DNA is transfected into human 293s cells which are selected in DMEM containing 200 ug/ml hygromycin. Medium samples from multiple cell lines transfected with either pCH10, pR8-3' or pRASF are then assayed for PLA$_2$ activity. See FIG. 21. PLA$_2$ activities derived from cell lines transfected with plasmids pCH10, pR8-3', and pRASF are accumulated in the medium. Neither 293s cells nor multiple cell lines transfected with an unrelated PLA$_2$ cDNA inactivated by a one base pair deletion at the 5' end of the mature protein show detectable PLA$_2$ activity in the medium even after 72 hours. Cell lysates that are prepared by sonication from cells stably transfected with either pCH10 or pRASF show approximately 50% of the activity of 72 hour medium samples.

Two cell lines, CpCH10-1D expressing pCH10 and CpRASF-2B expressing pRASF, are chosen for comparative study. The pH profile for the enzyme expressed by the cell lines is shown in FIG. 25. PLA$_2$ activity of HPLA$_2$-10 starts at about pH 5 and significant activity is reached at between about pH 6.5 and about pH 7.5 and remains relatively steady up to at least about pH 9.5, whereas the control Type II PLA$_2$ reaches peak activity at between about pH 7.0 and about pH 7.5 and then progressively declines.

Calcium concentration versus enzyme activity profiles for CpCH10-1D and CpRASF-2B are shown in FIG. 26. HPLA$_2$-10 appears to be a calcium-dependent. PLA$_2$ having activity starting at about 0.07 mM Ca$^{2+}$ amd reaching maximal activity at between about 7 mM and about 100 mM Ca$^{2+}$. The activity of HPLA$_2$-10 then slowly decreases, but maintains significant activity, as the Ca$^{2+}$ concentration approaches about 500 mM or more. This profile differs from that of the control cell line CpRASF-2 (Type II PLA$_2$) which shows maximal activity at between about 0.5 mM and 3.0 mM Ca$^{2+}$ and becomes inactive at Ca$^{2+}$ concentrations at about 100 mM or greater. Since HPLA$_2$-10 expresses at least half of its maximal activity at Ca$^{2+}$ concentrations between 1 and 100 mM, similar to previously described Type II phospholipases, see Marshall: *Biochemical Pharmacology*, V. 44:1849–1858 (1992), it is likely that HPLA$_2$-10 is capable of functioning at concentrations found intracellularly (0.1 to 2 $\mu$M) and extracellularly (1 mM).

RPLA$_2$-8

Two PCR primers, Pla8-1 and Pla8-2 (FIG. 3), are generated using the reported rat r8 presumptive exon II sequence. See Seilhamer, J. J. et al.: *J. Cell. Biochem.*, 39:327–337 (1989). Four size-fractionated, newborn rat brain cDNA λZAPII libraries (two 0.5–1.5 kb, one 1.5–4 kb, and one greater than 4 kb, provided by Dr. L. Yu, Indiana School of Medicine, are directly amplified by PCR, See Friedman, K. D.: et al.: *Nucleic Acids Research;* 16:8718 (1988), using primers pla8-1 and pla-2. Only the >4 kb insert library gives the proper size 120 bp fragment prediced by the Clo8 DNA sequence. The band is purified from an agarose gel using a QIAEX gel extraction kit (QIAGEN), cloned into m13mpl18, and is sequenced using a Sequenase kit (USB). The sequence data confirms the proper identity of the PCR product. A total of 10$^6$ individual clones from the cDNA library are screened using the PCR product as a probe. Only two clones hybridize. The restriction maps of the two clones are believed to be identical. One of them, clo8-2, is sequenced completely. The sequence, designated RPLA2-8, is shown in FIG. 3.

RPLA$_2$-8 is a 4.4 kb cDNA, which is about five-times larger than any known mammalian 14kDa PLA$_2$ cDNA. See Seilhamer, J. J. et al.: *DNA*, 5:519–527 (1986); Seilhamer, J. J. et al.: *J. Biol. Chem.*, 264:5335–5338 (1989); Ohara, O. et al.: *Proc. Natl. Acad. Sciences U.S.A.*, 86:6883–6887 (1989); Kramer, R. M. et al.: *J. Biol. Chem.*, 264:5768–5775 (1989); and Komada, M. et al.: *J. Biochem.*, 106:545–547 (1989). The 480 bp coding region is believed to be contained in a putative 1.2 kb loop flanked by 121 bp perfect inverted repeats. See FIG. 2. This stem-loop is flanked by perfect 121 bp inverted repeats. This stem-loop structure leaves about 3 kb of 3' "tail." See FIGS. 1 and 2. Translation of RNAs containing such a secondary structure cannot readily be explained by the conventional translation scanning model. See Pain, V. M.: *Biochemistry J.*, 235:625–637 (1986). Nevertheless, it is believed that there is an internal ribosome binding site between the 5' repeat sequence and ATG translation start site. Cloning the sequence between base 116 and 720, see FIG. 3, in both normal and reverse orientations in front of an internal luciferase gene which lies downstream of a CAT gene, see Macejjak, D. G. et al.: *Nature*, 353:90–94 (1991), see FIG. 20, followed by detecting luciferase gene expression in transfected Hela cells (with positive and negative control constructs), confirms that the fragment does contain a internal ribosome binding sequence. Luciferase expression is significantly higher when the fragment is cloned in normal orientation then in reverse orientation. It is believed that the translation of mRNAs initiated by an internal ribosome binding mechanism may play an important role in mitosis, meiosis or specific viral infection, because cap-dependent translation during mitosis in mammalian cells is unlikely, due to the presence of underphosphorylated and therefore nonfunctional translation initiation factor, eif-4F. See Macejjak, D. G. et al.: *Nature*, 353:90–94 (1991). It is therefore believed that the RPLA$_2$-8 gene product could play a role during these processes.

As a preliminary study, the pattern of RPLA$_2$-8 gene expression, see TABLE III, is examined by screening rat tissues with reverse transcription followed by PCR (RT-PCR), using primers pla8-1 and pla8-2. See FIG. 3.

TABLE III

Reverse Transcription-PCR (RT-PCR) of Total RNA of Different Rat tissues by Primers Clo8-1 and Clo8-1a

| | | |
|---|---|---|
| 1. | Brain | + |
| 2. | Cerebellum, Brain Stem | + |
| 3. | Kidney | + |
| 4. | Lung | + |
| 5. | Heart | + |
| 6. | Muscle (?) | + |
| 7. | Pancreas | – |
| 8. | Small intestine | – |
| 9. | Liver | – |
| 10. | Prostate | – |
| 11. | Bladder | – |
| 12. | Spleen | – |
| 13. | Adrenal | – |
| 14. | Submaxillary | – |

In addition, to determine transcription patterns of RPLA$_2$-8 and RPLA$_2$-10, a Rat Multiple Northern Blot (Clontech, Inc.) is probed with a 489 bp fragment, i.e., RPLA$_2$-8 PCR probe, generated by PCR with primers RClo8-5' (bases 716–742) and Rclo8-3' (bases 1178–1205). A rat Multiple Northern Blot (Clontech, Inc.) is also probed with a 427 bp fragment, i.e., RPLA$_2$-10 PCR probe, and amplified using primers Rclo10-5' (bases 226–253) and Rclo10-3' (bases 627–653). As seen in TABLE II, an RPLA$_2$-8 mRNA is detected in testis only and an RPLA$_2$-10 mRNA is detected in heart and perhaps lung only.

In order to determine the exon-intron junction sites and confirm the 121 bp direct repeat sequence in the genomic DNA, a 15 kb rat genomic DNA clone containing RPLA$_2$-8 coding exon II is analyzed by Southern blot, and partial sequencing. The 15 kb genomic DNA structure is shown in FIG. 4. It does not contain exon I and the 5' 121 bp repeat, but it does contain the 3' 121 bp repeat. To further investigate the 5' rat genomic DNA sequence, a cosmid genomic DNA library (Clontech, Inc.) is screened using a PCR-generated fragment containing RPLA2-8 exon I-intron I-exon II. Twelve positive clones are indentified. Restriction mapping indicates that all clones (about 40 kb each) are identical. Unfortunately, the cosmid clones could not contain the 5' 121 bp repeat because their 5' ends are located in intron I. Thus, RT-PCR is used to confirm the presence of the 5' 121 bp direct repeat sequence. Pla8-7, a 22 bp 5' primer starting at base 73, which lies within the 121 bp repeat sequence and pla8-8, a 22 bp 3' primer ending at base 212, see FIG. 3, are generated to conduct RT-PCR of rat brain total RNA. The resulting RT-PCR fragment is purified from the agrose gel and cloned into m13mp18, and the sequence is confirmed to be as predicted by the cDNA.

To test whether this PLA$_2$-8, gene encodes an active, secreted PLA$_2$, an Epstein Barr virus-based expression vector (pCEP) is used to express the RPLA$_2$-8 cDNA in human 293s cells. pCEP contains two regions of the EBV genome required for episomal maintenance (EBNA-1 and OriP), a drug resistance gene for selection in human cells (hyg), bacterial sequences for maintenance in E. coli, a drug resistance gene for selection in E. coli (amp), and an expression cassette for the production of high levels of mRNA from an introduced sequence by using an Rous/Sarcoma virus long terminal repeat (RSV LTR) promoter and an Simian virus 40 (SV40) polyadenylation signal. pR8-3', a chimeric construct, is constructed as follows. RASF-5', a 5' primer beginning with a 10 nucleotide NheI linker followed by 22 nucleotides starting at base 130, and Ju9, a 22 nucleotide 3' primer complementary to base 177 and 198, see Seilhamer, J. et al.: *J. Biol. Chem.*, 264:5335–5338 (1989), are used to PCR amplify plasmid pRASF from bases 130 to 198. pRASF contains the entire known $PLA_2$ Type II cDNA. See Seilhamer, J. et al.: *J. Biol. Chem.*, 264:5335–5338 (1989). The PCR product is purified and is digested with NheI plus NcoI. JuR8-11, a 5' primer with a total length of 31 nucleotides, beginning with GCCATGGGA followed by base 806 to 827 of $RPLA_2$-8 sequence, see FIG. 3, and R8-3', a 3' primer starting with a 10 nucleotide NheI linker at its 5' end, followed by 22 nucleotides complementary to $RPLA_2$-8 base 1178 to 1200, see FIG. 3, are used to PCR amplify plasmid $RPLA_2$-8. The PCR product is purified and digested with XhoI plus NcoI. Both digested PCR products are then ligated together into XhoI-NheI digested pCEP. Sequencing is carried out to confirm the nucleotide sequence of pR8-3'. CpR8-3' is a single clone of cells chosen to represent the typical pH optimum and $Ca^{++}$ dependence of CpR8 transfected 293s cells. The effects of pH and calcium concentration on enzyme activity are illustrated in FIGS. 23 and 24, respectively, for the $RPLA_2$-8 enzyme (Type III) and are similar, but different to the pH and calcium profiles for the $HPLA_2$-10 enzyme (Type IV) encoded for by the $HPLA_2$-10 cDNA cloned into plasmid cPH10, as shown in FIGS. 25 and 26, respectively. In other words, $RPLA_2$-8 also appears to be a pH and calcium-dependent $PLA_2$ enzyme having activity starting at about pH 5.5 and having significant activity at between about pH 7 and about pH 9 and having activity starting at about 0.1 mM $Ca^{2+}$ and having significant activity at between about 0.3 mM and about. 2 mM $Ca^{2+}$, respectively. The activity of $RPLA_2$-8, however, apparently progressively declines at a pH of greater than about 9 and at a calcium concentration of greater than about 2 mM. Nonetheless, FIGS. 23–26 illustrate phsopholipase activity for the Type III and Type IV phospholipase enzymes of the present invention. Moreover, FIGS. 23–26 show that the pH and calcium profiles for the Type III and Type IV phospholipase enzymes of the present invention are different from the pH and calcium profiles for phospholipases known heretofore.

It should be appreciated by those skilled in the art that the novel $PLA_2$ Type III and Type IV enzymes described in the instant application may have many different potential uses.

Although both "Type II" soluble $PLA_2$ and intracellular membrane-associated $PLA_2$ have been shown to mediate many aspects of the inflammatory cascade, it may well be that the new $PLA_2$ enzymes may also play a role, either by directly functioning to liberate arachidonic acid and 2-lysophospholipid, or by replacing the functions of the former in tissues and/or individuals in which the enzymes may be otherwise missing. As such, inhibition of these new enzymes by standard strategies known in the art (e.g., crystallography-based rational drug design; antisense; triple helix; monoclonal antibodies) could be valuable in anti-inflammatory therapy.

Phospholipases $A_2$ are involved in other processes vital to sustaining life in humans, including but not limited to pulmonary surfactant turnover, biomembrane maintenance and metabolism, various lipid catabolic pathways, platelet activation factor metabolism, and sperm-mediated egg activation. First, it is possible that certain diseases present today involve alterations in these functions, and could be treated therapeutically with exogenously added recombinant $PLA_2$ or anti-$PLA_2$. Second, as new $PLA_2$-inhibiting anti-inflammatory therapeutics are developed, many may exhibit cross-inhibition with these other new enzymes, thereby causing undesired side-effects. Both knowledge of the sequence/structure of these new enzymes, and the ability to restore their function through addition of the appropriate recombinant enzyme could be of value in reducing such side-effects.

Although these enzymes have been characterized as $PLA_2$ enzymes, they may well have other vital enzymatic activities. For example, LCAT (lecithin-cholesterol acyl transferase) also exhibits $PLA_2$ activity. Alternatively, these enzymes may function as phospholipases A1, phospholipases B, phospholipases C, lysophopholipases, acyl hydrolases, ribonucleases, lipases, or phosphodiesterases, all of which are esterases which resemble phospholipase $A_2$ in chemical activity. If this is the case, these new enzymes could be used to treat defects in a variety of metabolic pathways.

$PLA_2$ is also useful in the food processing industry. See Dutilh et al.: *J. Sci. Food Agricul.*, 32:451–458 (1981), and in the preservation of fish, see Mazeaud et al.: *J. Fish Res. Board Cun.*, 33:1297–1303 (1976). Recombinant forms of the instant new $PLA_2$s may be useful to replace natural sources of these enzymes.

$RPLA_2$-8, by virtue of its specific synthesis in rat testis, may play a key role in activation during fertilization by sperm. Therefore, antagonism of its function may prove useful as a specific anti-fertility reagent in pests such as rodents.

$HPLA_2$10 and $RPLA_2$-10, by virtue of their specific synthesis in cardiac tissue, may play a key role in cardiac lipid metabolism specific to cardiac tissue, and may indicate a specialized new function for this enzyme. A major component of heart tissue is cardiolipin, and Type IV phospholipase may mediate metabolism of this related diphospholipid in this organ. Therefore, recombinant forms of the new $PLA_2$s could prove useful in the treatment of disorders involving cardiac phospholipid metabolism.

In addition, the new $PLA_2$s have been mapped into a genetic locus known to be associated with Batten's disease (or Neuronal Ceroid Lipfuscinosis; NCL). Since the latter disorder has been shown to involve alterations in activity of certain phospholipases, see Dawson et al.: *Advances in Experimental Medicine & Biology*, 266:259–270 (1989), these new enzymes may be useful as a therapeutic to treat the former, and as a diagnostic to detect the presence of these genetic abnormalities so that proper counseling and early treatment of the disease would be possible.

Examples of various embodiments of the present invention will now be further illustrated with reference to the following Examples.

EXAMPLE I

CpCH10-1D Cell Line Transfected with pCH10 which Expresses $HPLA_2$-10

Total RNA is prepared according to the method of Chomcyzmski and Sacchi: *Analytical Biochemistry*, 162:156–159 (1987). 5' and 3' RACE-RT PCR techniques are used to generate the full length cDNA from total human brain RNA as described by Ishisaki: *Biochem. Biophysic. res. Comm.,* 162:1030–1036 (1989), and outlined in FIG. 10. PCR amplifications are done using 30 cycles at 95° C. for 20 seconds, 60° C. for 20 seconds and 72° C. for 75 seconds in 100 μl of buffer containing a final concentration of 1.5 mM $MgCl_2$, 200 μM dNTP, 100 mM Tris-HCl, pH 8.3, and 3 units Taq polymerase. Anchor (300 ng) and adaptor (50 ng) primers are used in both 5' and 3' RACE-RT PCR. Primers H10-C (300 μg) and H10-1a (300 μg) are used for 5' RACE-RT PCR. Primers H10-A (300 μg) and H10-1 (300 μg), see FIG. 10, are used for 3' RACE-RT PCR. Primer sequences are listed in TABLE IV.

TABLE IV

| Primers | Sequences |
|---|---|
| H10-A | CTGGCTTGGTTCCTGGCTTGTA |
| H10-1 | GCAAGGAGGCTTGCTGGACCTA |
| H10-1a | ATCGGTGCCATCCTTGGGGGTT |
| H10-C | GCAGAGGATGTTGGGAAAGTAT |
| H10-5' | GAATTCGCTAGCCAGAGATGAAAGGCCTCCTCCCACTGGCTTGG |
| H10-3' | CTCGCTCTCGAGGCCCTAGGAGCAGAGGATGTTGGGAAA |
| Anchor | GGCCACGCGTCGACTAGTAC(T)17 |
| Adaptor | GGCCACGCGTCGACTAGTAC |

$6 \times 10^5$ clones from a human stomach cDNA phage library (Clontech, Inc.) and $5 \times 10^5$ clones from a rat genomic DNA cosmid library (Clontech, Inc.) are screened according to the procedures provided by Clontech Inc.

A Human Multiple Northern Blot (Clontech, Inc.) is hybridized according to the manufacturer's directions.

293s cells (ATCC CRL 1573) are grown in Dulbecco's modified Eagle's medium (DMEM) supplemented with 10% fetal bovine serum. Approximately $7.5 \times 10^5$ cells are transfected with 10 μg of purified supercoiled plasmid DNA from either pCH10 or pRASF to create cell lines of the type CpCH10-1D and CpRASF-2B, respectively, according to the methods of Kingston, R. E.: *Calcium Phosphate Transfection* in Current Protocols in Molecular Biology. ed. Frederick M. Ausubel et al., pp. 9.1.1–9.1.3 (1989). Twenty-four hours after transfection, 200 units per ml of hygromycin is added to the medium. Stably-transfected, hygromycin-resistant colonies are selected ten days after transfection and are maintained in DMEM containing 200 units per ml of hygromycin. To test for $PLA_2$ activity, $2.0 \times 10^6$ cells are plated in a 25 cm² flask and medium is collected 24, 48 and 72 hours after plating.

Autoclaved [$1-^{14}C$] oleic acid-labeled *Escherichia coli* (*E. coli*) JM109 is prepared according to the methods described by Elsbach, P. et al.: *Methods in Enzymology,* 97:24–31 (1991) for use as a $PLA_2$ substrate. Briefly, 20 μl medium is incubated for 15 minutes at 37° C. with *E. coli* substrate (a mix of $2.5 \times 10^8$ labeled and unlabeled bacteria to provide 10,000 cpm) in a total volume of 250 μl (40 MM Tris/HCl, pH 7.8, 150 mM NaCl, 10 mM $Ca^{2+}$). The reaction is stopped by the addition of 250 μl ice cold 0.5% (W/V) fatty acid-poor BSA (USB). After incubation on ice for 5 minutes, the samples are centrifuged at 10,000×g for 3 minutes and 250 μl of the supernatant containing released ($1-^{14}C$)oleic acid is counted in a scintillation counter.

The pH optimum for human Type IV $PLA_2$ enzyme activity is determined using 20 μl of medium diluted to produce approximately 10% substrate hydrolysis. Sodium acetate buffer (final concentration 25 mM) is used for the pH range 4–6.5 and Tris/HCl buffer (final concentration 25 mM) for the pH range 7–9. See FIG. 25.

The calcium dependence of the human Type IV enzyme activity is examined in the calcium concentration range 0–400 mM. The buffer solution (Tris/HCl, pH 7.5, final concentration 25 mM) is prepared with doubly distilled, deionized water which contained a minimal amount of metal ions. EDTA (300 mcM) is added to the assay mixture in order to chelate the residual calcium. 20 μl of medium is diluted to produce 10% substrate hydrolysis. See FIG. 26.

EXAMPLE II

CpR8-3' Cell Line Transfected With pCR8 Which Epxresses $RPLA_2$-8

293s cells (ATCC CRL 1573) are grown in Dulbecco's modified Eagle's medium (DMEM) supplemented with 10% fetal bovine serum. Approximately $7.5 \times 10^5$ cells are transfected with 10 μg of purified supercoiled plasmid DNA from pR8-3' to create a cell line of the type CpR8-3' according to the methods of Kingston, R. E.: *Calcium Phosphate Transfection* in Current Protocols in Molecular Biology. ed. Frederick M. Ausubel et al., pp. 9.1.1–9.1.3 (1989). Twenty-four hours after transfection, 200 units per ml of hygromycin is added to the medium. Stably-transfected, hygromycin-resistant colonies are selected ten days after transfection and are maintained in DMEM containing 200 units per ml of hygromycin. To test for $PLA_2$ activity, $2.0 \times 10^6$ cells are plated in a 25 cm² flask and medium is collected 24, 48 and 72 hours after plating.

Autoclaved [$1-^{14}C$] oleic acid-labeled *Escherichia coli* (*E. coli*) JM109 is prepared according to the methods described by Elsbach, P. et al.: *Methods in Enzymology,* 97:24–31 (1991) for use as a $PLA_2$ substrate. Briefly, 20 μl medium is incubated for 15 minutes at 37° C. with *E. coli* substrate (a mix of $2.5 \times 10^8$ labeled and unlabeled bacteria to provide 10,000 cpm) in a total volume of 250 μl (40 mM Tris/HCl, pH 7.8, 150 mM NaCl, 10 mM $Ca^{2+}$). The reaction is stopped by the addition of 250 μl ice cold 0.5% (W/V) fatty acid-poor BSA (USB). After incubation on ice for 5 minutes, the samples are centrifuged at 10,000×g for 3 minutes and 250 μl of the supernatant containing released ($1-^{14}C$)oleic acid is counted in a scintillation counter.

The pH optimum for human Type III $PLA_2$ enzyme activity is determined using 20 μl of medium diluted to produce approximately 10% substrate hydrolysis. Sodium acetate buffer (final concentration 25 mM) is used for the pH range 4–6.5 and Tris/HCl buffer (final concentration 25 mM) for the pH range 7–9. See FIG. 23.

The calcium dependence of the human Type III enzyme activity is examined in the calcium concentration range 0–400 mM. The buffer solution (Tris/HCl, pH 7.5, final concentration 25 mM) is prepared with doubly distilled, deionized water which contained a minimal amount of metal ions. EDTA (300 mcM) is added to the assay mixture in order to chelate the residual calcium. 20 μl of medium is diluted to produce 10% substrate hydrolysis. See FIG. 24.

EXAMPLE III $PLA_2$ Activity $7.5 \times 10^5$ 293s cells are transfected with 10 ug of supercoiled plasmid DNA according to the method of Kingston, R. E.: Calcium Phosphate Transfection in Current Protocols in Molecular Biology. ed. Frederick M. Ausubel et al., pp. 9.1.1–9.1.3 (1989). Hygromycin-resistant colonies are selected 10 days after transfection and are maintained in DMEM containing 200 units of hygromycin. CpCH10-1B, CpCH10-1C, CpCH10-1D and CpCH10-2G are independent, hygromycin-resistant cell lines transfected with pCH10, a plasmid containing the human Type IV PLA$_2$ cDNA; CpRASF-2B is a hygromycin-resistant cell line transfected with pMCH6, a plasmid containing the known Type II PLA$_2$ gene. CpR8-3' is a hygromycin-resistant cell line transfected with pR8-3', a plasmid containing the rat Type III PLA$_2$ cDNA. These cell lines are tested two months after their stable transfection. Each has been maintained and subcloned in hygromycin-containing medium. For this experiment, exponentially growing cells are plated at 4×10$^5$ cells per ml. Medium samples are taken 24, 48 and 72 hours after plating. 20 μl of each medium sample is assayed under standard conditions, see Elsbach, P. et al.: *Methods in Enzymology*, 197:24–31 (1991) for PLA$_2$ activity. Activity is expressed as a fraction of autoclaved [1-$^{14}$C]oleic acid labeled *E. coli* Y1090 incubated alone. See FIG. 21.

EXAMPLE IV

Searching for Human cDNA and Genomic DNA Sequences Homologous to RPLA$_2$-8

Two primers, clo8-4 and clo8-5, synthesized according the published human h8 presumptive exon II sequence, Seilhamer, J. J.: *J. of Cellular Biochemistry*, 39:327–329 (1989), are used in a PCR amplification screen of human child brain, adult brain, liver, heart, and various white cell cDNA libraries. No PCR amplification is obtained from any of them. Two overlapping human genomic DNA clones, clone 8 and walk 9, containing 10 kb of DNA 5' of h8 exon II and 16 kb of DNA 3' of h8 exon II, respectively, are then analyzed. Southern blot analysis using the PCR fragment containing the RPLA2-8 open reading frame DNA sequence as a probe identified two EcoRI fragments, one in clone 8 and one in walk 9. These two fragments are subcloned into pUC19 and sequenced. DNA sequence homology between these sequences and the RPLA2-8 cDNA indicated that one fragment contains a region homologous to RPLA2-8 exons I and II, and that the other fragment contains a region homologous to RPLA2-8 exon IV. See FIG. 16. In order to search for exon III of a human RPLA2-8 homologue, the entire region between exon II and exon IV is sequenced. No region homologous to RPLA2-8 coding exon III is found by computer analysis of this sequence. To determine if the HPLA2-8 sequence is transcribed, two primers, one in coding exon II and one in exon IV, are used to do RT-PCR of human brain and lymphoblast total RNA. No PCR amplification signal is obtained.

EXAMPLE V

Phospholipase A$_2$ Assay Using Autoclaved Labeled Bacterium as a Substrate

Autoclaved [1-$^{14}$C]oleic acid-labeled *E.coli* 1-$^{14}$C 109 is prepared according to the methods described by Elsbach: P. et al.: *Methods in Enzymology*, 197:24–31 (1991) for use as the PLA$_2$ substrate. Commercial porcine pancreatic PLA$_2$ (Sigma) is used for the standard assay. Simply, the serialy diluted PLA$_2$ solutions are incubated for 15 minutes at 37° C. with *E.coli* substrate (a mix of 2.5×10$^8$ labeled and unlabled bacteria to provide 10,000 cpm) in a total volume of 250 ul (40 mM Tris/HCl, pH 7.8, 10 mM Ca$^{+2}$). The reaction is stopped by the addition of 250 ul ice cold 0.5% (W/V) fatty acid-poor BSA (USB). After incubatation on ice for 5 minutes, the samples are centrifuged at 10,000×g for 2 minutes, and 250 ul of the supernatant containing released [1-$^{14}$C]oleic acid is counted in a scintillation counter.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

Having described our inventions, we claim:

1. An isolated and purified DNA, said DNA comprising a sequence selected from the group consisting of:

SEQ. ID. NO. 21 (RPLA2-8);
SEQ. ID. NO. 29 (RLPA2-10);
SEQ. ID. NO. 31 (HPLA2-10);
SEQ. ID. NO. 33 (HPLA2-8);
a sequence encoding SEQ. ID. NO. 22 (aa RPLA2-8);
a sequence encoding SEQ. ID. NO. 30 (aa RPLA2-10);
a sequence encoding SEQ. ID. NO. 32 (aa HPLA2-10);
a sequence encoding SEQ. ID. NO. 40 (aa human Type IV PLA$_2$);
a sequence encoding SEQ. ID. NO. 44 (aa rat Type IV PLA$_2$);
nucleotides 149 to 548 of SEQ. ID. NO. 31 (HPLA2-10);
nucleotides 131 to 544 of SEQ. ID. NO. 31 (HPLA2-10); and
nucleotides 191 to 541 of SEQ. ID. NO. 31 (HPLA2-10).

2. The DNA of claim 1, wherein the sequence comprises SEQ. ID. NO. 31 (HPLA2-10).

3. An isolated and purified DNA comprising the sequence at SEQ. ID. NO. 21 (RPLA2-8).

4. An isolated and purified DNA comprising the sequence at SEQ. ID. NO. 29 (RPLA2-10).

5. An isolated and purified DNA comprising a sequence encoding SEQ. ID. NO. 22 (aa RPLA2-8).

6. An isolated and purified DNA comprising a sequence encoding SEQ. ID. NO. 30 (aa RPLA2-10).

7. An isolated and purified DNA comprising a sequence encoding SEQ. ID. NO. 32 (aa HPLA2-10).

8. An isolated and purified DNA comprising a sequence encoding SEQ. ID. NO. 40 (aa human Type IV PLA$_2$).

9. An isolated and purified DNA comprising a sequence encoding SEQ. ID. NO. 44 (aa rat Type IV PLA$_2$).

10. An isolated and purified DNA, said DNA consisting of a vector DNA coupled together with a sequence selected from the group consisting of:

SEQ. ID. NO. 23 (exon I HPLA2-8);
SEQ. ID. NO. 24 (exon I RPLA2-8);
SEQ. ID. NO. 25 (exon II HPLA2-8);
SEQ. ID. NO. 26 (exon II RPLA2-8);
SEQ. ID. NO. 27 (exon IV HPLA2-8); and
SEQ. ID. NO. 28 (exon IV RPLA2-8).

11. A recombinant DNA expression vector comprising:
a DNA selected from one of claims 1, 2 or 3 to 9, said DNA operably coupled with a promoter.

12. A host cell containing the vector of claim 11.

13. A method of producing a PLA$_2$ enzyme, said method comprising:
a) putting a recombinant expression vector into a host cell, said recombinant expression vector having a nucleotide sequence encoding the PLA$_2$ enzyme of claim 1;
b) cultivating said host cell; and
c) expressing the PLA$_2$ enzyme in said host cell.

14. A method of producing a PLA$_2$ enzyme, said method comprising:
a) putting a recombinant expression vector of claim 11 into a host cell;
b) cultivating said host cell; and
c) expressing the PLA$_2$ enzyme in said host cell.

* * * * *

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Met Lys Leu Leu Val Leu Ala Val Leu Leu Thr Val Ala Ala Ala
1            5                   10                15

(2) INFORMATION FOR SEQ ID NO:2:

(i) SEQUENCE CHARACTERISTICS:

(A) LENGTH: 7 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:2:

Asp Ser Gly Ile Ser Pro Arg
1               5

(2) INFORMATION FOR SEQ ID NO:3:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:3:

Ala Val Trp Gln Phe
1               5

(2) INFORMATION FOR SEQ ID NO:4:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:4:

Met Lys Thr Leu Leu Leu Ala Val Ile Met Ile Phe Gly Leu Leu Gln
1               5                   10                  15

Ala His Gly (2) INFORMATION FOR SEQ ID NO:5:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:5:

Asn Leu Val Asn Phe
1               5

(2) INFORMATION FOR SEQ ID NO:6:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:6:

Met Asp Leu Leu Val Ser Ser Gly Met Lys Gly Ile Ala Val Phe Leu
1               5                   10                  15

Val Phe Ile Phe Cys

20

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Trp Thr Thr Ser Thr Leu Ser
1               5

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Ser Phe Trp Gln Phe
1               5

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Met Lys Gly Leu Leu Pro Leu Ala Trp Phe Leu Ala Cys Ser Val Pro
1               5                   10                  15

Ala Val Gln Gly
            20

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Gly Leu Leu Asp Leu
1               5

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Lys Arg Leu Leu Thr Leu Ala Trp Phe Leu Ala Cys Ser Val Pro
1               5                   10                  15
Ala Val Pro Gly
            20

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Gly Leu Leu Glu Leu
1               5

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CTGGCTTGGT TCCTGGCTTG TA                                              22

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCAAGGAGGC TTGCTGGACC TA                                              22

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ATCGGTGCCA TCCTTGGGGG TT                                              22

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCAGAGGATG TTGGGAAAGT AT                                                    22

(2) INFORMATION FOR SEQ ID NO:17:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

GAATTCGCTA GCCAGAGATG AAAGGCCTCC TCCCACTGGC TTGG                             44

(2) INFORMATION FOR SEQ ID NO:18:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:18:

CTCGCTCTCG AGGCCCTAGG AGCAGAGGAT GTTGGGAAA                                   39

(2) INFORMATION FOR SEQ ID NO:19:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:19:

GGCCACGCGT CGACTAGTAC T                                                     21

(2) INFORMATION FOR SEQ ID NO:20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:20:

GGCCACGCGT CGACTAGTAC                                                       20

(2) INFORMATION FOR SEQ ID NO:21:

(i) SEQUENCE CHARACTERISTICS:
            (A) LENGTH: 4325 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS (B) LOCATION: 722..1195

(xi) SEQUENCE DESCRIPTION: SEQ ID NO:21:

```
GAATTCCGCC TCCACCTCTC AAATGCTGGG ATTGCAGGAT GTCCCCCCAC CCCTGCTCCC      60

TTGTGTCCTT GCTTCCTGCT GCCGGAATGT ATCACTTAAT TGCCAGGTAC CCATGGTCTG     120

ATTCCAGGAT AGAAGGGCGG GCGAGGGGGT TGGAGGAGAG GCCTCTATTA TTTCCGCGGT     180

CTGGCAGGCC TGGAAGCAAA GCTTCAAGTG CAGAAGGAGG AGTGTCGGGG AATGGCAGAA     240

AAGGCTGGAA CAGCAATGCA GACCTAGGTA AAGGGCACAG AGCTGAGGGA AGCTCCTGGG     300

AGGCTCCCTG CAGCTCCTGC CTCTGCACAT GACCCGGACT CCTTTTCTCT CTTTGGATCT     360

GCGTCCAGGG ACTGGCTTGT ACACACCCCT CCCAGGAGAC CCCTTGGCAG CTGCACACTC     420

AGGCTCCATC CAAGTTGGCT CTGCCCCTGG GGAAGGCTGC TCAAAAGGCC TGGCTCCCAG     480

TTTCTGGGGA CCCACAGAGA GCCTCTCACC TCGCAGCTCA GCTCCATCCG CCTCCTGTGC     540

CTGGCTGCGA CCAGCTGGGT CTAACTATAG ACAGTCAGCA ACTTCAGCCA CTTCACCGAG     600

TTTCCCAACA GCTTTGAGAT TTGGAAGCCG GAAGCCTGAT CGCCTTCTCA GAAGCTACGG     660

TCCACTACCT CAGCCATTCT GTTGGAGCTG AACTGGCAGA TGAAGGTGAG ACCCAGGCAC     720
```

```
C ATG GAC CTC CTG GTC TCC TCA GGA ATG AAG GGC ATC GCT GTC TTC         766
  Met Asp Leu Leu Val Ser Ser Gly Met Lys Gly Ile Ala Val Phe
   1               5                  10                  15

CTT GTC TTT ATC TTC TGC TGG ACA ACC TCC ACC CTC AGC AGC TTC TGG       814
Leu Val Phe Ile Phe Cys Trp Thr Thr Ser Thr Leu Ser Ser Phe Trp
                 20                  25                  30

CAG TTC CAG AGG ATG GTC AAA CAC ATC ACG GGG CGC AGC GCC TTC TTC       862
Gln Phe Gln Arg Met Val Lys His Ile Thr Gly Arg Ser Ala Phe Phe
             35                  40                  45

TCC TAT TAC GGA TAT GGC TGC TAC TGT GGG CTT GGG GGC CGA GGG ATC       910
Ser Tyr Tyr Gly Tyr Gly Cys Tyr Cys Gly Leu Gly Gly Arg Gly Ile
         50                  55                  60

CCT GTG GAC GCC ACA GAC AGG TGC TGC TGG GCT CAT GAC TGT TGC TAC       958
Pro Val Asp Ala Thr Asp Arg Cys Cys Trp Ala His Asp Cys Cys Tyr
     65                  70                  75

CAC AAG CTT AAG GAA TAT GGC TGC CAG CCC ATC TTG AAT GCC TAT CAG      1006
His Lys Leu Lys Glu Tyr Gly Cys Gln Pro Ile Leu Asn Ala Tyr Gln
 80                  85                  90                  95

TTT GCC ATT GTC AAC GGG ACC GTG ACC TGT GGA TGC ACC ATG GGT GGC      1054
Phe Ala Ile Val Asn Gly Thr Val Thr Cys Gly Cys Thr Met Gly Gly
                100                 105                 110

GGC TGC TTG TGC GGG CAG AAA GCC TGT GAG TGT GAC AAA CTG TCT GTG      1102
Gly Cys Leu Cys Gly Gln Lys Ala Cys Glu Cys Asp Lys Leu Ser Val
            115                 120                 125

TAC TGC TTC AAG GAG AAC CTG GCC ACC TAC GAG AAA ACT TTC AAG CAG      1150
Tyr Cys Phe Lys Glu Asn Leu Ala Thr Tyr Glu Lys Thr Phe Lys Gln
        130                 135                 140

CTC TTC CCC ACC AGG CCC CAG TGT GGC AGG GAC AAA CTC CAT TGC          1195
Leu Phe Pro Thr Arg Pro Gln Cys Gly Arg Asp Lys Leu His Cys
    145                 150                 155
```

```
TAGGCCTTCC CCTCCAAGAG TCCCCAGGCT CCTGCAGCTC AGCCTTGCTG TCTAGGGAGT    1255

GTCTTCTCAG GCATTAGGGG ACCGGAGGTG GAGAATTCCT GCCCTGGAAT CAGACCATGG    1315

GTACCTGGCA ATTAAGTGAT ACATTCCGGC AGCAGGAAGC AAGGACACAA GGGAGCAGGG    1375

GTGGGGGGAC ATCCTGCAAT CCCAGCATTT GAGAGGTGGA GGCAAGAGGT GGGGGGTAGC    1435

CTCCACTATA CGGTAAGTTC AAGGCTAACC TGAGCTACCT GAGACCTTGC CTTGAAAAAA    1495

CTTTTTTAAA AAACGTTTAA AGGAAAAGAA AACAGAAAGA CACGGGGACT GGGCTGAAAG    1555
```

```
GTACTCTCAA ACCGATTTCC CAGGAAGAGC GGAGAGCCCC AGGTTCAGCT CCAGCCTGAA    1615

CTCCCCCATA CCCTCAGTCC TGGTCAGGAT GTGTGTCTGA CTGGGAACC AAGTCCTCCA    1675

CCCGGGTGGA GCTTAGCTGG GAACTACGCA GGTGTCCTAG AAAATACAGT CCTAAGAGCC   1735

TCACCCGGAG TCTCATCCCC ATTTGCTCCA GGACTGACCT CTGTAAATCT TCCAGCAGGA   1795

AGCAGGCTGT ACCCATCTCA GGAGGTGGGG TGCTGTTAGA CAATGGTGT GCACCAGTGA   1855

CACAAAGATG TCATGGTTAA GATGGCATCA AGAAGTGGAA AGGACATTCG GAACAGTGGG   1915

TCCAAGGCAC CCAAAGTCCT CACCCCAATT TAGAAGCCGT TGGTCCTGTA AGACTTAAAT   1975

CTACTAAACA AGGAAGGTCT AACTGGGCTG GAATCTGAAG TTCATGGTGC CAGGCTGGGG   2035

CGGTGGGTGG GGACGTGGCC GTGGCCATGA CCATGATTGC CTCTCTGCAT GGTGACACTT   2095

GCCTTTTGCA CCCTAGCTCT CAGCACATCT GAAAAGGACA GACTCTCCTG TTCATTCCTT   2155

GAATCTGAGA CTCTCCTCAC TAATGTAGCA AAAATGGAGG TCTAAAGTGC AGGCTTCAGC   2215

CTCTGAGGTC CAGGGCAGGA GGAAGCTGGG GCTCAGCCTC CTGGAGGATG AGAGCTTGCC   2275

GGGTGAGCAT CAGCGACAGC AGACCCTTGG GCTCAGAGAG TCCGCAAGCC TGGGAGAGCC   2335

TGGCCGAGCC CTGACTGCAG CACACAGAGC CGTGAGCCTC ATACAAGAAG CCACATTTTG   2395

GGGAAGCTTC AGGGTGGCTG ATTCCACAGC TGTTGGGTTC AGAACGGAAG CCGGGAGCAC   2455

TCACTTCAGA TATGGAAGCT TTGTTTTACG AGCGCTTAGC ACCAGTTCAG GATCTGAACT   2515

TCGTCCTGAC CGGAGAGTCC GTACCACATT TTTATAGGAT GGGAACACAG AGCGAGGGGC   2575

GTGGAGTAAG CTGTTGAACG ACCGATCATA TTTTGACCTA AGAGGTTAAG TAAGGACGTT   2635

AACATGGGTG ACTGGGCATT AGTCAGGTCA CCTGGTTTTG GGGTCTTTGA ATCAGCTTTC   2695

GTGGCCAGGT CCCTTCCTGG ACTTTGGCTC GGAATTTAGA ACGATAAGGG AACGAAGAGG   2755

TGGGCAAGCT TCGGGCAGTC AGTAAGAGGC AGCACATTCA TGACCTGTGT GCCTTGTTTA   2815

GATAATGGGA TAAGAGTATC TCCTCTCTTA CACCCCTTAC TGGTTAACAG ACAAACACGA   2875

GACATCTGAA GAAGCAGGAC AGGAGTTAGG TTCTGGGGCA CAGGAACATG AACTCGGTTT   2935

TGATCCTGCC GGCAAGGTGG ATCTTGTTCC TGAGAAGGCT GGACTCAGGA AACTTCCTCT   2995

TAACAAGTTA GTTGATGGCG CTGGTCCTTA GTCACCGATA CTGTCAGGCT CTCAGCTCTT   3055

GGGCCAGACT TGGCGGCCAT GGGAGTGTGG TCACTTGCCC CGTCCCCTTC TTCCAGGAGG   3115

TACTGGGGAA AATGGTTGGA TTTGTGGAGT TGTAGGGAAC ACTCATGGCT CCCTTCACTT   3175

AGTAGGTCAG CTAACATATG TGTATCGAGC CCATACCGTG TGCCATGTGC AGTGCTGAGC   3235

AGCAGGGAGT CAGAGATTTA AAGACACACA CACAGACTTC AAGTCTGAGA ATTTTGAATC   3295

CCAGGGAGAA CCGCTGAGAG CCATGGCGCT TCTACCAATG CCAGAGGCTA ACACCCGGAC   3355

TGAGAAAACT AAGCACGAGG AGACAGCAGG GTCAGCAGAG GGCCTGGGAG CTAGGGCCCT   3415

GAGCAGTACC TAGTTCAAAT CACAGAGTCG TCTTTCTTCC TCCACCCTAC CCAGGTACAG   3475

CAAGTAGACA CGGGTGGGGG CAGGGCAGGG ATGCAGGAAC ATTAGGGCAC ACCGATGTGG   3535

CTAGGCTAAG CTAGAGCATG TTACCTTCTC AGGGGTCCTG TCATGTCAGA GACTGGTTCC   3595

AACCTGGAAA GATGTCTGAG TGACAGCTGT GGTAGAAGAA GAGAGGCCAG GGTGATATCA   3655

GCATGAAGGG CTGGATTGCT ATGTGAGATC CAGATCTCTT CTGCCACTGG GGTCAGCTTC   3715

TACACTGGAA ATAGATGGGC TGCGTTATGG AGGGTGGTGT GAGTCCCTGT CTGCGTTGTG   3775

CCGGGAATCA GAGCAGAGTG TTAGCGCTGT AAAAGGACAT GCTGGTGTTT GCAGGAAATC   3835

ATCGATTTCT TGGAAGGGCA GCCATTCATC TACACCAGGG ATTGACTTTA TGCCAGGCTT   3895
```

```
GTGATGAGGG TAGAAAAGTA GAAATTCTGT CCGCTGCAAG GAGCAGTCAG AGGACACAAG      3955

GACCAAATAG CTTGGGAGTT GCGGAAGTAG GTGTCTGCTG AGGGAGCAGT GACCACTGGG      4015

GGAAAGGCTC CTTCAAGGAA TTCAGGGACA GGGGTGAGGG CTGACATCTT GCCTGAGACC      4075

CTAAAGAAGA GAAGGAGTTG AGAGGGCTGA GTATGCTGTG TGGAGCCCCA CCCCCACCCC      4135

CACCCCCACC CCCACCCCAG GTATATGGAT GGAGGATAAT GCGGGGTCG GGTTCCTCTC       4195

AAATCCATCA TCCCACCTTC GAGCTGCTGG CACGGCCTTG CCAGCACAGC CCGATTCTGT      4255

GTTGACAAAA TACTCGAACG AAATGATTAC ATGCAAATAA AATGCAAGAG GAAAAATCTA      4315

AACGGAATTC                                                            4325
```

(2) INFORMATION FOR SEQ ID NO:22:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:22:

```
Met Asp Leu Leu Val Ser Ser Gly Met Lys Gly Ile Ala Val Phe Leu
 1               5                  10                  15

Val Phe Ile Phe Cys Trp Thr Thr Ser Thr Leu Ser Ser Phe Trp Gln
             20                  25                  30

Phe Gln Arg Met Val Lys His Ile Thr Gly Arg Ser Ala Phe Phe Ser
         35                  40                  45

Tyr Tyr Gly Tyr Gly Cys Tyr Cys Gly Leu Gly Arg Gly Ile Pro
     50                  55                  60

Val Asp Ala Thr Asp Arg Cys Cys Trp Ala His Asp Cys Cys Tyr His
65                  70                  75                  80

Lys Leu Lys Glu Tyr Gly Cys Gln Pro Ile Leu Asn Ala Tyr Gln Phe
                 85                  90                  95

Ala Ile Val Asn Gly Thr Val Thr Cys Gly Cys Thr Met Gly Gly Gly
            100                 105                 110

Cys Leu Cys Gly Gln Lys Ala Cys Glu Cys Asp Lys Leu Ser Val Tyr
        115                 120                 125

Cys Phe Lys Glu Asn Leu Ala Thr Tyr Glu Lys Thr Phe Lys Gln Leu
    130                 135                 140

Phe Pro Thr Arg Pro Gln Cys Gly Arg Asp Lys Leu His Cys
145                 150                 155
```

(2) INFORMATION FOR SEQ ID NO:23:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
ACCTCAGACC CCCTGGTCTC CTCAGGAATG AAGGTCATTG CCATCCTCAC CCTCCTCCTC      60

TTCTGCT                                                               67
```

(2) INFORMATION FOR SEQ ID NO:24:

(i) SEQUENCE CHARACTERISTICS:

(A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

ACCATGGACC TCCTGGTCTC CTCAGGAATG AAGGGCATCG CTGTCTTCCT TGTCTTTATC      60

TTCTGCT                                                               67

(2) INFORMATION FOR SEQ ID NO:25:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

TGGTGGCAGC CCCCACCCAC AGCAGTTTCT GGCAGTTTCA GAGGAGGGTC AAACACATCA      60

CGGGGCGAAG TGCCTTCTTC TCATATTACG GATATGGCTG CTACTGTGGG CTTGGGGATA     120

AAGGGATCCC CGTGGATGAC ACTGACAGGT G                                    151

(2) INFORMATION FOR SEQ ID NO:26:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CAGGGACAAC CTCCACCCTC AGCAGCTTCT GGCAGTTCCA GAGGATGGTC AAACACATCA      60

CGGGGCGCAG CGCCTTCTTC TCCTATTACG GATATGGCTG CTACTGTGGG CTTGGGGGCC     120

GAGGGATCCC TGTGGACGCC ACAGACAGGT G                                    151

(2) INFORMATION FOR SEQ ID NO:27:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TAGGTGGATG CACCCTTGGT CCTGGTGCCA GCTGCCACTG CAGGCTGAAG GCCTGTGAGT      60

GTGACAAGCA ATCCGTGCAC TGCTTCAAAG AGAGCCTGCC CACCTATGAG AAAAACTTCA     120

AGCAGTTCTC CAGCCGGCCC AGGTGTGGCA GACATAAGCC CTGGTGCTAG                170

(2) INFORMATION FOR SEQ ID NO:28:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
CAGGTGGATG CACCATGGGT GGCGGCTGCT TGTGCGGGCA GAAAGCCTGT GAGTGTGACA      60

AACTGTCTGT GTACTGCTTC AAGGAGAACC TGGCCACCTA CGAGAAAACT TTCAAGCAGC     120

TCTTCCCCAC CAGGCCCCAG TGTGGCAGGG ACAAACTCCA TTGCTAG                  167
```

(2) INFORMATION FOR SEQ ID NO:29:

(i) SEQUENCE CHARACTERISTICS:
  (A) LENGTH: 1828 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 233..643

(xi) SEQUENCE DESCRIPTION: SEQ ID NO:29:

```
GAATTCCGGT GGATGGAGGG GGCTGAGCAG GATGTTGACT GGCTATCGTT CATTGAGCAC      60

TCTCACGATC AGCATCACGC ACGGAATCCA TCCTTCCTGT GTTGCAGCTT GTAGACCCTG     120

ATGCTTGGGC TGCCAGCATA ACGTGGGGA TCCAGACTCT GTCTACCGAG CTGCCCATA       180

GGGACAGGCC CTGGGAAGAG GAGCTGAGAC CAGGCTAAAA AGAACCCAAG AA ATG         235
                                                           Met
                                                            1

AAG CGC CTC CTC ACG CTG GCT TGG TTC CTG GCT TGC AGT GTG CCT GCA      283
Lys Arg Leu Leu Thr Leu Ala Trp Phe Leu Ala Cys Ser Val Pro Ala
            5                  10                  15

GTC CCA GGG GGC TTG CTA GAA CTG AAG TCC ATG ATT GAG AAG GTG ACT      331
Val Pro Gly Gly Leu Leu Glu Leu Lys Ser Met Ile Glu Lys Val Thr
         20                  25                  30

GGG AAG AAT GCC GTA AAG AAC TAT GGC TTC TAC GGC TGC TAC TGT GGC      379
Gly Lys Asn Ala Val Lys Asn Tyr Gly Phe Tyr Gly Cys Tyr Cys Gly
     35                  40                  45

TGG GGC GGC CAC GGG ACC CCT AAG GAT GGC ACT GAT TGG TGC TGT CGG      427
Trp Gly Gly His Gly Thr Pro Lys Asp Gly Thr Asp Trp Cys Cys Arg
 50                  55                  60                  65

ATG CAC GAC CGT TGT TAT GGG CTA CTG GAG GAG AAA CAC TGT GCC ATC      475
Met His Asp Arg Cys Tyr Gly Leu Leu Glu Glu Lys His Cys Ala Ile
                 70                  75                  80

CGG ACC CAG TCC TAT GAC TAC AGA TTC ACA CAG GAC TTA GTC ATC TGC      523
Arg Thr Gln Ser Tyr Asp Tyr Arg Phe Thr Gln Asp Leu Val Ile Cys
             85                  90                  95

GAA CAC GAC TCC TTC TGT CCA GTG AGG CTT TGT GCT TGT GAC CGG AAG      571
Glu His Asp Ser Phe Cys Pro Val Arg Leu Cys Ala Cys Asp Arg Lys
        100                 105                 110

CTG GTC TAC TGC CTG AGG AGA AAC CTC TGG AGT TAC AAC CGT CTT TAC      619
Leu Val Tyr Cys Leu Arg Arg Asn Leu Trp Ser Tyr Asn Arg Leu Tyr
    115                 120                 125

CAG TAT TAC CCC AAC TTC CTC TGC TAATGTCCTC TGTGGGCTCT CGCCGGGAGT     673
Gln Tyr Tyr Pro Asn Phe Leu Cys
130                 135

GCCTCCCACA GTGGCGGCCC CCCTCGGCTG TATTCCTGAT CCGTCCACCC AAGGTCTTGG    733

ATCTGCCTTC CTCTGTGTAC CACTGGGCTG ACAGAGCCC AGGGTTACAC CCTACCCTCC     793

AGAATCCTAG AGAGGGACTC TGATGTAGAG TCTGCGGACT CTGGATAGCT GAGCCTGCAC    853
```

```
TTGCAGAATT TGGCGCTGGG CCCCGGAGCT CCCTCAGCTC CAGGCCAGTG TCGTGTTGAC      913

TTTCCTTTCA ATTTCTGGAA CCCAACTGCC ATTACCACCC TCCAGAGACC TCTTACTAGA      973

GGAGAAGCCA AATTAACTCT ATAAATCTGC CATGTAGCTA TTAAATAAAA CCCATTCACG     1033

AGGCGAGAAG AACACCACCC CAGCACTCCC TCTGACAGGG CTGGGGTAGG AGTGCCAATG     1093

CTTCTCTAAC CCCTGAGGCA TCTGTGCACC CTCTAGGATG GAGGTCAGGA AACAGGTGGG     1153

GGCCTTACAT GCCTTTCATG GTTTGTCTTG AGTTTATTTT CTTAAACCTT AGGGTCTTTC     1213

AAGCCAGACC TGGAGCTCAA GATTCTTCTG GAGGAAGGTG AGACACAGCC CTATGCCACC     1273

TTGAGCTCCA GGCTAGAAAG GGACAGCCCC TAGCCCTGGC TTCTGCAACT GTGTGGTCTT     1333

GAACCTCCGT ATAGTCCGAA TCCCTCTGGC TCTCCTCAAA ATATAAAACA AGCCTCCTTC     1393

CAATAGCATA TTGGTGCACA CCCCTAATCC CATCACCTGG GAGGAGGAGG CGGCAGGAGC     1453

ATCAGGAGTT CAAGGCCAGC TCCTGCCCCC TAGCAGGGAT GGTAGGCTGC ATGAGAGTGT     1513

GTCTCAGAAA GAACCACCTG GTGCGGGTAC AGGGATGCTG GGATTCTGAG ATGTCACTCA     1573

GTGCGGGAAA AGATTCAAGG AGGGGAACAG ATCAATGGCA GAATGACTGT CTGTGCCGAG     1633

TTAAGGGCAC TGAAAATCTC AGCTCATCTA TCGCTTTATA GAAGATAGAG CTTTGGGAGG     1693

AAGCAAGGCA CTCTACAGTA AAGGAGTGGC CTTTCCAAGG AAGGGTCTAG GCTCCTTCTT     1753

CTCCAGAACA TGCACAGGAC ATAGGAGATC CATTATTTAG AGACCTTTCG TGTTCGAACG     1813

TTTTCTCCGG AATTC                                                     1828

(2) INFORMATION FOR SEQ ID NO:30:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:30:

Met Lys Arg Leu Leu Thr Leu Ala Trp Phe Leu Ala Cys Ser Val Pro
  1               5                  10                  15

Ala Val Pro Gly Gly Leu Leu Glu Leu Lys Ser Met Ile Glu Lys Val
                 20                  25                  30

Thr Gly Lys Asn Ala Val Lys Asn Tyr Gly Phe Tyr Gly Cys Tyr Cys
             35                  40                  45

Gly Trp Gly Gly His Gly Thr Pro Lys Asp Gly Thr Asp Trp Cys Cys
         50                  55                  60

Arg Met His Asp Arg Cys Tyr Gly Leu Leu Glu Glu Lys His Cys Ala
 65                  70                  75                  80

Ile Arg Thr Gln Ser Tyr Asp Tyr Arg Phe Thr Gln Asp Leu Val Ile
                 85                  90                  95

Cys Glu His Asp Ser Phe Cys Pro Val Arg Leu Cys Ala Cys Asp Arg
            100                 105                 110

Lys Leu Val Tyr Cys Leu Arg Arg Asn Leu Trp Ser Tyr Asn Arg Leu
        115                 120                 125

Tyr Gln Tyr Tyr Pro Asn Phe Leu Cys
    130                 135

(2) INFORMATION FOR SEQ ID NO:31:

(i) SEQUENCE CHARACTERISTICS:
        (A) LENGTH: 1014 base pairs
        (B) TYPE: nucleic acid
```

```
            (C) STRANDEDNESS: single
            (D) TOPOLOGY: linear (ii) MOLECULE TYPE: cDNA (ix) FEATURE:
            (A) NAME/KEY: CDS
            (B) LOCATION: 131..544

(xi) SEQUENCE DESCRIPTION: SEQ ID NO:31:

GGATACCAAT GTTCCGACTG GAGACGGGGA GCCCGCGAGA CCCGGGTCTC CAGGGTCTGC         60

CCAAGGAAGT TGCTCATGGG AGCAGACCCC TAGAGCAGGA TTTGAGGCCA GGCCAAAGAG        120

AACCCCAGAG ATG AAA GGC CTC CTC CCA CTG GCT TGG TTC CTG GCT TGT          169
           Met Lys Gly Leu Leu Pro Leu Ala Trp Phe Leu Ala Cys
             1               5                  10

AGT GTG CCT GCT GTG CAA GGA GGC TTG CTG GAC CTA AAA TCA ATG ATC         217
Ser Val Pro Ala Val Gln Gly Gly Leu Leu Asp Leu Lys Ser Met Ile
     15                  20                  25

GAG AAG GTG ACA GGG AAG AAC GCC CTG ACA AAC TAC GGC TTC TAC GGC         265
Glu Lys Val Thr Gly Lys Asn Ala Leu Thr Asn Tyr Gly Phe Tyr Gly
 30                  35                  40                  45

TGT TAC TGC GGC TGG GGC GGC CGA GGA ACC CCC AAG GAT GGC ACC GAT         313
Cys Tyr Cys Gly Trp Gly Gly Arg Gly Thr Pro Lys Asp Gly Thr Asp
                 50                  55                  60

TGG TGC TGT TGG GCG CAT GAC CAC TGC TAT GGG CGG CTG GAG GAG AAG         361
Trp Cys Cys Trp Ala His Asp His Cys Tyr Gly Arg Leu Glu Glu Lys
             65                  70                  75

GGC TGC AAC ATT CGC ACA CAG TCC TAC AAA TAC AGA TTC GCG TGG GGC         409
Gly Cys Asn Ile Arg Thr Gln Ser Tyr Lys Tyr Arg Phe Ala Trp Gly
         80                  85                  90

GTG GTC ACC TGC GAG CCC GGG CCC TTC TGC CAT GTC AAC CTC TGT GCC         457
Val Val Thr Cys Glu Pro Gly Pro Phe Cys His Val Asn Leu Cys Ala
     95                 100                 105

TGT GAC CGG AAG CTC GTC TAC TGC CTC AAG AGA AAC CTA CGG AGC TAC         505
Cys Asp Arg Lys Leu Val Tyr Cys Leu Lys Arg Asn Leu Arg Ser Tyr
110                 115                 120                 125

AAC CCA CAG TAC CAA TAC TTT CCC AAC ATC CTC TGC TCC TAGGCCTCCC          554
Asn Pro Gln Tyr Gln Tyr Phe Pro Asn Ile Leu Cys Ser
                130                 135

CAGCGAGCTC CTCCCAGACC AAGACTTTTG TTCTGTTTTT CTACAACACA GAGTACTGAC        614

TCTGCCTGGT TCCTGAGAGA GGCTCCTAAG TCACAGACCT CAGTCTTTCT CGAAGCTTGG        674

CGGACCCCCA GGGCCACACT GTACCCTCCA GCGAGTCCCA GGGGAGTGAC TCTGGTCATA        734

GGACTTGGTA GGGTCCCAGG GTCCCTAGGC CTCCACTTCT GAGGGCAGCC CCTCTGGTGC        794

CAAGAGCTCT CCTCCAACTC AGGGTTGGCT GTGTCTCTTT TCTTCTCTGA AGACAGCGTC        854

CTGGCTCCAG TTGGAACACT TTCCTGAGAT GCACTTACTT CTCAGCTTCT GCGATCAGAT        914

TATCATCACC ACCACCCTCC AGAGAATTTT ACGCAAGAAG AGCCAAATTG ACTCTCTAAA        974

TCTGGTGTAT GGGTATTAAA TAAAATTCAT TCTCAAGGCT                            1014

(2) INFORMATION FOR SEQ ID NO:32:

(i) SEQUENCE CHARACTERISTICS:
            (A) LENGTH: 138 amino acids
            (B) TYPE: amino acid
            (D) TOPOLOGY: linear (ii) MOLECULE TYPE: protein (xi) SEQUENCE DESCRIPTION: SEQ ID NO:32:
```

```
Met Lys Gly Leu Leu Pro Leu Ala Trp Phe Leu Ala Cys Ser Val Pro
 1               5                  10                 15
Ala Val Gln Gly Gly Leu Leu Asp Leu Lys Ser Met Ile Glu Lys Val
             20                  25                  30
Thr Gly Lys Asn Ala Leu Thr Asn Tyr Gly Phe Tyr Gly Cys Tyr Cys
         35                  40                  45
Gly Trp Gly Gly Arg Gly Thr Pro Lys Asp Gly Thr Asp Trp Cys Cys
     50                  55                  60
Trp Ala His Asp His Cys Tyr Gly Arg Leu Glu Glu Lys Gly Cys Asn
 65                  70                  75                  80
Ile Arg Thr Gln Ser Tyr Lys Tyr Arg Phe Ala Trp Gly Val Val Thr
                 85                  90                  95
Cys Glu Pro Gly Pro Phe Cys His Val Asn Leu Cys Ala Cys Asp Arg
             100                 105                 110
Lys Leu Val Tyr Cys Leu Lys Arg Asn Leu Arg Ser Tyr Asn Pro Gln
             115                 120                 125
Tyr Gln Tyr Phe Pro Asn Ile Leu Cys Ser
130                 135
```

(2) INFORMATION FOR SEQ ID NO:33:

(i) SEQUENCE CHARACTERISTICS:
        (A) LENGTH: 15328 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

```
AAGCTTTGTG GGATTTCTAT TATGAACAAC ATAGGTGCCT TTCCAACTCG GAACAGAGG       60
AAATATGGAC TCCTCAAAAG AAAAAAAGAA GAGATGAAGG GATGATGTTG CCAAAGAAAG     120
AAATTTGGAA AAAAAAAAAC CAAACCAACA TTTGCACTTT CAAAACCATG GAACCCTTCT    180
TATTTTTATA TGTTCAGATC TAAATGCCAG AAAGGTTACC ACATTCAAAG GAATGAGAT     240
TTGAAAATGA TTTCTTTGAG TCCTCTGCTG AGGTCTTTCC AAGGCACTAC AATTAGGGCT    300
TTGCACCCAA ATACCCTTGC CTCATTTTGG TCATTTTTGT CCTGGAACAG AGGTTCAGCT    360
GGGAGACCCC TCACACACAG GTGAAGGCGT GGCTGTAGAA CCTCAGACCC CCTGGTCTCC    420
TCAGGAATGA AGGTCATTGC CATCCTCACC CTCCTCCTCT TCTGCTGTAA GTAGAGAGCG    480
TTGGTGGGTC AGCACCAAGC TTCTGTCTTC CTGTTTATGT CAGTGGGAGG GGGGACTCTC    540
CAGGTGGCAC CAGGTGAGGG AAGTCACAAG TCCCGCAGAA AAGAATCAGG AAAGGAACGG    600
GCTCCCACCA ACGTCCTCTT GCTTCTGTTT CTGCTATAAA ATGGGCTGAT CCCAGTGTTG    660
GGATCTTATA AAGTGTCTAG GAAATCGAG GTTGCCAACC ATTTGCTAGA AAGGGAGTTT     720
GAGTAGTATT TTACCCCCCC TCACCCTCAA GAGTCTTTTT ACTTTGGATG CTAGTAGCCT    780
TTTATTTAGG CATTGGATCA GAACAAAAAT GCAGGACATA TATCCAGCCT AATTTAACCA    840
ATGGATTAAA TGGCCTTATC AGGAAAAGAC CATTTTATGG TGACTTATGG GATAATTGGT    900
AGTTATAAGT CATTGCTGCC GGGAGATCCG ATTGCTTACC TCTGCAAAGT GAAGAAAGAC    960
CTACTGGGAA ACAGTTTGGG GTCTACTGGA GACTGATAGA CTCTTTTGCT GGATTCGTTG   1020
AGTGGAGGTT TCTCCAGATC CATTTTCCTG TCTCTTTCAA TTGAGTCACA ATAACTTTTG   1080
AGTCCCTAAG TCAAAGATGT CAAAAACAGA CTTCCTTTCC CCACAGTGAG TGGTGGAATT   1140
TACACTTTGC AAGGTGATAG TGCAGGAGGA TACCTGTACG CAGGGATGAC CGCCTCTGCA   1200
```

-continued

```
GCCCTCAGTG CGGCTCCAGG ACTGCTTGGG CACCAGTGAC CGCCCCATGG GTTTCTTCCG    1260

CCACACCCCC GTTTAGACTG AACACGATAG GTAGATCGAA GGCCACCTGA GAAAACTCCC    1320

CCAAAACTCT ATTTCTGTTT CTCTTCTTCA AAGTTCATGT CTTTGTTGTA TTTTTATTGC    1380

AAATTTACTA CATGCTTATA GTTAAAAAGT AAAATAAATG AGTATATAGC AACAAGGTAA    1440

AGCTCCTCCT CATCCTCCCC AGACCCCAGT TTTTTCCCTA CATCCAGATG TGACCACTCT    1500

TAAGAGTTTG ATATACATCC TCTATACAGC GTTTACCACA CACACATTCA AAACACCATA    1560

ATAGGAAGGG AACACATGCT GGGCCGGGCG CGGTTGTTCA TGACTATAAT CCCAGCACTT    1620

TGGGAGGCCG AGGCGGGCGG ATCACCTGAG GTCAGGAGTT CGAGACCAGC CTGGCCAGCT    1680

GGCAACATGG TGAAACCCGT CTCTATTAAA AATACAAAAA ATTAGTCAAG CATGGCAGTT    1740

GGGCACCTGT AATCCCAGCT ACTCAGGAGG CTGAGGCAGG AGAATTGCCT GAACCCGGGA    1800

GGCGGAGGTT GCAGTGAGCC GAGATCACAC CATTGCACTC CAGCCTGGGT AACAACAGCG    1860

AAACTCCGTC TCAAAAAAAA AAAAAAAGA AGGAAAGGGA CACACGCTTA TTATGAAAGA     1920

CATGAGACAG CGGAGACGTG TATAAATGAT GTTGCCTGTT TTCTTTCTCT CTCTTCATCC    1980

ATGCTAGAGA TAGTGCTATC AAATGTAGTT ATTTTTGAGA CACATATTTC GTATTATCCC    2040

TGTCGTGACA TGTGGGTGGT TTCCAATTTT TTGATATCAC AGATAATGCT TCAGGAAACC    2100

ATTTTGTGTA TCGATTTGTG CCCACTCTCA TAAGCATCTT GTAGAAGCAA AAACAGCTGA    2160

GTTCATGTGT ACTTGTCATT TAAAAAAATA ATAATTGAGG ATACCTTTCC TGCCTCTTAA    2220

GTATTTTGTT TCTCCTGTGA GATAGTAAAG GCCTGATGAC ATCTGGAGGG ACTGGCGTTT    2280

CTGGCTTTGA ACTTTTGCCA TTCATGTTGC ATCAGACCCG AGGGTGTTCT GCCTAGAACT    2340

GTGGTTTCTT GCTTTGAGGG GGAAGACTAT GGTTGATGGG AAAGCCTTGT TCTGAACCTC    2400

ATGGAAACTG GGTATTCATC TGGGTTAGCA AAAAACTAGC TGTGTTACAG GGCAAATCT     2460

GAACCTATTT TATTCCCCAG GAAAGAGGCT GGTGATTCCA GCCATGCCCC TTGCACTTCG    2520

CTTTGGGGAT CTGGTGATAT TTCGAATGCT CAGCACTCTA GTAAGGGGAG GGACATCAA     2580

GGCAGCATCA TGCTCATTGC AACTTCCTTC TTCCTTTTTT TCTCATCGGT GGTGGCAGCC    2640

CCCACCCACA GCAGTTTCTG GCAGTTTCAG AGGAGGGTCA AACACATCAC GGGGCGAAGT    2700

GCCTTCTTCT CATATTACGG ATATGGCTGC TACTGTGGGC TTGGGGATAA AGGGATCCCC    2760

GTGGATGACA CTGACAGGTG GGTGCAGAGG CTCTAAGGCC ACTTATCATT TGTTTTGCAT    2820

TAAAGTTCAT GCTCAAAGCC AGAGAGAGGG TCTTAGGATT CTTGCCTGGC AAATAACAGA    2880

AAACAACTCA GGCTAATGGA AGGAAGAACT GAACGGGATT TGGAGGATGG GTCTTGAGAA    2940

ACCCAGGGTC GGGGCCAGCT TCTTGAGTGT GTGACCTGTG AAGTTTCACA GGCCCAACA     3000

CTCATAAGGG TCAGGGCCAG CTTCTTGAGC GTGTGATCTG TAAAGTTTCA CAGGGCCTGG    3060

CACTCATAAC CCCCTAAACA TGGTTTACTG CTCTGCTGCC ACATCTTGAA ATTCTTAATA    3120

AAGGGCCTCA TGTTTTCATT TTGCTTTACT CTCTGCAATT ATGCCGTTGG TCCTGCCCAG    3180

AGCTCTAGAA GCTGTTTCAT CCTCATAGTA AAAGTGCTCT GCTTTCAGCT CTCCAGCTTT    3240

TAGCACTATA CCCACAGCAC AACTGACTCA CTAGTCCTAA TTCCATATTC TGGAGAGGGC    3300

TCCAAAGTGG CCCACTTTGG AGAAGTTGTC CATCTGGGTG AGGTTGCATG GCACAAACCT    3360

GGCTTCAGGC CTACTCCAAA GGATGGGGGT GGGGAGTGT GAGTTCCTAG AAAAAGTAGA     3420

GGTGGGTGTC ATCTGGTGAA TGTACGTGTG GGGAGGTAAG AAACGGGACA GTTTGCGTCT    3480

CAATTCATTT GAAGACATAA GAAAGCAAAA TGTTCCTTGC CACATTTAAG GTAGTATGGA    3540
```

```
GAAACATGTC CCACAGTGGC CTTAAATATC ACTCTGAGCT CGAGTCTTGT GGTGGCTCAT      3600

GAACCATGGA GGACCTAGAG GTTCGAAGGG CAATTGACGC TTATCAAATG CCCTTATGTG      3660

CCAAGCACTG GGACTGGCCG ATTGGCATAC AAACCTAATT TAATTCTCGC AGGGAATGCA      3720

CGACACAGTT GATACCAGCC CATTTGACAG CCTGAGGACA TGTGAGTTGC TAAACCACCT      3780

CCTAAAGGCA ATGCAGCTTC TAAGTGGCAG AGTTTAGGAT TGAACGAGAA TTTGCCTATT      3840

TCAAAGTTTG TCCCCTCTCC TTGATGGTCT GTGCCTCCCC TGTCAAAGTC CAAAGGCTGA      3900

TTAGAAATTA AACATCATTA GCCAAAGCTG ATCAACAGCA GAGCCCCCAC TTGCAGATGG      3960

GAATGGTGAG AGAGGGAGAC TGAAACACTT TTTTCTTGGC CTTTCAGGGT TTAGAATCCA      4020

AGCTTAAGTT TCTGCCTTCC TGTCCCTTGT GTAGTGGTTG AGGACATGGA CTGAGCCCAT      4080

GCTCCAGATG GTATTTCTCC TCCAGTGCTC TCCCATCCAG CCCCCAGCCA ACTCTGGGTG      4140

CCATGAATGG GACTACGTCG GCTTTTACAG ACAGTTGTCT CCTCAGAGAC CGTTACAGTG      4200

CCTGACTCAC AGTAGGTGCT CAGTAAAAAG TGTTAAATGA ATGAATGGGC CTAGGTTTGT      4260

GTCCTGGGTC TATCATTCTC CAGCTGCCTA AGTTTGGGAA ATTGGCCTCT TGGAATCTCA      4320

GTCCCTCCCC TACAAAAGGG CAGCAATGAT TGTACTTTAT AGTTTCTAGT AGCTAATGAG      4380

ATAGCAACAG ATACTACAGA GGGCTCAGGA AATGCTACTG GTTATTATTA TTATTTTTTA      4440

TTTTATTTAT TTTTTGGGAG ACGGGGTCTT GCTCTATTAT CCAGGCCTGG GGTGGAGAGG      4500

CTCAATCAGA GCTCACTGCA GGTCCTCAAG CAATCCACCC ACTTCACCTC CTGAGTAGCC      4560

GGGACCACAG GCTGGTGCCA CCATGCCTGG CTTTTTTTTT TTTTTAAAC TTAAAAAACA      4620

TAGGCGGCTC CCTATGTTGC CCAGGCTGGT CTCAAACTCC TGGACTGAAG CGATCCTCCT      4680

GCCTTATCCT CACAAAGTGC TGGGATTGCA GGCATGAGCC ACCACACCTG GCCTATGTTT      4740

AATATTATTG ATAATTCACC TCCTCACCTT CAATGCCTTC TTGCCTAGAG GAGGAGGCAG      4800

GTGAGCCCTT TCTAGTCCCC AGATAAGGTC CTCCAGCAGA TTCCTGAGGG ACCCACTTCC      4860

AGGCACAGCC CCTCATCTCC CTCTCCCTAC GAGAAGCTGA AGGAGTTCAG CTGCCAGCCT      4920

GTGTTGAACA GCTACCAGTT CCACATCGTC AATGGCGCAG TGGTTTGTGA GTAGCCTTTT      4980

CTGTATGGAA ATGTCTTTTA ACCTGGGCCT TTCCTTAACG TTCACCTCCT CTTTGACCCA      5040

GAGATCTTTT AGAAAATGAA ATGCTTCCAA GTGCTTGGAA GGAGATATTC CTGAGCTTTC      5100

TCCTGATGCT CCAGAGCTTC TCAGAGTGTC CGTGCTCATC CTGCCCTGGT CTCTCCCACC      5160

CATGAGTGTA CCTCCTGAAC TCTCTGGGGG CCCAGAGCCT GGCAGATAGT ACATGCTCAG      5220

TAAATACTTG TTCACTTGAG CTAATCTTGA AGCTTCCCTT GACAACTGCT GCTGTTGAGA      5280

ACATGTTTCC TTGTTTCTGT GATTTTGTTA ACAAAACGGC TCAGCTGTCT TCCAGTTGGA      5340

CAAATATTTA TTAAGGGCGA CTGCATGCCA AGCACTAAGA TAGGTGCTGC CAGGGCCACA      5400

AAAGCAAATA GGTGGGAAGG GAAGGGGGAC TCACATGTTA CTGAGACCAT TCAAGGAGCC      5460

ATGTGGGCAA GTGGATCAGT GCCCTTCACA TGGGGCGTGG CCTGGCATCC GGAGCGTGTT      5520

CTGCGGCTGG TAGGGTATGG GTATGTGCAG GGCAATCCTG GCCTAGACAG CAGGCACATT      5580

TGGAGGCACG GGACAGTAGT CTTTCGTGAG CACCATCCTT TCCAGCATAG CCAGGGTGGA      5640

TCCTGGGGTC CTGGGCTGGG AGGGTGAAGA GCAACAAATA AAGAAGTGGC TTCTTGGCCG      5700

GGCGCGGTGG CTCACGCTTG TAATCCCAGC ACTTTGGGAG GCCGAGGCGG GCGGATCACG      5760

AGGTCAGGAG ATCGAGACCA TCCTGGCTAA CACGGTGAAA CCCCGTCTCT ACTAAAAATA      5820

CAAAAAAAAT TAGCCGGGCG TGATGGTGGG CGCCTGTAGT CCCAGCTACT CGGGAGGCTG      5880

AGGCAGGAGA ATGGCGTGAA CCCGGGAGGC GGAGCTTGCA GTGAGCCGAG ATTGCGCCAC      5940
```

-continued

```
TGCACTCCCG CCTGGGCCAC AGAGCGAGAC TCCGTCTCAA AAAAAAAAAA AAAAAAAAAG    6000

AAGAAGTGGC TTCTTATAGT GTGTGGCTCA CTTCCTGCCT GGCCTCGTGG GGTTGCATGA    6060

ATCACTTTCC TTCCCAGGTG TATTTATTCA GAGCTGTGAG TGCACCTTGG AGTTCCTCTG    6120

TTTCCTCCTG AGGTCAGGGA ACTACCACCT CTCTGCCACT CATCCCCTAT GGCGGGAGAT    6180

ACATCCTCCA TCCCGTAGTG GGTTCCAGGG CTCAGAACCC TGGTACTCCT GAGCTCCCCA    6240

ACCCACCACT TCAGCTCAGC ACACACCAAT ACCCAGAGTT AGGACTGTGA GGTCTCCCTG    6300

GCACCAGCTG TGTGGGTTGG GGGCTCGGAC CCCTGCACCG GGAGGACCTG CCTCAGCTCT    6360

TGGCCTGCCC TGCCCACTGC CACCAGCACG TGGTTGACAG GGAAAGAACC CCCTTTTGTT    6420

CCCCACGTGA GCTCAAGCAA TCCACCCACT TCAGCCTCCT GAGTAGCTGG GATTACAGGT    6480

GCCCACTGCC ATGCTTGACT AATTTTTTGT ATTTTTAATA GAGACGGGGT TTCACCATCT    6540

TGGCCAGCTC AGCACACACC AATACCCAGA GTTAGGACTG TGAGGTCTCC CTGGCACCAG    6600

CTGTGTGGGT TGGGGGCTCG GACCCTGCAC CGGGAGACCT GCCTCAGCTC TTGGACTGCC    6660

TGCCACTGCC ACCAGCACGT GTTGACAGGG AAAGAACCCC TTTTGTTCCC ACGTGAGCTC    6720

AAGGAGACTT CCCTGAGTTG GAGCTCTCTG GTGTGGTCCT TCTCAGGCCT AAAGCAAAGT    6780

GTCTTTTCTG TGACACCTCC AAGGCCATGT TCAGGAGAGG GGAAGGGATC AGGGCCTGGT    6840

GGGAGGGATG GGGAGAGGGG ACTGGAGAAG GTGGCCTCCA GGGATCGAGT TTCCCATGGC    6900

CTCTTCCCAC CTGTCTTTGC CACAGGGGTG GGGACACCTG GCTGGCCCAG CCCAAGCCTC    6960

CACCCTGGGC TCCTGTGGGC TGGCTGCACT CGCCAGGGCT GGCCTAGGCT CTCTGCACCC    7020

AGGGAAGCTT CTCTATTCAA TGCTCTTCAC CCTCCCAGCC CAGGACCCCA GGAGATGAGG    7080

GAGAGTGGAG CAAAGGTTGA GGAGCAGAGG CTGGAGCCCC AGGCAGTGGC ACTGCTGGGC    7140

AGTGGTGGGA GGTGCCAGCC AGGGCTGGGA GTTGGACCCG AAAGTACGTG GCCTGGGCTG    7200

TACTTTCTTC CCACGTTGCC CCTTCAGAGC AGAAGCAGCC AGTTGCTCCT GAAGCCTTGA    7260

CCAGGGCTCC TGAGTCCAGA GCCTTGCTCA GGGCACTAGC GTGGGAGGAG GCTTCCGCAT    7320

CAGTACAGGG CATCAGCACC CGCCTCCTCA GCTGACCCAG CCCCGTGAGG ACCCAGGCCC    7380

AGCCCCCTGT CATCCCCACC CCCACCTTGC CAAGCCCCTG CCCCCAGGAG CAGGGCTGAG    7440

AGCGAGGTGA TCTGGGTTCT AATCCAGAGT CTGCTGCTGA CATGTGCTGA GCCCCAGGCC    7500

CATTGGTTTA CTTGCCCCAG TATTGAGCGA GCATCCACTG GGTACCCGCC CAGTGCCGGT    7560

GCTGTGCCAG GGGCCGGGGC ACAGAATAAA GCAGACCCGT CCCTGCTCTT CTGGCATTCA    7620

CAGTCTTGTG GAAACTCCAG ACTGAAAGTG CCCTTAGAGA TTATCCAGAT CAGCCCCTCC    7680

TTGTAGCAAT GAAGAGACTG AGACCCACAG AGGGGATGAG TTTGATCCAA GAAACAGACA    7740

AGATTAAGAT GCATGTGTCT TGAACCTTTT CAGTGCTCTG GAACATACCG TCTGGCCGGA    7800

GTTGTCTGGG CTTTGGTTTT CCCATCCATG AAATGGGTAC AATAACAACA GCTATAGTGT    7860

ATGAGCCTCT GTGATAGATG CTGTACGCAC AGCACCTGAA CTCACATGAT AAACCACTGA    7920

GGTGAGCATT ATCTCCCATT ATCAAGGAGG ACCCTGGGGC TCAGAGAGGT TAAGCACGAT    7980

GCCAAGGCCA CACAGCCAGG GAAAGAAGAG TTGGAATTCA AACCCCGGGT GCCCTGTCTC    8040

ACACTAGCTT CCCCTGTGGA GGGTGCTGGT GTGTGCATGA TTGGAGGCCC TCACACAGTG    8100

TAAGTCTCAG GATCTGCAGC AAACTGGTCA GAATGCTCTG CCCTGGCCCA GGGAAGGAAA    8160

GAGGGGCAGA TGGAGTTTGC TTCGCTGTAA GGCCCCGGAG CTTTGTGTTC CTGCTGAGAA    8220

GCCTCAGAGT CGGGCAACAC TGGGTCTAAT TCCAGCTCCA CCCCTTGTAT TAATAGCTGG    8280
```

```
GCCTTAATCT CCTCATCTGT AAAATGGAGA GAATCGTCGC CTGTACTTCA TAAGGCTGCT    8340

GGAAGGATTA GCTAAAGCAA CCCAGCTACA GTGGCTGGCC TACAGTAGGT GCTTCATTAA    8400

TGCCCTTCCT TTTAGATGTG GAAATTCCTC TTTTTGTCCA AGTTTTCTTT TCCTCTTTGC    8460

TTACGGCACT GGGATTTTCT TTATTACTGT TTCTTTGAAG AGTCCGCTCT GTACTTGTGC    8520

CCACGGCTAT GGTCAGTAAC CCCTTATGGA ATAAAACCCC TTTCCTGGCC AGGTGTGGTG    8580

GCTCATACCT GTAATCCCAG CACTCTGGGA GGCTGAGGCG GGAGGATCAC TTGAGCCCAG    8640

GAGTTCGAGA CCAGCCTGGG CAACACAGTG AGACCCTGT CTCTACTAAA CATACAAACA    8700

ATTAGCCAGA TGTGGTGGTG CATACCTGTA GTCCCAGCTA CTCAGAAGGC TGAGATAGGA    8760

GGATCACCTG AGCCCAGGAG ATGAGGCCAC AGTGAGCTGT GATTGCACCA CTGCACTCCA    8820

GCCTGGGCAA CAGAGTGAGA CCCTACCTCA AAAAGAAAGC AACAACAGAA AACCTATTTC    8880

CCTATCCTAA TTGCACCTCC ATTCAAAGAG CTGCCCCTGC AAGAGTTAAC CAACTCCCTA    8940

GCCTCCCATG AGTTCTGAAA TCCTGCACCC AGGCCTGGTC CCAGTTGCCT AGCAACCGGG    9000

GGCTGCTCTG GGATGCAGTA GGTAAGCAGG GGAGGGAGAG GAAGAAAACA ACTTGGTCTG    9060

TCCACGACTC TAAATGTCAC TGAGAGATCA GTGCAGAGAA AGGCCTGTCA CCAGAGCCCA    9120

GGGCCCAATT TGCCTGGTGG TAGGGACAGC TGCCCTCAGG CCACCTGGGA GGTGGTTATC    9180

CCTCCTTTGA GTGGGCTTAC ATAACTACTT GGCATTTTTG CAAGGGACTT TAAGCTCACT    9240

CAGCAGTGAC ACCCCCCTCC GCCCACATGC ACATACATGT GTGGTACAGG GAGGACCCGG    9300

TGTGGGAGGC AGAGATGGGG TTCCAGCCAA CTGAAACTCC ATCATCTGCA TCTCCCGGCC    9360

TCTGACTGCC TCCCTCTGCC AAAGCGGGAA GATGAAAATG GTAACTGCTG GAATTTGTAT    9420

TTTGCAAAGA CTTTTCTCAT TTACTGCTGA ATATATTCCT CATCTCAGCC TCCACTCGCT    9480

GACACGCTAC CCACTGTCTC TCCCAGCATT CATCTCTACC TGAAATGATC TTGTTTACTT    9540

CTCTGTGTCT GTGTGCCTCG ACTCTCCCCC ACCGACTAGA AAGGTCCGTG AGAGCAAGGA    9600

GCAAGCCTGT CTTGTTTGAG GGCACTGGTT CTCATAGAGC CACAGGGAAT GATGCCCCTG    9660

GACTAAGCAG TGTGGGGTCT GCTGGCTTGC ACCTGTGCCC CCAGCTCCTA GCCAAAGACC    9720

AGACACATGT TGGGAACTCA ATACTTGTTT GTTTAATGAG TAGATGAACA AAAGCACTCA    9780

TGAAATAGGC AGTGCACGTA TCTTTATCAC CATTTGAAAG CTGAGGAAAC AGGCTTGGAG    9840

AGGGAAGCAA CTTGCCTGAC ACCCCAAATC ACAGAAGCAG CATATTTGGC CCAAGAACCT    9900

GGCTTCCTGT CTCCAAGGGG TCAGGTCCAG CTGGCATTGG CCTGTAGGCA TGTGAGTGTG    9960

GCAAGGTAGT CAGCAAAGAG CCTTTACTGC ATGTTGGGGT CAGAAGATCA GCAATAAGGA   10020

GGACAAAATC CTTGCCTGGA AGGAGCTTGT GTTCCAAAAA GAACAAGAGA CCACAGCATA   10080

TTCATTAATA AAGACACATT CAAACAGGGC CAAGTGCTCT GAAGCACCTC AGACAAAGCG   10140

ACAGGCTGCA AAATGACAGC GTTTGGGGGT CAGGAGACAA AAGGGTGCCT GCTTTAGGTG   10200

GTCGAAGAAG GCCTCTCTGG GGAGGTGGCA TTTGGTCTGA GACCTCAGGG CCAATGTGCT   10260

AGGAGCAGAG GAGCCTTGGG GAAGAATGGA GATGAGGTTG ACAGGATGA GACACGTGCC    10320

TTCTATGTCA ATGGCAAGGG AGTCATTGGA GCATGTGAAG CAGAGGATGC TCTACTTTTG   10380

CCCCAGAAAG ATCACTCTGG CTACAGTGCA GAGAAAGAAG AGAGTCAAGG AGGAAAGAAG   10440

GGCCTCATTA GGGGACTGTT GCAAAGCACA GGGAGGCACA ACCACAGCCA AGATCAGCAT   10500

GGTGACCAAT GGATGGAAGT GTCAGATGTC GCATGCTGTC GGTAGGTCAG GGCCGACAGG   10560

ACCTGTCGAT GGGTTCAGCG TGGGGTGTGA AGGAACACAG GCTGCACCCC AGCTCCTGGC   10620

CTGAGTGGCT GTAGATAGTG GCACCAAATA CTGAGCTCGT GAAGATGGGG GAGAGCTGAT   10680
```

-continued

```
GATGAAGACA GCAAGAGTTT GGTGTGAGTC ACCTTGAGTT TGAGACACGT GTCAGACATG   10740

TAAGGGGTAG GCAGGTGGAC ACGTGCTTAT TGAAGTCTGG AGCCAAGGGA GAGGTGTGGG   10800

CTGCAGCGGA GAAGTTGGGA GTATTCAGAG TTCTGACACT GACCAAGAAC ACCCCTCAGA   10860

GAATTCAGAG ACAACCAGGG CTGAGGCGAG GGGCTTAGAC TGGGGCCTGG ACAGCCACA    10920

GGCAGGAATG CAGACTTGCT GCCTCTTCTT ATTTGTGGAG ATGTAGTTCA TGCAGCAAGA   10980

AAGTCATTCC AAAGCCCTCC TTTCCTTTCT TCATGCCTCA GTTTCTCCAT TAGCACATTA   11040

AAAGATGCAA GATCTGGAGT TAAGCTTGTT TTTAAAAGGT GGCCTCCAAA GACGGTTTTT   11100

CTTGGCCTGG GGCTGTCTCA TCATCCAGGT CATGACAGGC CCGGTCCATG GTTGAGGAAT   11160

GCCACAGAAG TGACAGTCCA CTGCAAAAGA CTGCTGCTCC AGATCAGTTC TGGAAGGCCT   11220

GGCAATGGGG CAGGCCACTG AAGTAGAACT GGATGTCAGA TGCACGCATT AGAAAGGACA   11280

GGAAGACCAA ATGAGAAAGG GAGAGGGGGC AGGGAGAAAG GAAGGAGAGC TAGAGACTTG   11340

AGGCAAAGGA AACAAGAGAT GGAATAGAAG AAGACAGAGG ACCAGAAGAC AGTGAGACCA   11400

ACAGAAAGAG AGAGGGACGA GAAAGAAGGT GGCTGAGGAA GGTGAGAAAA GTGTTTCCAG   11460

GGCGACAGCA ACTGGACCAG GCCCTCTAGT TGGACAGTGA GGCTGGCTGG GGGGCCTGAG   11520

CTCAAGTAGC CCTCGTCCCC TGAGAGTG GGGGCTACCT GGGGAGCTGG GCTTGATGCA    11580

TCTGGAAGGA TCTTCACAGA GGCAGGAGGG GGAGTGGGAG GGCAGAGGGC ACCCAGGCGC   11640

TAGAACAGTG GGAGTGGCGG GACGCAAAAC CGGAGAGCCA GAGGAGTGAA CATCCCTGGC   11700

AGATTCCCCT GCGGCCGAGC AGGAGGGCAG GAAGCTCAGT GGTGTTGGCA CAACGTGAGA   11760

AGTTCCAGGG AGGCGTGGGA GGACGGCTTC TGCAGGACGC AGACTTTGCA GAGGGAGAGT   11820

GGCAAACAGA CTGACTGCAG GCAGCTCTGC CGGCTCCACA GGGCGCTGCT TTTTCTCCAC   11880

GGTGGAGCTG GAGTGCATCA CCCTGAGAAC CAGCAGCAAG CCCCCACAGG GCACCTTCTG   11940

CGTGCCAGGC ACATCCGGAC CACTTGTCGG TAGACACCAG TGACCCTCAC CACCACCCCA   12000

GGAATGGGAC AGTGTCATGT GTTTCTGAAA TGACTAGGTT TTAGCACCAT TTCATAGATG   12060

AGGAAGCTGA AGCTAACTTG CCCAAGGTCA TAAACCGGGC GTCTGGTGGC CTCCCCTCCT   12120

CACTGCCAAC CCTGAGAGCG GACTAGGGTG GAGTTATCTG GAAAGAGGAA GCTGTACCTG   12180

AGAGCCCTAA ACACACATGC GCGCGCACGA CACACACACA CGCACAAACA CACAATGCAC   12240

GCACACACAT GCGCACGCAC ATACACACAC ATGCACACAT GGACACATAC CTGCACACAC   12300

AAGCATACAC ATGCACACAG GCACACGCAT GCACACACGC GCATGCACAC ACATGCACAC   12360

ACATGTGCAT GCACACAGTG CGACAGCTCT GATTAGTAGG TAAATAAAAG GTTCCCATCT   12420

AGTGGTGACT CGGCCAAAGT GCAGACACTG AACCCCAAAG GCCCATAGAG GCTTCATTCA   12480

TCCCTTCTCT TATTCTTCAT TCATGGATTC TATTGAGCAT CTGCTCTGTG CAGCATCTGT   12540

CCTGGATGCT GGGGATACTG TGATGACTTA GACAAGGTCT CAGCCGCACA CAGCTTATGC   12600

TTCTTTGAGG GGAGGCAGAC ACAAGCCAGG AAACCAATAA GAGAAGTTAA GTAAAAAGCA   12660

CAGTGAGTGA GACAAACGGG TACGGAGGAC ATGGCCAGAG AGAGCTTTAG TTCAGGTGGT   12720

CAGGGAGCAC CTCTCTGAGG AGGTGAAATT TGACCAAGCC TCAAACAGTG GCAGGGATCC   12780

CACTGCTTGC AGATCCTGGG GAGAAGCATT TTAGACAAAA AGAACAGCAA GTCCAAAGGC   12840

CCAGAGACAA GACAGAGCAA GACCTGTGAC ATGAAACAGG CTGGTGTGCC CAGAGCAGGG   12900

AGGCTGGGAG AGTGGAGGGG GAGGGCGATG AGGGTGAGA GCTGGTGAG GGTGGCATCC    12960

CGGCAAGTGT GCCTGGCCAC GGAGGCCACG GAAGGATTCA GCATGTCTTT CCCGAATAGG   13020
```

```
AACCACACTG GGCTGTAACA GAGAGTGACG TACTCGGTAC GTTGAGAAGG TCCTGCTTAT    13080

TTCCTTCCGT GAAGGAGGAA GAGCTGCTGA TGACAGAGAT TGGCAGTGGC CAAAGACATA    13140

GAGAGAAGAG GGCAGAACAT GGGCTATTTT AAACACAGAG AAGATTAGCG GGACCCGCTG    13200

GCAGACCGGA CGTGAAATGT GGAAGGAGCG GGGGCAGCGA GGTCGGCTCC TAGTTTCCTG    13260

AGAATGTGGG TGAATCACGG GCTCACAGGC AGAGGGAGCA CTAGGATATC AAGGGTTCCC    13320

TTGTGAACGC CTCAAGTTGG AGATGCCTGA GACATCCAAG TGAGATGTCA AGCAGGCAGC    13380

TGGAAATAGG AGATGAGCTC TGGGAAAATG CTCCCATCAC CCTGGCCTGT GTGCTGCCTG    13440

GGCGCACCCA TTCAGGGCCC TCCACGCAGC CCACGCCCCT GCCTCCTGAT TCCTTCTAGG    13500

CTTCTCCAGC ACTCGTGGGA TGCCCAGATG TGATCAGGGA AGGGCTTGAG GATGCAGGGA    13560

AGCTGTGGCT GAGAGCCCTA AACACACACA TGCACACGCA CACACACATA CACAGGCACA    13620

TGCACACACG ACCATACACA CACACAAATG CACGCAGATG CACACAAATG CATATGCACG    13680

CACACAAATG CATATGCACA CACACACATG CACACATATG CATACACGTA TCCCTTTCAG    13740

TGGCTTTCCT TTCTGTCCTT AACCCTTGGC CCCTTACAGT GAGCTCCCAG TTCTCCCCAG    13800

CCTTAGAACC AAACCCTGGG GCTGGGCTGG GAGCCCCCAG TGACCCTCTG TGTCTCTGTA    13860

GGTGGATGCA CCCTTGGTCC TGGTGCCAGC TGCCACTGCA GGCTGAAGGC CTGTGAGTGT    13920

GACAAGCAAT CCGTGCACTG CTTCAAAGAG AGCCTGCCCA CCTATGAGAA AAACTTCAAG    13980

CAGTTCTCCA GCCGGCCCAG GTGTGGCAGA CATAAGCCCT GGTGCTAGGG ACACCACAGG    14040

GTCCCTCTCA TCATCCAGCA TCCGCTCTAG TGTTGCTCTT CCAGGAAGCC TTCTCAGATC    14100

ATCCCCAACA GGCCCCTGTT CTTCCACTGG GAGGGAGGAC AAAATGTCTC CCGCAGGGCA    14160

GCTCACCCTT CAGCATTCTG ACCAAGGGGA CTCCCTGTCG TTCAGCATCA GAGGGCTGGA    14220

GAGCAGAAAT GGGAAAGATG AGATGCCTGC CCTGCAGGAG CTGGCATTCT GTGGAGTGGG    14280

GAGGACTACA AATGCATGGA TATAGAAGTA AGAGACACAT TAGACTGTAG TAAGTGCTAT    14340

GATGCAGTAA ACAAAGGGA CGGGATAGAG ATGCACCCAA CCCCACATCC CAGGGGTTTC    14400

CAGGAGGGGA GAAGCCCCAG GATCTACCCC AAACTCTCTC TTCACCCCCA CTGCAAACCG    14460

GGACACAGAG CAGACTTGAG CGCCAGGCCC ATGCCCAGCT CTAGCTGGCA ACAAAGCCAC    14520

CACTTTCCTT GCCCCTCTGC GTCCTCAGTT TTTATGATGT CATTCTTAGC TTTTCTTATC    14580

AAGAGGCAGA ATCTGTTTTC CCCATCCCAT GAATCTGAAC TGGTCTTGTG GCTTAGTTTG    14640

GTCAATAGAA TGTTGTGGGA GGGATGGTTT ACCAGTTTTG AGCTAGGCCT CAGGAGGTCT    14700

AGGGCATGTC TACTCTCTCT TAGGACAGCT GCCCCCACCC TGCAAAAAAG CCTGGGCTAG    14760

CCTGCTGGAG GATGAGAGCC CACCTGGATC AGTTGTCTCA GCTGATTTCA GACACGTGAG    14820

AGAGAGCTCA GCGAGACTCA GCTTGTAGCT GACTACAGAT GTGTGAGGGA ACCTGGCTGA    14880

GACCAAAACA ACTGTCCAGC TGAGCCCAGG CTAAACTGCC AACATGCAGA ATTGTGAGCT    14940

AAATAAAGGC TGCTGTTCTA AGTCACTGGG TTTTGGTATG GTTTGTTAGG CAGCCATAAC    15000

TAACAGGTGT AATTGGTCCT TATTCCCTTA TTCACTGAGA GTGATGGGTT CTCAGCCCTG    15060

AGCTGGACTT GGAGGCCATG GAAATGCAGT GGACATGGCC TTTGTTCCTT ACCTTGAAGC    15120

TGTGGAAGGA GGTCAAGTTC ATGGAATAAT GGAGAACACA CAGCTGTAAT CGTTTGCTTG    15180

TTCAGGGAAC ACACATTTAT TGAGCACTTG CTATGTGCCA GGCACAGTGC CAGGCAGTAG    15240

GGATCCAGAT ATTTAAAGAA AACAAACAAA AATCAGGTCC AAAACTCCTG GGGAGAATGC    15300

TGAGAGTGGT ATCAGCTTTT AGGAATTC                                     15328
```

(2) INFORMATION FOR SEQ ID NO:34:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

```
Met Lys Leu Leu Leu Leu Ala Ala Leu Leu Thr Ala Gly Val Thr Ala
 1               5                  10                  15

His Ser Ile Ser Thr Arg Ala Val Trp Gln Phe Arg Asn Met Ile Lys
             20                  25                  30

Cys Thr Ile Pro Gly Ser Asp Pro Leu Arg Glu Tyr Asn Asn Tyr Gly
             35                  40                  45

Cys Tyr Cys Gly Leu Gly Gly Ser Gly Thr Pro Val Asp Asp Leu Asp
         50                  55                  60

Arg Cys Cys Gln Thr His Asp His Cys Tyr Asn Gln Ala Lys Lys Leu
65                  70                  75                  80

Glu Ser Cys Lys Phe Leu Ile Asp Asn Pro Tyr Thr Asn Thr Tyr Ser
                 85                  90                  95

Tyr Lys Cys Ser Gly Asn Val Ile Thr Cys Ser Asp Lys Asn Asn Asp
                100                 105                 110

Cys Glu Ser Phe Ile Cys Asn Cys Asp Arg Gln Ala Ala Ile Cys Phe
            115                 120                 125

Ser Lys Val Pro Tyr Asn Lys Glu Tyr Lys Asp Leu Asp Thr Lys Lys
        130                 135                 140

His Cys
145
```

(2) INFORMATION FOR SEQ ID NO:35:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

```
Met Lys Val Leu Leu Leu Ala Val Val Ile Met Ala Phe Gly Ser
 1               5                  10                  15

Ile Gln Val Gln Gly Ser Leu Leu Glu Phe Gly Gln Met Ile Leu Phe
             20                  25                  30

Lys Thr Gly Lys Arg Ala Asp Val Ser Tyr Gly Phe Tyr Gly Cys His
             35                  40                  45

Cys Gly Val Gly Gly Arg Gly Ser Pro Lys Asp Ala Thr Asp Trp Cys
         50                  55                  60

Cys Val Thr His Asp Cys Cys Tyr Asn Arg Leu Glu Lys Arg Gly Cys
65                  70                  75                  80

Gly Thr Lys Phe Val Thr Tyr Lys Phe Ser Tyr Arg Gly Gly Gln Ile
                 85                  90                  95

Ser Cys Ser Thr Asn Gln Asp Ser Cys Arg Lys Gln Leu Cys Gln Cys
                100                 105                 110

Asp Lys Ala Ala Ala Glu Cys Phe Ala Arg Asn Lys Lys Ser Tyr Ser
        115                 120                 125
```

```
Leu Lys Tyr Gln Phe Tyr Pro Asn Lys Phe Cys Lys Gly Lys Thr Pro
    130                 135                 140

Ser Cys
145

(2) INFORMATION FOR SEQ ID NO:36:

(i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

Met Lys Leu Leu Val Leu Ala Val Leu Leu Thr Val Ala Ala Ala Asp
1               5                   10                  15

Ser Gly Ile Ser Pro Arg Ala Val Trp Gln Phe Arg Lys Met Ile Lys
                20                  25                  30

Cys Val Ile Pro Gly Ser Asp Pro Phe Leu Glu Tyr Asn Asn Tyr Gly
            35                  40                  45

Cys Tyr Cys Gly Leu Gly Gly Ser Gly Thr Pro Val Asp Glu Leu Asp
        50                  55                  60

Lys Cys Cys Gln Thr His Asp Asn Cys Tyr Asp Gln Ala Lys Lys Leu
65                  70                  75                  80

Asp Ser Cys Lys Phe Leu Leu Asp Asn Pro Tyr Thr His Thr Tyr Ser
                85                  90                  95

Tyr Ser Cys Ser Gly Ser Ala Ile Thr Cys Ser Ser Lys Asn Lys Glu
            100                 105                 110

Cys Glu Ala Phe Ile Cys Asn Cys Asp Arg Asn Ala Ala Ile Cys Phe
        115                 120                 125

Ser Lys Ala Pro Tyr Asn Lys Ala His Lys Asn Leu Asp Thr Lys Lys
    130                 135                 140

Tyr Cys Gln Ser
145

(2) INFORMATION FOR SEQ ID NO:37:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

Met Lys Thr Leu Leu Leu Ala Val Ile Met Ile Phe Gly Leu Leu
1               5                   10                  15

Gln Ala His Gly Asn Leu Val Asn Phe His Arg Met Ile Lys Leu Thr
                20                  25                  30

Thr Gly Lys Glu Ala Ala Leu Ser Tyr Gly Phe Tyr Gly Cys His Cys
            35                  40                  45

Gly Val Gly Gly Arg Gly Ser Pro Lys Asp Ala Thr Asp Arg Cys Cys
        50                  55                  60

Val Thr His Asp Cys Cys Tyr Lys Arg Leu Glu Lys Arg Gly Cys Gly
65                  70                  75                  80

Thr Lys Phe Leu Ser Tyr Lys Phe Ser Asn Ser Gly Ser Arg Ile Thr
                85                  90                  95
```

```
Cys Ala Lys Gln Asp Ser Cys Arg Ser Gln Leu Cys Glu Cys Asp Lys
            100                 105                 110

Ala Ala Ala Thr Cys Phe Ala Arg Asn Lys Thr Thr Tyr Asn Lys Lys
            115                 120                 125

Tyr Gln Tyr Tyr Ser Asn Lys His Cys Arg Gly Ser Thr Pro Arg Cys
            130                 135                 140
```

(2) INFORMATION FOR SEQ ID NO:38:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

```
Ala Val Trp Gln Phe Arg Lys Met Ile Lys Cys Val Ile Pro Gly Ser
1               5                   10                  15

Asp Pro Phe Leu Glu Tyr Asn Asn Tyr Gly Cys Tyr Cys Gly Leu Gly
            20                  25                  30

Gly Ser Gly Thr Pro Val Asp Glu Leu Asp Lys Cys Cys Gln Thr His
            35                  40                  45

Asp Asn Cys Tyr Asp Gln Ala Lys Lys Leu Asp Ser Cys Lys Phe Leu
50                  55                  60

Leu Asp Asn Pro Tyr Thr His Thr Tyr Ser Tyr Ser Cys Ser Gly Ser
65                  70                  75                  80

Ala Ile Thr Cys Ser Ser Lys Asn Lys Glu Cys Glu Ala Phe Ile Cys
            85                  90                  95

Asn Cys Asp Arg Asn Ala Ala Ile Cys Phe Ser Lys Ala Pro Tyr Asn
            100                 105                 110

Lys Ala His Lys Asn Leu Asp Thr Lys Lys Tyr Cys Gln Ser
            115                 120                 125
```

(2) INFORMATION FOR SEQ ID NO:39:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

```
Asn Leu Val Asn Phe His Arg Met Ile Lys Leu Thr Thr Gly Lys Glu
1               5                   10                  15

Ala Ala Leu Ser Tyr Gly Phe Tyr Gly Cys His Cys Gly Val Gly Gly
            20                  25                  30

Arg Gly Ser Pro Lys Asp Ala Thr Asp Arg Cys Cys Val Thr His Asp
            35                  40                  45

Cys Cys Tyr Lys Arg Leu Glu Lys Arg Gly Cys Gly Thr Lys Phe Leu
50                  55                  60

Ser Tyr Lys Phe Ser Asn Ser Gly Ser Arg Ile Thr Cys Ala Lys Gln
65                  70                  75                  80

Asp Ser Cys Arg Ser Gln Leu Cys Glu Cys Asp Lys Ala Ala Ala Thr
            85                  90                  95

Cys Phe Ala Arg Asn Lys Thr Thr Tyr Asn Lys Lys Tyr Gln Tyr Tyr
```

```
                100               105                110
Ser Asn Lys His Cys Arg Gly Ser Thr Pro Arg Cys
        115                 120
```

(2) INFORMATION FOR SEQ ID NO:40:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

```
Gly Leu Leu Asp Leu Lys Ser Met Ile Glu Lys Val Thr Gly Lys Asn
1               5                   10                  15

Ala Leu Thr Asn Tyr Gly Phe Tyr Gly Cys Tyr Cys Gly Trp Gly Gly
                20                  25                  30

Arg Gly Thr Pro Lys Asp Gly Thr Asp Trp Cys Cys Trp Ala His Asp
            35                  40                  45

His Cys Tyr Gly Arg Leu Glu Glu Lys Gly Cys Asn Ile Arg Thr Gln
    50                  55                  60

Ser Tyr Lys Tyr Arg Phe Ala Trp Gly Val Val Thr Cys Glu Pro Gly
65                  70                  75                  80

Pro Phe Cys His Val Asn Leu Cys Ala Cys Asp Arg Lys Leu Val Tyr
                85                  90                  95

Cys Leu Lys Arg Asn Leu Arg Ser Tyr Asn Pro Gln Tyr Gln Tyr Phe
            100                 105                 110

Pro Asn Ile Leu Cys Ser
        115
```

(2) INFORMATION FOR SEQ ID NO:41:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

```
Ala Val Trp Gln Phe Arg Asn Met Ile Lys Cys Thr Ile Pro Gly Ser
1               5                   10                  15

Asp Pro Leu Arg Glu Tyr Asn Asn Tyr Gly Cys Tyr Cys Gly Leu Gly
                20                  25                  30

Gly Ser Gly Thr Pro Val Asp Asp Leu Asp Arg Cys Cys Gln Thr His
            35                  40                  45

Asp His Cys Tyr Asn Gln Ala Lys Lys Leu Glu Ser Cys Lys Phe Leu
    50                  55                  60

Ile Asp Asn Pro Tyr Thr Asn Thr Tyr Ser Tyr Lys Cys Ser Gly Asn
65                  70                  75                  80

Val Ile Thr Cys Ser Asp Lys Asn Asn Asp Cys Glu Ser Phe Ile Cys
                85                  90                  95

Asn Cys Asp Arg Gln Ala Ala Ile Cys Phe Ser Lys Val Pro Tyr Asn
            100                 105                 110

Lys Glu Tyr Lys Asp Leu Asp Thr Lys Lys His Cys
        115                 120
```

(2) INFORMATION FOR SEQ ID NO:42:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

```
Ser Leu Leu Glu Phe Gly Gln Met Ile Leu Phe Lys Thr Gly Lys Arg
  1               5                  10                  15

Ala Asp Val Ser Tyr Gly Phe Tyr Gly Cys His Cys Gly Val Gly Gly
                 20                  25                  30

Arg Gly Ser Pro Lys Asp Ala Thr Asp Trp Cys Cys Val Thr His Asp
             35                  40                  45

Cys Cys Tyr Asn Arg Leu Glu Lys Arg Gly Cys Gly Thr Lys Phe Val
 50                  55                  60

Thr Tyr Lys Phe Ser Tyr Arg Gly Gly Gln Ile Ser Cys Ser Thr Asn
 65                  70                  75                  80

Gln Asp Ser Cys Arg Lys Gln Leu Cys Gln Cys Asp Lys Ala Ala Ala
                 85                  90                  95

Glu Cys Phe Ala Arg Asn Lys Lys Ser Tyr Ser Leu Lys Tyr Gln Phe
                100                 105                 110

Tyr Pro Asn Lys Phe Cys Lys Gly Lys Thr Pro Ser Cys
            115                 120                 125
```

(2) INFORMATION FOR SEQ ID NO:43:

(i) SEQUENCE CHARACTERISTICS:
        (A) LENGTH: 130 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

```
Ser Phe Trp Gln Phe Gln Arg Met Val Lys His Ile Thr Gly Arg Ser
  1               5                  10                  15

Ala Phe Phe Ser Tyr Tyr Gly Tyr Gly Cys Tyr Cys Gly Leu Gly Gly
                 20                  25                  30

Arg Gly Ile Pro Val Asp Ala Thr Asp Arg Cys Cys Trp Ala His Asp
             35                  40                  45

Cys Cys Tyr His Lys Leu Lys Glu Tyr Gly Cys Gln Pro Ile Leu Asn
 50                  55                  60

Ala Tyr Gln Phe Ala Ile Val Asn Gly Thr Val Thr Cys Gly Cys Thr
 65                  70                  75                  80

Met Gly Gly Gly Cys Leu Cys Gly Gln Lys Ala Cys Glu Cys Asp Lys
                 85                  90                  95

Leu Ser Val Tyr Cys Phe Lys Glu Asn Leu Ala Thr Tyr Glu Lys Thr
                100                 105                 110

Phe Lys Gln Leu Phe Pro Thr Arg Pro Gln Cys Gly Arg Asp Lys Leu
            115                 120                 125

His Cys
130
```

(2) INFORMATION FOR SEQ ID NO:44:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

Gly Leu Leu Glu Leu Lys Ser Met Ile Glu Lys Val Thr Gly Lys Asn
1               5                   10                  15

Ala Val Lys Asn Tyr Gly Phe Tyr Gly Cys Tyr Cys Gly Trp Gly Gly
                20                  25                  30

His Gly Thr Pro Lys Asp Gly Thr Asp Trp Cys Cys Arg Met His Asp
        35                  40                  45

Arg Cys Tyr Gly Leu Leu Glu Glu Lys His Cys Ala Ile Arg Thr Gln
    50                  55                  60

Ser Tyr Asp Tyr Arg Phe Thr Gln Asp Leu Val Ile Cys Glu His Asp
65                  70                  75                  80

Ser Phe Cys Pro Val Arg Leu Cys Ala Cys Asp Arg Lys Leu Val Tyr
            85                  90                  95

Cys Leu Arg Arg Asn Leu Trp Ser Tyr Asn Arg Leu Tyr Gln Tyr Tyr
            100                 105                 110

Pro Asn Phe Leu Cys
        115